United States Patent [19]
Stevens

[11] Patent Number: 6,039,948
[45] Date of Patent: Mar. 21, 2000

[54] METHOD FOR TREATMENT OF ANTIGENICALLY MODIFIED POLYPEPTIDES

[75] Inventor: Vernon C. Stevens, Dublin, Ohio

[73] Assignee: The Ohio State University, Columbus, Ohio

[21] Appl. No.: 08/469,043

[22] Filed: Jun. 6, 1995

Related U.S. Application Data

[62] Division of application No. 07/935,331, Aug. 26, 1992, which is a continuation of application No. 07/311,331, Feb. 17, 1989, abandoned, which is a division of application No. 07/073,748, Jul. 15, 1987, Pat. No. 5,006,334, which is a continuation-in-part of application No. 06/667,863, Nov. 2, 1984, Pat. No. 4,691,006, which is a continuation-in-part of application No. 06/472,190, Mar. 4, 1983, Pat. No. 4,526,716, and application No. PCT/US83/00777, May 18, 1983, which is a continuation-in-part of application No. 06/472,190, which is a continuation-in-part of application No. 06/323,690, Nov. 20, 1981, Pat. No. 4,384,995, which is a continuation-in-part of application No. 06/112,628, Jan. 16, 1981, Pat. No. 4,302,386, which is a division of application No. 05/936,876, Aug. 25, 1978, Pat. No. 4,201,770, which is a continuation-in-part of application No. 05/622,031, Oct. 14, 1975, abandoned, which is a continuation-in-part of application No. 05/462,955, Apr. 22, 1974, abandoned, which is a continuation-in-part of application No. 05/406,821, Oct. 16, 1973, abandoned, which is a continuation-in-part of application No. 05/357,892, May 7, 1973, abandoned.

[51] Int. Cl.⁷ ...................... A61K 39/385; A61K 39/395; C07K 16/18; C07K 16/26

[52] U.S. Cl. ..................... 424/184.1; 424/185.1; 424/193.1; 424/194.1; 424/195.11; 530/350; 530/395; 530/402; 530/403

[58] Field of Search ............................... 530/350, 395, 530/402, 403; 424/184.1, 185.1, 193.1, 194.1, 195.11

[56] References Cited

U.S. PATENT DOCUMENTS

| | | | |
|---|---|---|---|
| 2,301,532 | 11/1942 | Fell | 424/177 |
| 2,372,066 | 3/1945 | Fell | 424/177 |
| 2,388,260 | 11/1945 | Friedhelm | 424/177 |
| 2,744,890 | 5/1956 | Wagner | 424/177 |
| 3,317,400 | 5/1967 | Beusser | 424/177 |
| 4,122,166 | 10/1978 | Tribble et al. | 424/177 |
| 4,123,519 | 10/1978 | Tribble et al. | 424/177 |
| 4,161,519 | 7/1979 | Tolwar | 424/177 |
| 4,179,337 | 12/1979 | Davis et al. | 424/177 |
| 4,193,982 | 3/1980 | Avrameas et al. | 424/177 |
| 4,201,770 | 5/1980 | Stevens | 424/177 |
| 4,400,316 | 8/1983 | Katsuragi et al. | . |
| 4,526,716 | 7/1985 | Stevens | 260/112.5 |
| 5,006,334 | 4/1991 | Stevens | 424/88 |

FOREIGN PATENT DOCUMENTS 093652   9/1983   European Pat. Off. .

OTHER PUBLICATIONS

B. Cinader et al., J. of Experimental Medicine, vol. 125, No. 6, pp. 105 1073 (1967).
W.E. Nixon et al., J. Lab. Clin. Med. (1971), vol. 78, No. 6, pp. 949–956.
S.J. Gross et al., Immunochemistry, vol. 5, pp. 55–65 (1968).
M. Tabachnick et al., J. of Biological Chemistry, vol. 235, 1960 pp. 1051–1054.
Currie, J. Obstet. Gynaec. Brit. Cwlth., vol. 74, pp. 845–848 (1967).
Nisula et al, Cancer Res. vol. 34, pp. 512–515 (1974).
W.R. Jones, Immunological Fertility Regulation, Blackwell Scient. Publications, Victoria, Australia (1982), pp. 130–146, 158–171, 207–267.
Basic and Clinical Immunology, 3rd edition, pp. 44–52. Fudenberg et al. (ed), 1980.
Geysen, H. M. et al., J. Molecular Recognition, 1:32–41, Cognitive features of continuous antigen determinants, 1988.

Primary Examiner—Thomas M. Cunningham
Assistant Examiner—F. Pierre VanderVegt
Attorney, Agent, or Firm—Francis T. Kremblas; Kremblas, Foster, Millard & Pollick

[57] ABSTRACT

Endogenous and exogenous proteins, and fragments thereof, are chemically modified outside the body of an animal so that when injected into the animal they produce more antibodies against the unmodified protein than would injection of the unmodified protein or fragment alone. The chemical modification may be accomplished by attaching the proteins or fragments to carriers such as, for example, bacterial toxoids. The chemical modification can also be accomplished by polymerization of protein fragments. Proteins which can be modified include Follicle Stimulating Hormone and Human Chorionic Gonadotropin. The modified polypeptide may be administered to animals for the purpose of contraception, abortion or treatment of hormone-related disease states and disease disorders, treatment of hormone-associated carcinomas, and to boost the animals' resistance to exogenous proteins, for example viral proteins.

6 Claims, 7 Drawing Sheets

| Baboon No. | Mating 1 | | | Mating 2 | | | Mating 3 | | |
|---|---|---|---|---|---|---|---|---|---|
| | PRE-MATING TITER (ng/ml) | OVULATED | PREGNANT | PRE-MATING TITER (ng/ml) | OVULATED | PREGNANT | PRE-MATING TITER (ng/ml) | OVULATED | PREGNANT |
| 1374 | 108 | + | − | 110 | + | − | 97 | + | − |
| 1422 | 123 | + | − | 101 | + | − | 100 | + | − |
| 976 | 345 | + | − | 331 | + | − | 305 | + | − |
| 1068 | 95 | + | − | 89 | + | − | 91 | + | + |

FIG. 1

FORMULA A

FORMULA B

FORMULA C

REACTION I

FORMULA 2

FORMULA 3

METHOD FOR TREATMENT OF ANTIGENICALLY MODIFIED POLYPEPTIDES

This application is a divisional application of pending application Ser. No. 07/935,331, filed Aug. 26, 1992, which is herein incorporated by reference, which is a continuation of Ser. No. 07/311,331, filed Feb. 17, 1989, now abandoned, which is a divisional of application Ser. No. 07/073,748, filed Jul. 15, 1987, now U.S. Pat. No. 5,006,334, which is a continuation-in-part application of application Ser. No. 06/667,863, filed Nov. 2, 1984, now U.S. Pat. No. 4,691,006, which is a continuation-in-part of both U.S. application Ser. No. 06/472,190, filed Mar. 4, 1983 and of international patent application PCT/U.S. 83/00777, filed May 18, 1983 which is a continuation-in-part of the aforementioned U.S. application Ser. No. 06/472,190, now U.S. Pat. No. 4,526,716, a continuation-in-part of application Ser. No. 06/323,690 filed Nov. 20, 1981, now U.S. Pat. No. 4,384,995, which is a continuation-in-part of application Ser. No. 06/112,628, filed Jan. 16, 1981, now U.S. Pat. No. 4,302,386, which is a divisional of application Ser. No. 05/936,876, filed Aug. 25, 1978, now U.S. Pat. No. 4,201,770, which in turn is a continuation-in-part of application Ser. No. 05/622,031, filed Oct. 14, 1975, now abandoned, which in turn is a continuation-in-part of application Ser. No. 05/462,955, filed Apr. 22, 1974, now abandoned, which in turn is a continuation-in-part of application Ser. No. 05/406,821, filed Oct. 16, 1973, now abandoned, which in turn is a continuation-in-part of application Ser. No. 05/357,892, filed May 7, 1973, now abandoned.

BACKGROUND OF THE INVENTION

This invention relates to antigenic modification of polypeptides. More specifically, this invention relates to processes for modifying polypeptides which are not substantially immunogenic to the immune system of mammals so as to make the modified polypeptides more immunogenic. The invention also relates to the modified polypeptides so produced, to vaccines containing such modified polypeptides, and for processes for affecting in various ways the metabolism of animals using such modified peptides and vaccines.

It is well known that antibodies are generated in humans and in other animals in response to the presence of foreign antigens. It is also known to confer immunity on an animal by administering an antibody formed elsewhere. For instance, patents to Michaelson (U.S. Pat. No. 3,553,317), Friedheim (U.S. Pat. No. 2,388,260), Reusser (U.S. Pat. No. 3,317,400) and Peterson (U.S. Pat. No. 3,376,198) relate to production of antibodies, which when injected into an animal of a different species or into a human being cause passive immunization. In patents to Fell (U.S. Pat. Nos. 2,301,532 and 2,372,066), the patentee refers to active immunization using modified histamine in such animals as horses, cows, etc. In a paper by R. G. Edwards in the *British Medical Journal*, Vol. 26, pages 72 to 78, published in 1970, on "Immunology of Conception and Pregnancy", he surveys the literature regarding the possibilities of utilizing immunological methods to influence or control fertility, surveying first production of antibodies against testes or spermatozoa. Much of the literature surveyed is directed to the production of foreign antibodies which are injected into the subject (passive immunization).

Hormone antibodies have been studied for a long time and the effect of specific antisera have been recorded for many years. It is known that administration of certain antibodies during pregnancy can suppress implantation or cause fetal resorption. Several different approaches have been tried ranging from the induction of near permanent infertility in the case of agglutination of spermatozoa in the male to the disturbance of a single pregnancy by passive immunization with antibodies.

There are serious limitations to the use of passive immunization procedures for human therapy. Since the antibodies are practically produced only in non-human animals, the repeated injection of animal proteins into humans is known to produce serious reaction in many individuals.

British Patent Specification No. 1,058,828 discloses that small molecules, referred to as "serological determinant peptides", can be coupled to large protein molecules, such as cattle albumin, and the resultant conjugate then may be injected into animals for antibody production. The document lists proteins from which the serologically determinant peptides may be isolated prior to being used in the process taught, the collection including viruses and bacteria whose surface component has the characteristics of a protein, toxins and hormones having protein structure and enzymes. No specific hormone is named in the document and no utility of anti-hormone immunization is described. The patent specification references a publication entitled: "*The Specificity of Serological Reactions*", Dover Publications, Inc., New York, 1962, Chapter V, "Artificial Conjugated Antigens" by K. Landsteiner. This publication outlines various chemical methods and applies them passively to bind various toxic substances in the blood such as arsenic. Thyroxine data provided in the publication suggests that such methods may be applied to hormones without indicating the therapeutic application, the publication teaching that specific antibodies may be formed to the small molecules and these antibodies are capable of neutralizing the biological action of a large protein from which the small peptide was a part.

Recently it has been discovered that doses of certain steroids consisting of synthetic non-protein hormones ("The Pill") when administered at stated intervals usually confer protection against pregnancy for a short time (possibly a month). This medication has sometimes been found to create undesirable side effects in creating undesirable metabolic changes and sometimes changes in the blood clotting mechanisms. Moreover, the effect of each dose is of such short duration that often it is of limited application, particularly in remote areas to persons not readily instructed on proper and continuing use.

There is therefore a need for an effective safe method of creating a temporary but relatively one-time immunity against pregnancy which does not have serious side effects. There is also a need for an effective safe method of terminating a pregnancy soon after conception which does not have serious harmful side effects. Such need may be met by the neutralization of a reproductive protein which is necessary for the normal events of conception and/or gestation.

There is also a need for a means for control of various disease states or maladies caused or influenced by unusual excesses of certain polypeptides such as gastrin, angiotensin II, or somatomedian. It is believed that this invention meets this need safely and effectively.

There are also other medical needs which can be met by the present invention. It is well known to those skilled in the art of cancer treatment that certain cancers are highly resistant to the attack which would normally be made on the cancer by the immune system of a mammal in which the cancer is located. It is believed that this high resistance of certain cancers to attack by mammalian immune systems is due to the ability of the cancer to coat its external surface with materials which closely resemble certain materials endogenous to the animal in which the cancer is located, so that the animal's immune system does not detect the "foreign nature" of the cancer and hence is unable to attack it. The present invention may provide a mechanism by which the pseudo-endogenous material coating certain cancers can be stripped away, thereby facilitating attack on such cancers by the immune system of the animal in which the cancer is located.

One further use for the processes, compositions and therapeutic methods of the instant invention may be in dealing with diseases caused by agents which are not highly antigenic to mammalian immune systems. Although mammalian immune systems are extremely complex and extremely effective in dealing with most non-endogenous materials (such as bacteria and viruses) which find their way into the bodies of mammals, there are certain at least potentially dangerous non-endogenous materials which are not strongly antigenic to certain mammalian immune systems, and which thus do not provoke a sufficiently strong response from the immune system to avoid possible damage to the animal's body. The instant invention furnishes ways in which relatively non-antigenic, non-endogenous materials, for example viral proteins, can be synthetically modified to make them more strongly antigenic, thereby provoking the formation, in the body of animals, of relatively large quantities of antibodies to the non-endogenous materials, with consequent reduced risk of damage to the immune system if it thereafter is exposed to the non-endogenous materials.

SUMMARY OF THE INVENTION

As already indicated, this invention is concerned with processes for the production of modified polypeptides, with the modified polypeptides so produced, with vaccines containing the modified polypeptides and with processes for the use of the modified polypeptides.

More specifically, this invention provides an antigen for immunologically controlling biological activity in an animal by eliciting antibody formation, the antigen comprising carrier moieties biologically foreign to the animal and selected having a size sufficient to elicit antibody response non-harmful to normal body constituents following the administration thereof into the body of the animal, these carrier moieties being chemically conjugated with polypeptides having an amino acid sequence of the beta subunit of Chorionic Gonadotropin; and the conjugate produced by the conjugation effecting a constitution of two or more immunological determinants effective to elicit antibody response to the endogenous hormone, Chorionic Gonadotropin, upon the administration thereof to the animal.

This invention also provides a process for preparing an antigen for provoking the formation, in the body of an animal, of antibodies to a protein which is not endogenous or immunogenic to said animal, the process comprising activating the protein, or a peptide having a sequence corresponding to at least part of the sequence of the protein and having a sulfhydryl group thereon by treatment with an activator of the structure A shown in FIG. 9 of the accompanying drawings, where X represents a non-reacting group comprising substituted or unsubstituted phenyl or $C_{1-10}$ alkylene moieties, or a combination thereof, or an amino acid chain, so as to cause reaction of the activator with the sulfhydryl group, and treating the resultant activated protein or peptide with a carrier biologically foreign to the animal and selected having a size sufficient to elicit antibody response following the administration thereof into the body of the animal, the carrier having an amino group thereon.

The invention also provides a process for preparing an antigen for provoking the formation, in the body of an animal, of antibodies to a protein which is not endogenous or immunogenic to the animal, the process comprising activating under neutral or acid conditions a carrier not having a sulfhydryl group but having an amino group with an activator of the structure A shown in FIG. 9 of the accompanying drawings, in which X is defined above, so as to cause reaction of the activator with the amino group, the carrier being biologically foreign to the animal and selected having a size sufficient to elicit antibody response following the administration thereof into the body of the animal, and treating the resultant activated carrier with the protein, or a peptide having a sequence corresponding to at least part of the sequence of the protein, the protein or peptide having a sulfhydryl group thereon.

The invention also provides a process for preparing an isoimmunogen for controlling biological action in an animal, this process comprising activating under neutral or acid conditions a carrier not having a sulfhydryl group thereon but having an amino group with an activator of the structure B shown in FIG. 9 of the accompanying drawings, in which X is as defined above, so as to cause reaction of the activator with the amino group, the carrier being biologically foreign to the animal and selected having a size sufficient to elicit antibody response following the administration thereof into the body of the animal, and treating the resultant activated carrier with a hormone endogenous to the animal, non-hormonal polypeptide endogenous to the animal, or a synthetic or natural fragment of either, having a sulfhydryl group.

The invention also provides a process for preparing an antigen for provoking the formation in the body of an animal of antibodies to a protein which is not endogenous or immunogenic to the animal, this process comprising activating the protein, or a peptide having a sequence corresponding to at least part of the sequence of the protein and having a sulfhydryl group thereon by treatment thereof with an activator of the structure B shown in FIG. 9 of the accompanying drawings, in which X is as defined above, so as to cause the reaction of the maleiimide group of the activator with the sulfhydryl group on the protein or peptide and so as to minimize reaction of the active ester group on the activator with any amino group present on the protein or peptide, and treating the resulting activated protein or peptide at slightly alkaline pH with a carrier moiety biologically foreign to the animal and selected having a size sufficient to elicit antibody response following the administration thereof into the body of the animal.

The invention also provides a process for preparing an isoimmunogen for controlling biological activity in an animal, which process comprises activating under neutral or acid conditions a carrier not having a sulfhydryl group but having an amino group with an activator of the structure B shown in FIG. 9 of the accompanying drawings, in which X is as defined above, so as to cause reaction of the activator with the amino group, the carrier being biologically foreign to the animal and selected having a size sufficient to elicit antibody response following the administration thereof into the body of the animal thereof, and treating the resultant activated carrier with a hormone endogenous to the animal, or a synthetic or natural fragment of either having a sulfhydryl group.

The invention also provides a process for preparing an isoimmunogen for controlling biological activity in an animal which comprises reacting a carrier biologically foreign to the animal, having a size sufficient to elicit antibody response following the administration thereof into the body of the animal, and having an amino group, with an activator present as an active ester of chloro-, dichloro-, bromo- or iodo-acetic acid so as to cause reaction of the activator with the amino group, thereby converting the amino group to a group of the formula —NH.CO.T, where T is a group of the formula $CH_2Cl, CHCl_2$, $CHBr_2$, or $CH_2I$, and treating the resulting activated carrier with a sulfhydryl group-containing hormone endogenous to the animal, subunit of the hormone, peptide fragment thereof or synthetically derived peptide having a sequence analogous to at least a portion of this subunit, thereby causing reaction between the group T and the sulfhydryl group such that the carbon atom of the group T becomes bonded to the sulfur atom of the sulfhydryl group to form a thioether.

The invention also provides a process for preparing an isoimmunogen for controlling biological activity in an animal which comprises reacting a hormone endogenous to the animal, subunit of such a hormone, peptide fragment thereof or synthetically derived peptide having a sequence analogous to at least a portion of such subunit, not having a sulfhydryl group but having an amino group, with an activator present as an active ester of chloro-, dichloro-, bromo- or iodo-acetic acid so as to cause reaction of the activator with the amino group, thereby converting the amino group to a group of the —NH.CO.T where T is defined above, and treating the resultant moiety with a sulfhydryl group-containing carrier biologically foreign to the animal and having a size sufficient to elicit antibody response following the administration thereof into the body of the animal, thereby causing reaction between the group T and the sulfhydryl group such that the carbon atoms of the group T becomes bonded to the sulfur atom of the sulfhydryl group to form a thioether.

The invention also provides a process for preparing an antigen for provoking the formation, in the body of an animal, of antibodies to a protein which is not endogenous or immunogenic to the animal, this process comprising reacting a carrier biologically foreign to the animal and having an amino group with an activator present as an active ester of chloro-, dichloro-, bromo- or iodo-acetic acid so as to cause reaction of the activator with the amino group, thereby converting the amino group to a group of the formula —NH.CO.T, where T is as defined above, and treating the resulting activated carrier with the protein, or a peptide having a sequence corresponding to at least part of the sequence of the protein, the protein or peptide having a sulfhydryl group, thereby causing the reaction between the group T and the sulfhydryl group such that the carbon atom of the group T becomes bonded to the sulfur atom of the sulfhydryl group to form a thioether.

The invention also provides a process for preparing an antigen for provoking the formation, in the body of an animal, of antibodies to a protein which is not endogenous or immunogenic to the animal, this method comprising reacting the protein or a peptide having a sequence corresponding to at least part of the sequence of the protein, the protein or peptide not having a sulfhydryl group but having an amino group, with an activator present as an active ester of chloro-, dichloro-, bromo- or iodo-acetic acid so as to cause reaction of the activator with the amino group, thereby converting the amino group to a group of the formula —NH.CO.T, where T is as defined above, and treating the resulting moiety with a sulfhydryl group-containing carrier biologically foreign to the animal, thereby causing reaction between the group T and the sulfhydryl group such that the carbon atom of the group T becomes bonded to the sulfur atom of the sulfhydryl group to form a thioether.

The invention also provides a method of controlling biological activity attributable to hormone and non-hormonal protein activity in an animal, which method comprises administering to the animal an immunologically effective amount of a modified polypeptide, this modified polypeptide, consisting of a protein hormone, a non-hormonal protein, or a fragment of either which has been chemically modified outside the body of the animal, the protein hormone, non-hormonal protein or fragment having the properties of (a) in unmodified form, being non-immunogenic to the mammal and having a molecular structure similar to an endogenous protein hormone or a non-hormonal protein, the biological function of which is designed to inhibit, or a fragment of either; and (b) in modified form, causing antibodies to be formed in the body of the mammal which inhibit the biological function of the endogenous protein hormone or non-hormonal protein following administration of the modified form into the body of the mammal.

Examples of the control of biological activity attributable to hormone and non-hormonal protein activity which can be achieved by this method are as follows:

(1) control of Zollinger-Ellison Syndrome using modified polypeptides derived from gastrin, or fragments thereof;

(2) control of hypertension using modified polypeptides derived from angiotension I or II, or fragments thereof;

(3) control of elevated levels of growth hormone and/or somatomedian using modified polypeptides derived from growth hormone, somatomedian or fragments of either of these hormones;

(4) control of kidney stones using modified polypeptides derived from parathyroid hormone or fragments thereof;

(5) control of hyperinsulinoma using modified polypeptide derived from insulin, glucagon or fragments of either of these hormones;

(6) control of hyperthyroidism using modified polypeptides derived from thyroid stimulating hormone or fragments thereof; and (7) control of irritable bowel syndrome using modified polypeptides derived from secretin or a fragment thereof.

The invention also provides a vaccine for provoking the formation, in the body of an animal, of antibodies to a protein which is not substantially immunogenic to the animal, this vaccine comprising a modified polypeptide of the invention derived from the protein or a fragment thereof together with a vehicle, this vehicle comprising a mixture of mannide monooleate with Squalane and/or Squalene.

The invention also provides a modified polypeptide for provoking the formation, in the body of an animal, of antibodies to a protein, the modified polypeptide comprising a linear polymer of polypeptide fragments, each of the fragments, in its monomeric form, being substantially non-immunogenic to the animal and having a molecular structure similar to a fragment of the protein to which antibodies are to be provoked, the linear polymer, after administration into the body of the animal, having a greater capacity to provoke the formation of the antibodies than the protein, the linear polymer being substantially free of non-linear polymers of the fragments.

In another aspect, this invention provides a method for producing a modified polypeptide for provoking the formation, in the body of an animal, of antibodies to a protein which is substantially non-immunogenic to the animal, the method being characterized by:

(a) procuring a first peptide having a molecular structure similar to a fragment of the protein, the first peptide not having an unblocked thiol group and having an unblocked amino group only at its N-terminal but no other unblocked amino group;

(b) reacting the first peptide with an amino group activating agent, thereby producing an activated amino group at the N-terminal of the first peptide;

(c) reacting the activated first peptide with a second peptide having a molecular structure similar to a fragment of the protein, the second peptide having a C-terminal cysteine bearing an unblocked thiol group but not having any other unblocked thiol groups, thereby coupling the N-terminal of the first peptide to the C-terminal of the second peptide;

(d) reacting the resultant compound in a form having an unblocked amino group at its N-terminal but no other unblocked amino groups, and no unblocked thiol group, with an amino-group activating agent, thereby producing an activated amino-group at the N-terminal of the resultant compound;

(e) reacting the activated compound produced in step (d) with a further peptide having a molecular structure similar to a fragment of the protein, this further peptide having a C-terminal cysteine bearing an unblocked thiol group, but not having any other unblocked thiol groups, thereby coupling the activated N-terminal of the reactivated compound produced in step (d) to the C-terminal of the further peptide; and (f) repeating steps (d) and (e) until the desired polymer length has been achieved.

In another aspect, this invention provides an antigen for provoking the formation, in the body of an animal, of antibodies to a protein which is not endogenous nor substantially immunogenic to the animal, characterized in that the antigen comprises the protein, or a peptide having a sequence corresponding to at least part of the sequence of the protein, which protein or peptide has been chemically modified outside the body of the animal, the antigen having a greater capacity to provoke the formation of the antibodies than the protein in its unmodified form.

In another aspect, this invention provides a process for preparing an antigen of the invention, which process is characterized by:

procuring a protein which is not endogenous or immunogenic to the animal, or the peptide having a sequence corresponding to at least part of the sequence of the protein; and chemically modifying the protein or peptide outside the body of the animal, thereby producing the antigen of the invention.

In another aspect, this invention provides a modified antigen for use in fertility control in an animal characterized in that it comprises an antigen derived from the zona pellucida or from sperm, or a peptide having a sequence corresponding to at least part of the sequence of such a zona pellucida or sperm antigen, which antigen or peptide has been chemically modified outside the body of the animal, the modified antigen, after administration into the body of the animal, having a greater capacity to provoke the formation of antibodies than the unmodified antigen from which it is derived.

This invention also provides a peptide having an amino acid sequence corresponding to the C-terminal sequence of the beta subunit of human chorionic gonadotropin, the peptide comprising from 20 to 45 amino acid residues.

Finally, this invention provides a method of controlling fertility in an animal which comprises administering to the animal an immunologically effective amount of a modified polypeptide consisting of FSH, HCG, LH, HPL, prolactin, relaxin, an antigen derived from the zona pellucida or from sperm, or a fragment of any one of these hormones, which has been chemically modified outside the body of the animal, the hormone or fragment having the properties of (a) in unmodified form, being substantially non-immunogenic to the animal; and (b) in modified form, causing antibodies to be formed in the body of the animal, these antibodies being capable of inhibiting the biological function of the hormone from which the modified polypeptide is derived.

BRIEF DESCRIPTION OF THE DRAWINGS

FIG. 1 is a chart describing the results of mating four baboons three times following the administration thereto of a fertility controlling antigen according to the invention;

DETAILED DESCRIPTION OF THE INVENTION

Figure 2:
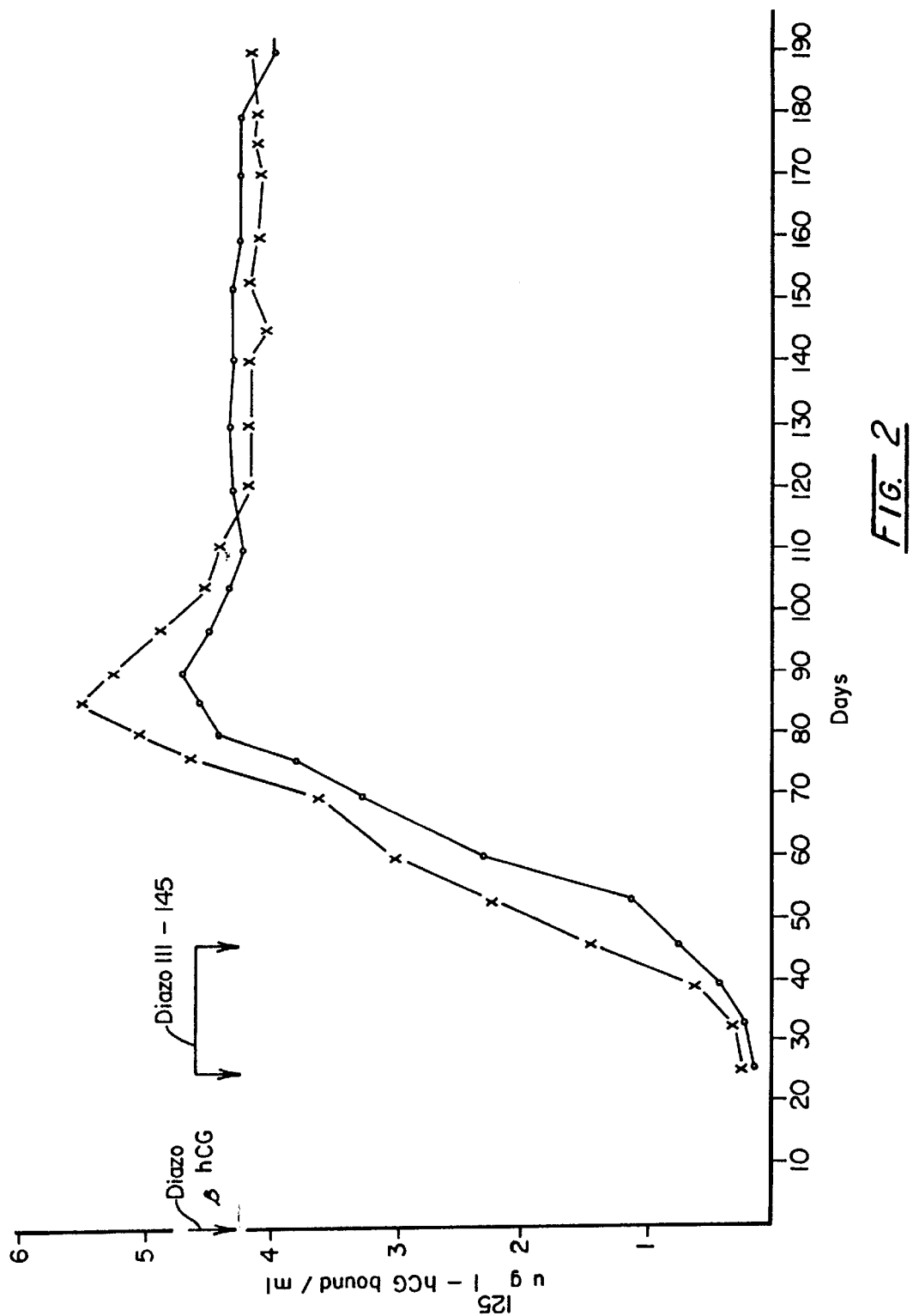
FIG. 2 shows two plots illustrating the antifertility antibody levels maintained within two baboons following the administration of antigens thereto formulated in accordance with the invention.

As will be apparent from the foregoing Summary of the Invention, the invention is of extremely broad scope and is applicable to modification of a large number of proteins, both endogenous and non-endogenous, and modifications of fragments of such proteins. In view of the complexity of the invention, and the fact that many aspects of the invention, such as the particular preferred modification techniques, do not vary greatly from one protein or fragment to another, the following plan will be adopted in this Detailed Description both for brevity and for clarity. Following a general introduction, the various aspects of this invention will be discussed under three main headings. Firstly, this description will discuss the selection of the protein or fragment to be used to achieve a desired effect in a mammal. Secondly, the techniques used to modify the peptides in order to increase the antigenicity thereof will be discussed. Finally, the discussion will focus on the modes of administration of the modified polypeptides, including discussion of the vehicles used to carry such modified polypeptides and certain additives which may be useful in conjunction with the modified polypeptides. This section of the discussion will also discuss appropriate modes of administration of the modified polypeptides.

One important aspect of this invention relates to the use of modified polypeptides in actively immunizing an animal, particularly a mammal, against the biological action of endogenous unmodified hormone and/or non-hormonal natural protein. The state of immunity (in the sense of causing the immune system of the animal to which the modified polypeptide is administered to react against the larger protein endogenous to the animal, whereas of course normally the immune system will not react to endogenous proteins) arises because of the creation of antibodies which act against the antigenic modified polypeptide and its endogenous, unmodified counterpart which is neutralized (rendered biologically ineffectual) as a result of the existence of the antibodies. The immunity may take place because of the inability of the antibody to distinguish between the modified polypeptide and the naturally existing protein, but it is uncertain that this is in fact the situation. In effect, the invention provides, in one aspect, for the isoimmunization of a primate or other mammal.

For example, one important aspect of this invention, which is discussed in much more detail below, relates to the modification of protein reproductive hormones by adding certain numbers of foreign moieties (or carriers) to each hormone molecule, or hormone or fragment, or polymerization of fragments of the relevant hormone. The modification must be sufficient to cause the body to create antibodies to the modified hormone which will neutralize or inhibit the biological activity of the natural hormone produced by the body. Thus, the modified hormones become antigenic and cause the production of antibodies which disrupt the natural processes of conception and/or gestation. The term "protein reproductive hormones" includes those hormones essential to the natural events of the reproductive process, including hormones associated with the production of sperm in the male as well as those associated with the reproductive function of the female.

The immunochemical control (isoimmunization process), as already noted, neutralizes the naturally occurring hormone or the entity biologically analogous thereto. As a consequence, the hormone or entity is no longer available as would normally be the case, for example, in the stimulation of some activity of a target tissue. Conversely, the neutralization of the biological activity of the hormone or analogous entity may serve to take away an inhibitory action which it otherwise might assert.

As indicated above, a theory leading to this invention was that the chemical modification of an essential reproductive hormone would alter it such that it would exhibit antigenic properties so that when injected into an animal (including humans) it would cause the formation of antibodies which in turn would not only bind to the injected modified hormone but also to the natural unmodified endogenous hormone as well. With this theory in mind, reproductive hormones of various species were modified and tested in baboons. The results illustrated that modified hormones of unrelated species do not produce the desired results, whereas modified hormones of the same or closely related species do produce the desired results. It will accordingly be clear that the polypeptide to be modified should be so related to the endogenous hormone or non-hormonal protein as to be either from the same animal species or be the immunological equivalent thereof as modified.

Additional experiments were conducted to test the validity of this concept in humans, i.e. modified human reproductive hormones were injected into humans. Collectively, the results prove the conclusion drawn from the experiments with the baboons, namely, that isoantigenic immunization using modified human reproductive hormones does produce contraception or interruption of gestation. Detailed examples which follow illustrate this result.

It is known that fragments of endogenous hormones exhibit essentially no antigenic properties. However, should a large enough fragment of an endogenous hormone be slightly modified as indicated above, then antibodies will be formed which will react in the same way as if the modification is on a whole hormone, provided the large fragment is sufficiently distinctive in chemical and physical make-up as to be recognized as a specific part of the whole.

Whether the hormone or specific fragment thereof is naturally occurring or is a synthetic product is clearly immaterial. A synthetic hormone molecule will perform the same function as the naturally occurring one, being equivalent for the purpose of this invention. In this connection, it will be noted that certain natural substances with which this invention is concerned possess carbohydrate moieties attached at certain sites thereon whereas the corresponding synthetic polypeptides do not. Nevertheless, for the purpose of the instant specification and claims, the synthetic and natural polypeptides are treated as equivalents and both are intended to be embraced by this invention. Reference in the above regard is made to Table 3 herein as read in conjection with Example XXIX.

Thus, where the word "hormone" or "hormone molecule" is used herein, the word "synthetic" may be added before "hormone" without changing the meaning of the discussion. Similarly, the word "fragment" may be inserted after "hormone" or "molecule" without changing the meaning, whether or not "synthetic" has been inserted before "hormone".

The present invention is, however, not limited to modification of protein reproductive hormones, and numerous further examples of modification of the hormones and non-hormonal endogenous proteins will be given below. Moreover, not merely is the invention applicable to modification of non-reproductive endogenous proteins, the invention also is applicable to modification of non-endogenous proteins. Although most non-endogenous proteins are to some extent immunogenic, the immunogenicity of certain non-endogenous proteins, for example some viruses, is so low that the body of a mammal into which the virus enters may fail to produce antibodies to the weakly immunogenic non-endogenous protein in such quantities as to effectively remove the deleterious non-endogenous protein from the animal's system. Accordingly, the modification techniques of this invention may be employed to increase the immunogenicity of non-endogenous proteins in order to ensure a more satisfactory response from the immune system of the mammal, thereby of course rendering the mammal much less prone to the deleterious effects of the unmodified non-endogenous protein if the immune system is later challenged with such non-endogenous protein.

Whether the relevant hormone, non-hormonal protein, non-endogenous protein or specific fragment thereof which is modified by the techniques of the instant invention is naturally occurring or is a synthetic product is clearly immaterial. A synthetic protein molecule or peptide will perform the same function as a naturally occurring one, inasmuch as the body will react in an equivalent antigenic manner to both. It has accordingly been discovered by virtue of this invention that it is possible to interfere with or treat various disease states or medical problems which are caused or influenced by certain polypeptides by active immunization of a male or female animal by the production and use of antigens formed by administration of modified polypeptides. The modification of the polypeptides forms antigens which are then administered into an animal in which immunization is desired.

The invention is useful for both the human and other animals. Similarly, although the main focus of the fertility control aspects of the invention discussed in more detail below is on treating females, such techniques may be applicable to males e.g. modified polypeptides based upon FSH, its beta subunit and fragments thereof, together with modified polypeptides based upon sperm antigens or relaxin. Such immunization represents an effective fertility control technique, provided no physiological consequences are encountered which may be found to react adversely to the performance of other body constituents.

It should be noted that the term "endogenous" is used herein to denote a protein which is native to the species to be treated, regardless of whether the relevant protein, fragment or antigen is endogenous to the particular individual animal being treated. Thus, for example, for purposes of this application, a porcine sperm antigen is regarded as being endogenous to a sow even though obviously such a sperm antigen will not normally be present in the body of a sow.

As already noted, the modified polypeptides of the invention which are derived from endogenous protein hormones, non-hormonal proteins or fragments thereof, provoke, when administered into the bodies of appropriate mammals, antibodies to the endogenous proteins from which the modified polypeptides are derived. Consequently, not only can such modified polypeptides be used to influence the biological activity in a mammal to which they are administered by generating antibodies to an endogenous protein in the mammal, but the modified polypeptides of the invention (whether prepared by coupling the endogenous protein or fragment thereof to a carrier, or by coupling a plurality of such fragments together) can also be used to generate antisera by introducing the modified polypeptides into the body of a mammal, thereby provoking the formation, in the mammal, of antibodies to the "endogenous protein"; note that in such a method, since the modified polypeptide need not be introduced into the same mammal, or even a mammal of the same species, as the animal from which it is derived or, in the case of a modified polypeptide based upon a synthetic fragment, the mammal whose protein it mimics, the so-called "endogenous protein" used in this method need not be endogenous to the mammal in which the antibodies are raised.

Following the raising of the antibodies in the mammal, some of the antibodies are recovered from the mammal, using conventional techniques which will be familiar to those skilled in the art of immunology. Techniques generating monoclonal antibodies may also be used to generate the desired antibodies. The antibodies thus generated can then be used for a variety of purposes. For example, such antibodies may be used for assaying the quantity of an endogenous protein in a mammal by bringing at least some of the recovered antibodies into contact with body tissue or body fluid from the mammal and observing the formation or non-formation of the reaction process between the recovered antibody and the endogenous protein indicative of the presence or absence of the endogenous protein in the body tissue or body fluid assayed. If, in this method, the endogenous protein assayed is one associated with pregnancy, this assay method can function as a pregnancy test. If, on the other hand, the endogenous protein assayed is one the presence or absence of which is associated with reduced fertility or infertility in the mammal from which the body tissue or body fluid is derived, the assay can function as a test for reduced fertility or infertility in such a mammal.

SELECTION OF POLYPEPTIDE FOR MODIFICATION

As already indicated, the present invention is applicable to almost any hormonal or other protein related activity in a mammal, and to activities, such as infections, in mammals caused by non-endogenous but relatively weakly immunogenic protein agents, such as viral proteins. Examples of natural hormones and natural non-hormonal proteins which may be modified according to this invention include Follicle Stimulating Hormone (FSH), Luteinizing Hormone (LH), Luteinizing Hormone Releasing Hormone (LH-RH), relaxin, Chorionic Gonadotropin (CG), e.g. Human Chorionic Gonadotropin (HCG), Placental Lactogen, e.g. Human Placental Lactogen (HPL), Prolactin, e.g. Human Prolactin (all of which are proteinaceous reproductive hormones), Gastrin, angiotension I and II, growth hormone, somatomedian, parathyroid hormone, insulin, glucagon, thyroid stimulating hormone (TSH), secretin, and other polypeptides which could adversely affect body function.

Despite the very wide range of proteins to which the techniques of the present invention can be applied, there are certain considerations which should always be borne in mind when considering the selection of an appropriate polypeptide for modification by the techniques of the instant invention. Firstly, it is of course necessary to determine which hormone or combination of hormones or other protein is responsible for the condition or problem which it is desired to treat. However, in many cases this will still leave one with a large number of possible proteins which could be modified by the techniques of the instant invention. For example, if one wishes to use the instant invention to render a female mammal infertile, one can approach the problem by modifying FSH, LH, LH-RH, CG, PL, relaxin or a variety of other protein hormones which are known to be involved in the female mammalian reproductive system. One important consideration which should always be borne in mind in choosing a polypeptide for modification by the instant invention is the problem of cross-reactivity. As well known to those skilled in the field of immunology, it is not uncommon to find that antibodies intended to react with one protein (the "target" protein) also react to a significant extent with other, non-target proteins. This is a serious problem, since it may cause the administration of a modified polypeptide intended to provoke the formation of antibodies to one specific natural hormone to cause the generation of antibodies to one or more other hormones, which it is not desired to effect. In some cases, the reactions with the non-target proteins may cause damage to essential body functions. Accordingly, so far as possible the peptide selected for modification by the instant invention should be chosen so that the modified polypeptide will provoke, in the body of the mammal to be treated, the formation of antibodies which are highly specific to the target protein.

Although in some cases, especially where the target protein is relatively small (for example LH-RH or angiotension I or II), it may be in practice essential to modify the whole target protein, since a fragment comprising less than the whole target protein, will, even when modified by the instant techniques, fail to provoke sufficient antigens to the target protein, in general, especially when dealing with relatively complex target proteins such as insulin or HCG, the use of a fragment of the target protein rather than the intact target protein is recommended for use in modification according to the instant invention. As already mentioned, it is well recognized by those skilled in immunology (see e.g. W. R. Jones, "Immunological Fertility Regulation", Blackwell Scientific Publications, Victoria, Australia (1982) (the entire disclosure of this work is herein incorporated by reference), pages 11 et. seq. that one of the greatest potential hazards of a vaccine, especially a contraceptive vaccine, is cross-reactivity with non-target antigens, producing what is essentially an artificially-induced autoimmune disease capable of causing immunopathological lesions in, and/or loss of function of, the tissues carrying the cross-reactive antigens. Two possible mechanisms for such cross-reactivity are:

(a) presence of shared antigenic determinants; a complex protein may contain components (amino-acid sequences) identical to those present in non-target antigens; and (b) steric overlap between non-identical but structurally related parts of the target and non-target antigens. Obviously, the threats posed by both these modes of cross-reactivity may be lessened by using, in the modified polypeptides of the invention, a fragment of a complex protein rather than the whole protein. Since the fragment has a simpler structure than the protein from which it is derived, there is less chance of shared antigenic determinants or steric overlap with non-target antigens. In particular, cross-reactions cannot be avoided by using fragments derived from a portion of the target protein which is not similar in sequence to the non-target but cross-reactive antigen. To take one specific example, one of the major problems in provoking antibodies to HCG is cross-reactivity of HCG antibodies with LH, this cross-reactivity being at least largely due to virtual identity of amino acid sequence between LH and the 1–110 amino acid sequence of the beta subunit of HCG. Accordingly, when it is desired to form an HCG-derived modified polypeptide of the invention, the fragment used is preferably one having a molecular structure similar to part or all of the 111–145 sequence of the beta subunit of HCG, since it is only this 111–145 sequence of beta-HCG which differs significantly from the corresponding sequence of LH.

Thus, in most cases the polypeptide modified by the techniques of the instant invention is preferably a fragment of the target protein rather than the intact target protein. More accurately, one should use as the polypeptide to be modified by the techniques of the invention a fragment having a molecular structure similar to a fragment of the target protein. In saying that the fragment has a molecular structure similar to a fragment of the target protein, it is not necessarily implied that the entire amino acid sequence of the fragment must correspond exactly to part of the sequence of the target protein; for example, in certain cases some substitution of amino acids may be possible without effecting the immunogenic character of the fragment. For example, the aforementioned U.S. Pat. No. 4,302,386 describes a polypeptide, designated Structure (IX) (which is also discussed in detail below), which is notionally derived from the beta subunit of HCG but in which the cysteine residue at the 110-position is replaced by alpha-aminobutyric acid. Furthermore, it is shown in the examples below that although the natural form of the beta subunit of HCG contains a number of carbohydrate residues attached to the amino-acid chain, synthetic peptides corresponding in sequence to the relevant parts of the HCG sequence, but lacking such carbohydrate residues, can be modified by the techniques of the instant invention and give good results.

Although species specificity is of course a consideration in any immunological process, I do not exclude the possibility of the fragments modified by the instant processes may actually be derived from a protein of a different species of mammal than the mammal to which they are to be administered, since many proteins are either identical between species or differ from one another so little in amino acid sequence that considerable cross-reactivity exists between antibodies to the corresponding proteins of the two species. For example, as mentioned below, zona pellucida enzymes from a pig will, when injected into humans, produce antibodies which display considerable activity against human zona antigens. Accordingly, for example, if one wishes to form a modified polypeptide for provoking the formation of antibodies, in humans, to zona pellucida antigens, appropriate polypeptide fragments may be prepared from the zona pellucida antigens of pigs. Also, the fragments modified by the instant processes may incorporate sequences of amino acids having no counterpart in the sequence of the protein from which the fragment is notionally derived. Again, for example, it is shown below that one may use in the instant processes certain polypeptide fragments, designated Structures (IV), (VIII), (IX), (X) and (XIV) which are notionally derived from the beta subunit of HCG but which incorporate spacer sequences comprising multiple proline residues.

Of course, one should be cautious when using sequences not exactly corresponding to portions of the target protein. For example, the protein relaxin is known to be highly species specific and accordingly it is not recommended that fragments of non-human relaxin proteins be modified by the instant methods and injected into humans to provoke the formation of anti-relaxin-antibodies in humans.

In choosing an appropriate polypeptide for modification according to the instant invention, amino-acid sequence is, however, not the only factor which has to be considered; it is also necessary to pay close attention to the conformation, that is to say the physical shape, of the protein or fragment selected for modification relative to the natural conformation of the target protein. It is well known to those skilled in the art of immunology that the conformation or shape of an antigen is an important factor in allowing recognition of the antigen by an antibody. Accordingly, if a polypeptide modified according to the instant invention does not retain the conformation of the relevant part of the target protein, it is likely that the antibodies provoked by injection of the modified polypeptide into a mammal will not display optimum activity against the natural target protein. For example, a peptide having the same sequence as part of the target protein will probably not work very well if, because of the absence of other parts of the sequence of the target protein which affect the positioning of the crucial antigenic determinant in the natural target protein, the fragment used to prepare the modified polypeptide of the invention adopts a conformation very different from the conformation of the same amino acid sequence in the target protein. Similarly, because of the way in which the chain of a complex target protein will normally be folded, the antigen-antibody binding reaction may rely upon recognition of two or more amino acid sequences which are widely separated along the chain of the target protein but lie, in the natural conformation of the target protein, closely adjacent one another in space. All these considerations may enter into the question of what is the most appropriate polypeptide to use in the instant invention.

As those skilled in the art are aware, one major factor effecting the conformation, and hence the antigenic properties and antigenic determinants, of complex proteins is the presence of cysteine residues and disulfide bridges in such proteins. It is well known to those skilled in the art that, in many natural proteins containing cysteine residues, these residues are not present in their thiol form containing a free —SH group; instead, pairs of cysteine residues are linked by means of disulfide bridges to form cystine. Such disulfide bridges are very important in determining the conformation of the protein. In most cases, the disulfide bridges present in the natural form of the protein are easily reduced to thiol groups by means of mild reducing agents under conditions which leave the remaining parts of the protein molecule unchanged. Such breaking of disulfide bridges causes major changes in the conformation of the protein even though no disturbance of the amino acid sequence occurs. In particular, the twelve cysteine residues present in the beta subunit of HCG are, in the natural form of the subunit, coupled together to form six disulfide bridges, so that the natural form of the protein has no free thiol groups. (It should be noted that the exact manner in which the twelve cysteine residues are interconnected to form the six disulfide bridges is not at present known, although the location of three of the six bridges has been made with reasonable certainty.)

The generation of free thiol groups by reduction of disulfide bridges in naturally occurring forms of proteins may affect the cross-reactivity of the antibodies produced when a modified polypeptide derived from the protein or a fragment thereof is injected into an animal. As already mentioned, an antibody frequently recognizes its corresponding antigen not only by the amino acid sequence in the antigen but also by the conformation of the antigen. Accordingly, an antibody which binds very strongly to a protein or a peptide in its natural conformation may bind much less strongly, if at all, to the same protein or polypeptide after its conformation has been drastically altered by breaking disulfide bridges therein.

Accordingly, the breaking of disulfide bridges in proteins or other polypeptides may provide a basis for reducing the cross-reactivity between antibodies to antigens having the same amino acid sequence along parts of the molecule. For example, it has been pointed out above that cross-reaction is frequently encountered between antibodies to beta-HCG and HLH because the first 110 residues in the beta-HCG and HLH sequence are virtually identical in the natural forms of the two molecules, thus the conformations are also presumably very similar. It has been suggested above that one means of producing in an animal antibodies to beta-HCG which do not substantially cross-react with HLH is to supply to the animal an antigen of the invention derived from a polypeptide which contains all or part of the residues 111–145 of beta-HCG but which lacks all or substantially all of the residues 1–110 of beta-HCG. In effect, this approach avoids antibody cross-reaction with HLH by chemically removing from the modified polypeptide of the invention the sequence of residues which is common to beta-HCG and HLH. As an alternative approach, by cleaving the appropriate number of disulfide bridges in the natural form of beta-HCG, it may be possible to so alter the conformation of residues 1–110 thereof that the antibodies formed when a modified polypeptide of the invention based upon this altered-conformation beta-HCG is administered to an animal will no longer cross-react significantly with HLH. In other words, instead of chemically severing the common sequence of residues from beta-HCG in order to prevent cross-reaction, it may be possible to leave this common sequence of residues in the beta-HCG but to so alter the conformation of this common sequence that, to an antibody, the altered-conformation common sequence does not "look" like the natural form of the common sequence, so that an antibody which recognizes the altered-conformation common sequence will not recognize the natural-conformation common sequence in HLH. Moreover, once the natural conformation of the sequence of residues 1–110 has been destroyed by breaking the disulfide bridges, this common sequence will probably assume the helical conformation common in polypeptides lacking disulfide bridges, so that this part of the beta-HCG will not be strongly immunogenic and most of the antibodies formed by an antigen of the invention based upon the altered-conformation beta-HCG will be antibodies to the sequence 111–145 which is not common with HLH. Obviously, cross-reactivity between antibodies to other pairs of hormones may similarly be destroyed by altering the conformation of portions of the two proteins which are similar and hence will otherwise promote antigen cross-reactivity.

Appropriate polypeptides derived from certain important proteins and suitable for modification by the instant processes will now be discussed in more detail. However, it is stressed that the following specific applications of the instant processes are not limitative, since as already explained the present invention is applicable to modification of polypeptides derived from a very wide variety of both endogenous and non-endogenous proteins.

REPRODUCTIVE HORMONES

As is well known to those skilled in the art, the hormone system affecting reproduction in both male and female mammals is extremely complex, and the instant invention may be used to control fertility in both males and females by interference with a very wide variety of hormones. At present, the preferred polypeptides for modification by the instant processes are polypeptides derived from CG, polypeptides derived from zona pellucida or sperm antigens or placental antigens, and polypeptides derived from relaxin. Each of these three groups of polypeptides will now be discussed individually.

CHORIONIC GONADOTROPIN

The hormone, Chorionic Gonadotropin (CG) has been the subject of extensive investigation, it being demonstrated in 1927 that the blood and urine of pregnant women contained a gonad-stimulating substance which, when injected into laboratory animals, produced marked gonadal growth. Later, investigators demonstrated with certainty that the Placental Chorionic villi, as opposed to the pituitary, were the source of this hormone. Thus, the name Chorionic Gonadotropin or, in the case of humans, Human Chorionic Gonadotropin (HCG) was given to this hormone of pregnancy. During the more recent past, a broadened variety of studies have been conducted to describe levels of HCG in normal and abnormal physiological states, indicating its role in maintaining pregnancy. The studies have shown the hormone's ability to induce ovulation and to stimulate corpus luteum function, and evidence has been evoked for showing its ability to suppress lymphocyte action. The immunological properties of the HCG molecule also have been studied widely. Cross-reaction of antibodies to HCG with human pituitary Luteinizing Hormone (LH), and vice-versa, has been extensively documented, see for example:

Paul, W. E. & Ross, F. T., "Immunologic Cross Reaction Between HCG and Human Pituitary Gonadotropin", *Endocrinology,* 75, 352–358 (1964);

Flux, D. X. & Li, C. H., "Immunological Cross Reaction Among Gonadotropins", *Acta Endocrinologic,* 48, 61–72 (1965);

Bagshawe, K. D.; Orr, A. H. & Godden, J., "Cross-Reaction in Radio-Immunoassay between HCG and Plasma from Various Species", *Journal of Endocrinology,* 42, 513–518 (1968);

Franchimont, P., "Study on the Cross-Reaction between HCG and Pituitary LH", *European Journal of Clinical Investigation,* 1, 65–68 (1970);

Dorner, M.; Brossmer, R.; Hilgenfeldt, U. and Trude, E, "Immunological reactions of Antibodies to HCG with HCG and its chemical derivatives in Structure-Activity Relationships of Proteins and Polypeptide Hormones", (ed. M. Margoulies & F. C. Greenwood), pp 539, 541 *Amsterdam: Excerpta Medica Foundation* (1972);

Further, these cross-reactions have been used to perform immunoassays for both CG and LH hormones. See:

Midgley, A. R. Jr., "Radioimmunoassay: a method for HCG and LH", *Endocrinology,* 79, 10–16 (1966);

Crosignani, P. G.; Polvani, F. & Saracci, R., "Characteristics of a radioimmunoassay for HCG-LH; in Protein and Polypeptide Hormones" (ed. M. Margoulies) pp. 409, 411 *Amsterdam: Excerpta Medica Foundation* (1969);

Isojima, S.; Nake, O.; Kojama, K. & Adachi, H., "Rapid radioimmunoassay of human L. H. using polymerized anti-human HCG as immunoadsorbent", *Journal of Clinical Endocrinology and Metabolism,* 31, 693–699 (1970).

Although the entire CG hormone or a subunit thereof, for example the beta subunit, may be modified by the instant processes, in general it is preferred to use a polypeptide corresponding to only a fragment of the beta subunit. More specifically, as already noted there is a large portion of the beta subunit of CG which is almost identical to the corresponding beta subunit of LH, so that it is desirable to use a fragment corresponding to a portion of the 111–145 sequence of the beta subunit of CG which is not common to LH, thereby avoiding the cross-reactivity of CG and LH antibodies already discussed above. Thus, an immunological reaction against the hormone CG can be achieved without causing undesirable immune reactions to the naturally occurring body constituent LH. Synthetic polypeptides corresponding to the desired fragments of CG offer enhanced practicality both from the standpoint of production costs and the high degree of purity needed for commercial use in a contraceptive maxim.

Subunits and fragments of the proteinaceous reproductive hormones include the beta subunit of natural Follicle Stimulating Hormone, the beta subunit of natural Human Chorionic Gonadotropin, fragments including, inter alia, a 20–30 or 30–39 amino acid peptide consisting of the C-terminal residues of natural Human Chorionic Gonadotropin beta subunit, as well as specific unique fragments of natural Human Prolactin and natural Human Placental Lactogen, which may bear little resemblance to analogous portions of other protein hormones. Further with respect to the type of novel chemical entities with which this invention is concerned, one may note for instance the chemical configuration of the beta subunit of HCG. That structure is as follows:

Structure (I)

Ser-Lys-Glu-Pro-Leu-Arg-Pro-Arg-Cys-Arg-Pro-

Ile-Asn-Ala-Thr-Leu-Ala-Val-Glu-Lys-Glu-Gly-

Cys-Pro-Val-Cys-Ile-Thr-Val-Asn-Thr-Thr-Ile-

Cys-Ala-Gly-Try-Cys-Pro-Thr-Met-Thr-Arg-Val-

Leu-Gln-Gly-Val-Leu-Pro-Ala-Leu-Pro-Gln-Val-

Val-Cys-Asn-Try-Arg-Asp-Val-Arg-Phe-Glu-Ser-

Ile-Arg-Leu-Pro-Gly-Cys-Pro-Arg-Gly-Val-Asn-

Pro-Val-Val-Ser-Try-Ala-Val-Ala-Leu-Ser-Cys-

Gln-Cys-Ala-Leu-Cys-Arg-Arg-Ser-Thr-Thr-Asp-

Cys-Gly-Gly-Pro-Lys-Asp-His-Pro-Leu-Thr-Cys-

Asp-Asp-Pro-Arg-Phe-Gln-Asn-Ser-Ser-Ser-Ser-

Lys-Ala-Pro-Pro-Pro-Ser-Leu-Pro-Ser-Pro-Ser-

Arg-Leu-Pro-Gly-Pro-Ser-Asp-Thr-Pro-Ile-Leu-

Pro-Gln

For specificity of antibody action it is necessary that distinctive peptides be isolated or prepared that contain molecular structures completely or substantially completely different from the other hormones. The beta subunit of HCG possesses a specific chain or chains of amino acid moieties which differ either completely or essentially from the polypeptide chain of Human Luteinizing Hormone. These chains or fragments, when conjugated with a carrier, represent an additional aspect of this invention. Accordingly, the polypeptide Structures (II) and (III) [C-terminal portions of structure I]

Structure (II)

Asp-Asp-Pro-Arg-Phe-Gln-Asp-Ser-Ser-Ser-Ser-

Lys-Ala-Pro-Pro-Pro-Ser-Leu-Pro-Ser-Pro-Ser-

Arg-Leu-Pro-Gly-Peo-Ser-Asp-Thr-Pro-Ile-Leu-

Pro-Gln

Structure (III)

Gln-Asp-Ser-Ser-Ser-Ser-Lys-Ala-Pro-Pro-Pro-

Ser-Leu-Pro-Ser-Pro-Ser-Arg-Leu-Gly-Pro-Ser-

Asp-Thr-Pro-Ile-Leu-Pro-Gln whether obtained by purely synthetic methods or by enzymatic degradation from the natural or parent polypeptide, [Carlson et al., *J. Biological Chemistry,* 284 (19), 6810, (1973)] when modified according to this invention, similarly provide materials with antigenic properties sufficient to provide the desired immunological response.

The beta subunit set forth at structure (I) is seen to represent a chemical sequence of 145 amino acid components. This structure has a high degree of structural homology with the corresponding subunit of Luteinizing Hormone (LH) to the extent of the initial 110 amino acid components. As indicated above, it may be found desirable, therefore to evoke a high specificity to the Chorionic Gonadotropin hormone or an analogous entity through the use of fragments analogous to the C-terminal, 111–145 amino acid sequence of the subunit. Structure (II) above may be observed to represent just that sequence. Structure (III) is slightly shorter, representing the 116–145 amino acid positions within the subunit sequence.

Further polypeptide chains useful for modification by the instant processes to promote antibody build-up against natural CG include the following structures labeled Structures (IV)–(XIV). When modified by the instant processes, these polypeptide provide immunogenic activity against HCG. All of these polypeptides are considered fragments of HCG by virtue of their substantial resemblance to the chemical configuration of the natural hormone and the immunological response provided there provided by them when modified by the instant processes.

Structure (IV)

Cys-Pro-Pro-Pro-Pro-Pro-Pro-Ser-Asp-Thr-Pro-
Ile-Leu-Pro-Gln

Structure (V)

Asp-Asp-Pro-Arg-Phe-Gln-Asp-Ser-Pro-Pro-Pro-
Pro-Pro-Pro-Cys

Structure (VI)

Phe-Gln-Asp-Ser-Ser-Ser-Ser-Lys-Ala-Pro-Pro-
Pro-Ser-Leu-Pro-Ser-Pro-Ser-Arg-Leu-Pro-Gly-
Pro-Ser-Asp-Thr-Pro-Ile-Leu-Pro-Gln

Structure (VII)

Asp-Asp-Pro-Arg-Phe-Gln-Asp-Ser-Ser-Ser-Ser-
Lys-Ala-Pro-Pro-Pro-Ser-Leu-Pro-Ser

Structure (VIII)

Asp-Asp-Pro-Arg-Phe-Gln-Asp-Ser-Pro-Pro-Pro-
Cys-Pro-Pro-Pro-Ser-Asp-Thr-Pro-Ile-Leu-Pro-
Gln

Structure (VIIIa)

Asp-Asp-Pro-Arg-Phe-Gln-Asp-Ser-Pro-Pro-Pro-
Pro-Pro-Pro-Cys-Pro-Pro-Pro-Pro-Pro-Pro-Ser-
Asp-Thr-Pro-Ile-Leu-Pro-Gln

Structure (IX)

Asp-His-Pro-Leu-Thr-Aba-Asp-Asp-Pro-Arg-Phe-
Gln-Asp-Ser-Ser-Ser-Ser-Lys-Ala-Pro-Pro-Pro-
Ser-Leu-Pro-Ser-Pro-Ser-Arg-Leu-Pro-Gly-Pro-
Ser-Asp-Thr-Pro-Ile-Leu-Pro-Gln-Pro-Pro-Pro-
Pro-Pro-Pro-Cys

Structure (X)

-continued

Asp-Asp-Pro-Arg-Phe-Gln-Asp-Ser-Ser-Ser-Ser-
Lys-Ala-Pro-Pro-Pro-Ser-Leu-Pro-Ser-Pro-Ser-
Arg-Leu-Pro-Gly-Pro-Ser-Asp-Thr-Pro-Ile-Leu-
Pro-Gln-Pro-Pro-Pro-Pro-Pro-Pro-Cys

Structure (XI)

Asp-Asp-Pro-Arg-Phe-Gln-Asp-Ser-Ser-Ser-Ser-
Lys-Ala-Pro-Pro-Pro-Ser-Leu-Pro-Ser-Pro-Ser-
Arg-Leu-Pro-Gly-Pro-Ser-Asp-Thr-Pro-Ile-Leu-
Pro-Gln-Cys

Structure (IV) will be recognized as incorporating a Cys component at the amino or N-terminal which is associated with a proline spacer sequence. These spacers serve to position the sequence which follows physically distant from the carrier-modifier. The latter sequence may be observed to present the 138th to 145th amino acid components sequence of the subunit Structure (I). Structure (V) on the other hand, represents an initial sequence corresponding with the 111th to 118th components of the subunit Structure (I) followed by a sequence of six proline spacer components and a carboxyl terminal, present as cysteine. The rationale in providing such a structure is to eliminate the provision of sites which may remain antigenically neutral in performance. Structures (IV) and (V) represent relatively shorter amino acid sequences to the extent that each serves to develop one determinant site. Consequently, as alluded to in more detail hereinafter, they are utilized in conjunction with a mixed immunization technique wherein a necessary two distinct determinants are provided by the simultaneous administration of two such fragments, each conjugated to a corresponding, separate carrier macromolecule. Structure (VI) represents the 115th through 145th component sequence of structure (I). Structure (VII) represents a portion of Structure (I), however, essentially, a sequence of the 111th to 130th components thereof is formed.

Structure (VIII) incorporates two sequences, one which may be recognized in Structure (V) and the other in Structure (IV). These two sequences are separated by two spacer sequences of proline components and one is jointed with an intermediately disposed cysteine component which serves a conjugation function as described later herein. With this arrangement, two distinct determinant sites are developed in physically spaced relationship to avoid the development of an unwanted artificial determinant possibly otherwise evolved in the vicinity of their mutual coupling. Structure (VIIIa) represents Structure (VIII) with additional proline spacer residues to provide a widened spacing of determinant sites.

Structure (IX) mimics sequences from Structure (I) with the addition of a proline spacer sequence, a cysteine component at the C-terminal, and an Aba substituted for cysteine at the 110 position. The Aba designation is intended herein to mean alpha aminobutyric acid of Cysteine. Structure (X) will be recognized as a combination of Structure (II) with a six residue proline spacer sequence and a cysteine component at the C-terminal. Similarly, Structure (XI) combines Structure (II) with a cysteine component at the C-terminal without a proline spacer sequence.

Structure (XII)

Thr-Cys-Asp-Asp-Pro-Arg-Phe-Gln-Asp-Ser-Ser-

Ser-Ser-Lys-Ala-Pro-Pro-Pro-Ser-Leu-Pro-Ser-

Pro-Ser-Arg-Leu-Pro-Gly-Pro-Ser-Asp-Thr-Pro-

Ile-Leu-Pro-Gln

Structure (XIII)

Asp-His-Pro-Leu-Thr-Aba-Asp-Asp-Pro-Arg-Phe-

Gln-Asp-Ser-Ser-Ser-Lys-Ala-Pro-Pro-Pro-

Ser-Leu-Pro-Ser-Pro-Ser-Arg-Leu-Pro-Gly-Pro-

Ser-Asp-Thr-Pro-Ile-Leu-Pro-Gln-Cys

Structure (XIV)

Cys-Pro-Pro-Pro-Pro-Pro-Pro-Asp-Asp-Pro-

Arg-Phe-Gln-Asp-Ser-Ser-Ser-Lys-Ala-Pro-

Pro-Pro-Ser-Leu-Pro-Ser-Pro-Ser-Arg-Leu-Pro-

Gly-Pro-Ser-Asp-Thr-Pro-Ile-Leu-Pro-Gln

Structure (XII) will be recognized as having the sequence of Structure (II) with the addition of Thr-Cys residues at its N-terminal. Structure (XIII) is similar to Structure (IX) but does not contain the spacer sequence. Structure (XIV) will be recognized as being similar to Structure (II) with the addition of spacer components at the N-terminal and a cysteine residue, which may be useful for modification reactions, as described in more detail below.

As already mentioned, it is only the 111–145 amino acid sequence of beta-HCG which differs from the corresponding sequence of LH. However, research indicates that the polypeptides used in the instant processes may contain sequences corresponding to the 101–110 sequence which is common to beta-HCG and beta-LH without inducing the formation of antibodies reactive to LH. Thus, one can use in the instant antigens and methods peptides containing part or all of the common 101–110 sequence without causing substantial cross-reactivity with LH. For example, Structure (II) above represents the 111–145 amino acid sequence of beta-HCG. If desired, therefore, a peptide having the 101–145 amino acid of beta-HCG could be substituted for the peptide of Structure (II) in the instant modified polypeptides without substantially affecting the activity of the modified polypeptide and without causing cross-reactivity with beta-LH.

Two further preferred polypeptides derived from beta-HCG are primarily intended for use in the linear polymers of polypeptides discussed in more detail below. These two preferred fragments are:

Asp-Asp-Pro-Arg-Phe-Gln-Asp-Ser-Ser-Ser-

Lys-Ala-Pro-Pro-Pro-Ser-Leu-Pro-Ser-Pro-Ser-

Arg-Leu-Pro-Gly-Pro-Ser-Asp-Thr-Pro-Ile-Leu-

Pro-Gln-Cys (hereinafter designated fragment

A); and

Asp-His-Pro-Leu-Thr-Cys-Asp-Asp-Pro-Arg-Phe-

-continued

Gln-Asp-Ser-Ser-Ser-Ser-Lys-Ala-Pro-Pro-Pro-

Ser-Leu-Pro-Ser-Pro-Ser-Arg-Leu-Pro-Gly-Pro-

Ser-Asp-Thr-Pro-Ile-Leu-Pro-Gln-Cys

As mentioned earlier, the main utility presently envisaged for modified polypeptide of the invention derived from mammalian reproductive hormones or fragments thereof is useful as contraceptives and/or abortifactants by administration of the modified polypeptide to the female mammal. However, modified polypeptides of the invention derived from mammalian reproductive hormones or fragments thereof have a variety of other uses. Since the modified polypeptides do provoke the production of antibodies to the endogenous reproductive hormone when injected into animals, they can be used, in ways which will be familiar to those skilled in the art, for the production of antibodies specific to the endogenous reproductive hormone from which the modified polypeptide is derived. The antibodies may be produced, for example, by injecting the modified polypeptide into a suitable mammal, extracting blood or other body fluid or tissue from the mammal and harvesting the antibodies from the extracted blood, body fluid or tissue.

The antibodies thus produced may be used in a wide variety of tests and treatments. For example, since the antibodies thus produced are specific to an endogenous hormone, they may be used, in ways which will be familiar to those skilled in the art, to perform qualitative or quantitative assays for the endogenous hormone in the tissues or body fluids of the mammal which produced the endogenous hormone to which the antibody is specific, the antibodies produced by the process of the present invention may be useful in diagnostic tests to determine whether hormone levels in a mammal are abnormal. For example, abnormal levels, usually lowered levels, of certain reproductive hormones are often associated with reduced fertility or infertility in man and other mammals, and consequently antibodies produced by the processes of the invention may be used in tests for such conditions of reduced or absent fertility. Such tests for reduced or absent fertility are not only useful in humans, but may also be desired by veterinarians charged with the care of valuable breeding animals such as stallions at stud or valuable pedigree bulls. For example, a peptide having a requisite sequence determinant of equine chorionic gonadotropin can be used to prepare a modified polypeptide of the invention, which can then be passed through a suitable mammal to generate antibodies to equine chorionic gonadotropin. Such antisera would be useful for infertility diagnosis in valuable thoroughbred horses.

The antibodies produced by the process of the present invention may also be useful in pregnancy tests in man and other mammals. As previously noted, human chorionic gonadotropin was first discovered because it is present at relatively high levels in the urine of pregnant women, and detection of the elevated levels of human chorionic gonadotropin in the urine of pregnant women is the basis for most pregnancy tests. By virtue of their specificity to human chorionic gonadotropin (or the corresponding gonadotropin in other mammalian species) antibodies produced by the process of the present invention may be useful in such pregnancy tests. Such pregnancy tests are not only useful in humans; for example, a pregnancy test may be highly desirable in a brood mare in order to ensure that she is in foal. In the absence of such a pregnancy test, an owner might incur an additional heavy stud fee unnecessarily.

The uses of the antibodies produced by the processes of the present invention are not, however, confined to assay of the level of endogenous hormones (or, if desired, non-hormonal proteins) in mammals. In addition, the instant antibodies may also be useful in producing physiological changes in the tissues of a mammal.

POLYPEPTIDES DERIVED FROM THE ZONA PELLUCIDA, FROM SPERM OR FROM PLACENTAL TISSUE

Another group of polypeptides which can be altered by the instant processes, and used in the field of fertility control in both humans and other mammals, are specific non-hormonal protein antigens isolated from placental tissue. There is direct evidence that inhibition of substances that are specific to the placental tissue and do not have similar antigenic properties with other antigens from organs in other parts of the body, can result in the disruption of pregnancies by passive immunization. Such specific placental substances when modified to form modified polypeptides by the procedures described herein can be injected into the body of an animal of the same species as an effective fertility control means with the mechanism being active immunization similar to that described for the antigenic modification of hormones. The particular advantages of these substances is that placental antigens are foreign to the non-pregnant female human subject and therefore are unlikely to cause any cross-reaction or disruption of normal body function in the non-pregnant female.

A further group of polypeptides which may be modified by the instant processes to yield modified polypeptides useful for fertility control are polypeptides derived from zona pellucida or from sperm, and peptides having a sequence corresponding to at least part of the sequence of such a zona pellucida or sperm antigen.

It is known that antigens from the zona pellucida (the outer covering of the ovum) when injected into female primates produce antibodies having anti-fertilization effects, including prevention of sperm attachment to, and penetration of, the zona pellucida of the unfertilized ovum, and prevention of dispersal of the zona pellucida of the fertilized ovum prior to implantation (such dispersal of the zona apparently being an essential prerequisite for implantation). See e.g. W. R. Jones, "Immunological Fertility Regulation", Blackwell Scientific Publications, Victoria, Australia (1982), pages 160 et seq. Such anti-fertility effects are believed to be due to formation of an antibody-antigen precipitate on the zona, this precipitate rendering the zona unable to undergo its normal sperm-binding reaction and also rendering the zona insensitive to the action of the proteases normally responsible for dispersal of the zona.

Another possible approach to the production of anti-fertility vaccine uses sperm antigen. Several antigens, especially sperm enzymes, known to exist in sperm, may be used in the modified antigens of this invention; see W. R. Jones, op. cit., pages 133 et seq. The most promising such antigen is the lactate hydrogenase known as LDH-C4 or LDH-X. Although of course lactate dehydrogenases are present in other tissues, LDH-C4 is distinct from other lactate dehydrogenase isoenzymes and appears to be sperm-specific. Moreover, the enzyme is not strongly species specific, and methods for its isolation and purification are known. Again, the best results should be obtained by modifying LDH-C4 or a fragment thereof to produce a modified polypeptide of this invention. Several natural peptide fragments of LDH-C4 have been prepared, sequenced and shown to bind to antibodies against the parent molecule. (See E. Goldburg, "LDH-X as a sperm-specific antigen", in T. Wegmann and T. J. Gill (eds.), *Reproductive Immunology*, Oxford University Press, 1981). (The disclosure of this work is herein incorporated by reference.)

Although theoretically an anti-fertility vaccine based on sperm antigens might be useful in males, the likelihood of testicular damage renders it more likely that such a vaccine will find its utility in females. It is known that circulating antibodies in the female bloodstream do penetrate the genital fluids; for example experiments in baboons with vaccines based upon the peptide of Structure (XII) above conjugated with tetanus toxoid have shown the presence of HCG antibodies in the genital fluids. However, one possible problem with any vaccine based on sperm antigens is maintaining a sufficiently high antibody level in female genital fluids to complex with the large amounts of sperm involved.

RELAXIN

Another group of peptides which can be modified by the methods of the instant invention for use in fertility control are relaxin and polypeptides derived therefrom. It has been known for a long time that relaxin is a peptide hormone synthesized in the corpus luteum of ovaries during pregnancy and the hormone is released into the bloodstream prior to parturition. The major biological effect of relaxin is to remodel the mammalian reproductive tract to facilitate the birth process, primarily by relaxing the cervix, thereby assisting in the dilation of the cervix prior to parturition. The amino acid sequence, which bears some resemblance to that of insulin, has been determined; see: Hudson et al., "Structure of a Genomic Clone Encoding Biologically Active Human Relaxin". This paper also gives methods for the synthesis of certain relaxin-derived peptides.

The use of relaxin or peptides derived therefrom in fertility control according to the instant invention depends not upon the natural function of relaxin during parturition, but upon the fact that anti-relaxin antibodies are known to render sperm immotile. Thus, there appears to be a relaxin-like antigen present on the surface of sperm, especially since the immotility of the sperm can be reversed by adding relaxin to the antibody/sperm complex. As mentioned above, in theory one could use modified sperm antigens prepared by the instant processes to generate in the male antibodies to various antigens present in sperm, but there is the serious problem that, owing to the blood/testes barrier, such anti-sperm antigens do not penetrate the testes. The potentially very rapid induction of immotility of anti-relaxin antibody renders generation of such an antibody in males a highly attractive potential form of male contraception. Although the anti-relaxin antibodies will not penetrate the testes because of the blood/testes barrier, they can penetrate the epididymis and they will also be secreted into the fluid which becomes mixed with the sperm shortly before or during ejaculation. Thus, by producing anti-relaxin antibodies in the male, ejaculation would take place normally but the sperm produced would be immotile. Furthermore, the risk of complications and unintended tissue damage by such an instant process is slight, since the antibodies will not enter the testes, thereby avoiding potentially damaging reactions due to antibody-antigen binding within the testes.

It should be noted that injection of modified relaxin-derived peptides modified by the instant processes into females is not recommended; such a process would carry too great a risk of ovarian damage in the female.

It should also be noted that relaxin is a highly species-specific protein. Accordingly, when choosing an appropriate peptide derived from relaxin for modification by the instant processes, care should be taken to ensure that the peptide corresponds to part of the sequence of human relaxin (or, of course, relaxin of any other species which it is designed to treat).

CANCER TREATMENT

Another health problem that can be treated by the instant methods is that of certain endocrine or hormone-dependent breast tumors or cancers. Certain of these cancers have been shown to be dependent upon the abundant secretion of the hormone prolactin for their continued survival. The inhibition of the secretion of prolactin has been shown to diminish the growth rate and the actual survival of certain of these tumors. The immunization of mammals suffering from such tumors with modified polypeptides related to prolactin and produced by the instant methods would result in the systematic reduction of the level of prolactin circulating in the system and consequently may result in the regression or remission of tumor growth. The consequence of this treatment would be far more favorable in terms of effective treatment of this disease, since surgical removal of the breast is the principal method of treatment currently available. It will of course be understood that this aspect of the instant invention will be effective only with regard to those tumors which are dependent upon the secretion of prolactin (or some other hormone modifiable by the processes of the instant invention) for survival.

Investigators have also determined, for example, that certain polypeptide entities are supportive factors to, and secretions of, neoplastic diseases in both man and other mammals. These supportive entities have biochemically, biologically and immunologically close resemblances to hormones, particularly to CG as well as to LH. By applying the iso-immunization techniques of the instant invention (i.e. by injecting into the mammal a modified polypeptide which produces antibodies to a natural hormone or other protein of the mammal) the function of such polypeptides or endogenous counterparts can be neutralized to carry out regulation of the malignancy. For example, tumors in both male and female primates may be treated by isoimmunization procedures developing antibodies to CG or LH or the supported entity analogous thereto. Furthermore, neoplasms in primate females may be regulated by isoimmunization procedures developing antibodies to endogenous LH. This hormone, when associated with a tumor state, tends to aggravate the tumorous condition.

It appears (although the invention is in no way limited by this belief) that certain carcinomas exude CG or an immunologically-similar material on their surfaces, thereby presenting to the immune system of the host animal a surface which, superficially, appears to be formed of material endogenous to the host animal and which is thus relatively non-immunogenic. Because of this known association between certain carcinomas and CG or CG-like materials, the instant modified polypeptide derived from CG described above are useful not only for fertility control but also for treatment of carcinomas associated with CG or CG-like materials.

Example XXXIV below shows that a beta-HCG/tetanus toxoid modified polypeptide of the invention confers upon rats substantially complete protection against an injection of tumor cells of the virulent rat mammary adenocarcinoma R 3230 AC, which is associated with CG-like material. The aforementioned polypeptide of the invention, when given prior to injection of a dose of tumor cells which causes 100% mortality in unprotected, reduces the mortality to 0. Further work showing the use of the instant modified polypeptides in carcinomas is given in Examples XXXVI–XXXVIII.

HYPERTENSION

Another serious medical problem which can be treated by the instant invention is that of hypertension. In general terms, the state of hypertension is the abnormal level or fluctuation of one's blood pressure. The blood pressure of an individual is controlled by many physiological processes in the body. However, two major substances affecting the regulation of such pressure are the hormonal polypeptides known as angiotension I and II. In certain states of high blood pressure (hypertension) it is difficult to control medically the secretion into, and therefore the level of angiotension I and II in, the circulatory system. By appropriate modification of one or both of these hormones and subsequent immunization of the hypertensive patient with the modified hormone, it is possible to reduce the secretion of angiotension I and/or II in patients with chronically elevated hormone levels. The predictable and controlled reduction of these substances is beneficial to certain patients with chronic problems of hypertension. Modified angiotension I and II can be produced by any of the modification techniques described below. The resultant modified angiotension I or II is simply injected into the patient in an amount sufficient to induce added antibody response sufficient to control or regulate unmodified angiotension I and/or II to the desired degree.

The structures of both angiotension I and II are known, that of angiotension I being as follows:

Asp-Arg-Val-Try-Ile-His-Pro-Phe-His-Leu, while the structure of angiotension II is:

Asp-Arg-Val-Try-Ile-His-Pro-Phe.

In view of the relatively small sizes of these peptides (the molecular weight of the I form is 1296.7 and that of the II form 1046.3), it is recommended that modification be carried out using the intact hormone as the polypeptide to be modified.

DIABETES AND ASSOCIATED VASCULAR DISEASES

The present invention is applicable to the treatment of diabetes and associated micro- and macro-vascular diseases. Currently, the treatment of diabetes is limited to dietary and/or drug treatment to regulate blood glucose levels. Recent scientific data support the concept that growth hormone and somatomedian (both polypeptides) are intimately involved in the disease syndrome. These substances can be modified by the technique described herein and used in an effective amount to control the progress of this disease. In practice, modified growth hormone or modified somatomedian is injected into the body to develop antibodies for control of the normally secreted hormones.

Naturally, the use of the present invention to treat elevated levels of growth hormone and/or somatomedian is not confined to diabetic patients. Thus, the present invention may be used to treat non-diabetic patients, such as persons suffering from acromegaly, who have excessive levels of growth hormone and/or somatomedian.

MISCELLANEOUS HORMONE-RELATED CONDITIONS

The present invention, as already noted, is applicable to the treatment of an extremely wide range of hormone-related condition. Indeed, as explained above, in principle the present invention is applicable to the treatment of any condition which is caused by excessive levels of a hormone or non-hormonal protein in a mammal. One such disease state which can be treated by the present invention is the digestive disorder known to those skilled in the medical field as Zollinger-Ellison Syndrome. This syndrome or disease state is generally described as a condition in which a hypersecretion of the polypeptide gastrin, which is produced in the pancreas, brings about a state of hyperacidity in the stomach which results in a chronic digestive disorder. Heretofore, the only effective treatment for this disease state was the surgical removal of a part or total removal of the subject's stomach. Although survival of such patients is usually not threatened, the medical state and life style of such individuals is severely affected by such treatment.

Treatment of such subjects with gastrin-derived modified polypeptides of the invention can be used to enhance the production of antibodies against the hypersecretion of gastrin and thereby alleviate or reduce the systems of this disease without surgical intervention. Sufficient reduction by immunological means of this substance in the system of the body would be sufficient to avoid the complicated and serious consequences of the surgical treatment currently in use. In practice, an effective amount of modified gastrin is simply injected into the patient as required to accomplish the control of the flow or presence of gastrin.

Other disease states and the associated hormones which may be modified by the instant processes or immunological treatment of the diseases are as follows:

(1) modified parathyroid hormone for the treatment of kidney stones,
(2) modified insulin and/or glucagon for the treatment of hyperinsulinoma,
(3) modified thyroid stimulating hormone (TSH) for the treatment of hyperthyroidism, and
(4) modified secretion for the treatment of irritable syndrome.

NON-ENDOGENOUS PROTEINS

In the specific aspects of the invention described above, the peptide which is modified to produce the instant modified polypeptide is a peptide having a sequence corresponding to at least part of the sequence of a protein endogenous to the animal in which the modified polypeptide is to be employed. However, the techniques of the present invention can usefully be extended to proteins which are not endogenous nor substantially immunogenic to the mammal to be treated. By the instant methods, these substantially non-immunogenic, non-endogenous proteins or fragments thereof can be modified so as to stimulate the animal's immune system to produce antibodies to the non-endogenous proteins. As those skilled in the art are aware, there are numerous pathogens and similar materials known which are not endogenous to animals, which are capable of producing harmful effects in the animal's body but which are not immunogenic to the animal, in the sense that introduction of the pathogen or other material into the body of the animal fails to elicit from the animal's immune system production of the quantity of appropriate antibodies necessary for the animal's immune system to destroy the pathogen or similar material.

For example, the Herpes simplex Type II virus is capable of producing a number of harmful effects in man, including the production of painful lesions in the genital areas. Although this virus has, like most viruses, protein included in its structure, the viral protein is not strongly immunogenic in most human beings, so that only about 50% of infected human beings produce antibodies to the virus. This lack of immune response to the virus by many human beings means that the virus can remain in the infected human beings for at least several years, and this persistence of the virus in the infected individuals not only causes these individuals to suffer recurrent attacks of the painful symptoms caused by the virus, but also renders them long-term carriers of the virus. This persistence of the virus in infected individuals is one of the factors largely responsible for the epidemic proportions which Herpes simplex infections have reached in several countries. By preparing an antigen of this invention derived from a protein having a sequence similar to that of at least part of the sequence of a Herpes simplex viral protein, it is possible to stimulate the human immune system so as to render it capable of producing large quantities of antibodies to the Herpes simplex virus. Not only should this stimulation of the immune system reduce the occurrence of symptoms associated with Herpes simplex infection, but it should help to control the spread of the virus. Similarly, the immune response of humans and other animals to viruses such as colds, influenza and other viruses can be increased by preparing modified antigens of the invention based upon peptides having sequences corresponding to viral proteins of the appropriate virus. If, as appears likely, a virus is responsible for acquired immune deficiency syndrome (AIDS) a modified antigen of this invention could also be used to produce immunity to this disease.

TECHNIQUES FOR MODIFICATION OF POLYPEPTIDES

A wide range of techniques may be used in the present invention to modify the polypeptides. In general, any type of chemical modification, which renders the modified polypeptide more immunogenic to the mammal to which it is to be administered than the unmodified polypeptide from which the modified polypeptide is derived, may be used in the present invention. However, the two major chemical techniques of chemical modification employed in the present invention are conjugation of the peptide to a similar carrier molecule, and polymerization (a term which is used in its broad sense to include, for example, dimerization) of the polypeptide. These two major techniques will now be discussed, and thereafter a group of miscellaneous chemical modification techniques which may be useful in some instances will also be discussed. Many of the techniques described below are not in themselves novel and some of the techniques may be found in the following list of literature references, while various others may be found elsewhere in literature by persons skilled in the art:

1. Klotz et al., *Arch. of Biochem. and Biophys,* 96,60, 605–612, (1966).
2. Khorana, *Chem. Rev.*, S3, 145 (1953).
3. Sela et al., *Biochem. J.,* 85, 223 (1962).
4. Eisen et al., *J. Am. Chem. Soc.,* 75, 4583 (1953).
5. Centeno et al., *Fed. Proc.* (ABSTR) , 25, 729 (1966).
6. Sokolowsky et al., *J. Am. Chem. Soc.,* 86, 1212 (1964).
7. Tabachnick et al., *J. Biol. Chem.,* 234, 1726, (1959).
8. Crampton et al., *Proc. Soc. Exper. Biol. & Med.,* 80, 448 (1952).
9. Goodfriend et al., *Science,* 144, 1344 (1964).
10. Sela et al., *J. Am. Chem. Soc.,* 78, 746 (1955).
11. Cinader et al., *Brit. J. Exp. Pathol.,* 36, 515 (1955).
12. Phillips et al, *J. of Biol. Chem.,* 240(2), 699–704 (1965).
13. Bahl, *J. of Biol. Chem.,* 244, 575 (1969).

It will be appreciated by those skilled in the art that, in the instant invention, the chemical modification of the polypeptide is effected outside the body of the animal prior to introduction of the modified polypeptide into the body of the animal.

In general, the methods used for preparing the instant modified polypeptide based upon non-endogenous proteins, such as viral proteins or peptides corresponding to parts thereof, are the same as those used for modifying endogenous proteins or fragments thereof, although it will be appreciated that the preferred methods used for modifying a non-endogenous materials may differ in certain respects from those used in modifying endogenous polypeptides. Since, in general, the non-endogenous peptide will provoke at least a limited immune response from the animal in which the antigen is to be administered, it may well be that the requirements for modification of the non-endogenous peptide to produce the instant modified polypeptide are less stringent than those modifications of an endogenous and completely non-immunogenic polypeptide. However, since the non-endogenous polypeptide is being modified to increase its immunogenic effect in the animal into which it is to be administered, in general it will still be desirable that the carrier used to modify the non-endogenous polypeptide to produce the instant modified polypeptide be a material which itself provokes a strong response from the animal's immune system.

For example, where the modified polypeptide is prepared by conjugation of the polypeptide to a carrier, the carrier may be a bacterial toxoid such as diphtheria toxoid or tetanus toxoid.

CONJUGATION OF THE POLYPEPTIDE TO A CARRIER

One preferred way of effecting the necessary chemical modification of the polypeptide (whether that polypeptide be an intact protein or a fragment thereof) in the processes of the instant invention is so-called conjugation of the polypeptide to a carrier. Such conjugation is accomplished by attaching to the polypeptide one or more foreign reactive (modifying) groups and/or by attaching two or more polypeptides to a foreign reactive group (i.e. a carrier) or both of the above, so that the body of the animal, recognizing the modified polypeptide as a foreign object, produces antibodies which neutralize not only the modified polypeptide but also the unmodified protein related to the polypeptide and responsible for the disease or medical problem being regulated.

For example, the HCG-derived peptide of Structure (II) may be modified by conjugation with a polytyrosine chain or a protein macromolecule carrier, thereby causing the peptide of Structure (II) to become antigenic so that the resulting administration of the modified peptide of Structure (II) will provide the desired immunological action against natural HCG. Another example of chemical modification by conjugation would be conjugation of any of the HCG-derived peptides designated Structures (II)–(XIV) above by coupling to a carrier such as Ficoll 70 (a synthetic copolymer of sucrose and epichlorohydrin having an average molecular weight of 70,000±1,000, good solubility in water, Stokes radius about 5.1, and stable in alkaline and neutral media, available from Pharmacia Fine Chemicals, Pharmacia Laboratories, Inc. 800 Centennial Avenue, Piscataway, N.J. 08854) or other carriers such as the protein macromolecules described below.

Particularly where the larger whole hormone or subunit type molecular structures are concerned, the number of foreign reactive groups which are to be attached to the polypeptide and the number of polypeptides to be attached to a foreign reactive group depends on the specific problem being treated. Basically, what is required is that the concerned polypeptide be modified to a degree sufficient to cause it to be antigenic when injected in the body of the animal. If too little modification is effected, the body may not recognize the modified polypeptide as a foreign body and would not create antibodies against it. If the number of foreign molecules added to the polypeptide is too great, the body will create antibodies against the intruder antigen, but the antibodies will be specific to the injected antigen and will not neutralize the action of the concerned natural endogenous hormone or non-hormonal protein, i.e. they will be specific to the modifier.

In general, again considering the larger molecule subunit or whole hormone, it has been found that about 1–40 modifying groups per molecule of polypeptide will be useful in modifying the polypeptide adequately so as to obtain the desired immunological effect of this invention. As will be appreciated by one skilled in the art, this ratio of modifying groups per polypeptide will vary depending upon whether an entire hormone is utilized for modification or whether for instance a relatively small synthetic fragment of the hormone is to be modified. Generally for the larger molecules, it is preferred that 2–40 modifying groups per molecule of polypeptide be used according to this invention. In the instance where the polypeptide is the beta-subunit of HCG, it is particularly preferred that about 5–30 and more preferably 10–26 modifying groups per molecule of polypeptide be used. The important consideration with respect to each modified polypeptide is that the degree of modification be adequate to induce generation by the animal of antibodies adequate to neutralize some of the natural hormone or non-hormonal protein the neutralization of which is desired, and this will vary with each polypeptide involved, and the degree of correction or change desired for the body function involved.

Modification of the polypeptide is accomplished by attaching various kinds of modifying groups to proteinaceous hormones, non-hormonal proteins, subunits or specific fragments thereof according to methods known in the art.

As will be apparent from the formulae given above, the HCG-derived polypeptides of Structures (II)–(XIV) are relatively smaller fragments of HCG, which can be produced synthetically. To render them capable of eliciting antibody production, it becomes necessary to conjugate them with larger carrier-modifier molecules. Generally about 5–30 peptide fragments will be coupled with one carrier molecule. The body will, in effect, recognize these foreign carriers as well as the sequences represented by the fragments and form antibodies both to the carrier and to the sequences of the coupled fragments. Note that the carrier-modifiers are foreign to the body and thus antibodies to them will not be harmful to any normal body constituents. In the latter regard, it may be found preferable to utilize a carrier which, through the development of antibodies specific to it, will be found beneficial to the recipient.

As indicated earlier herein, it also is preferred that the modification constitute two or more immunological determinants represented on the native protein as polypeptide structures to which it is desired to evoke an antibody response. The effect is one of heterogeneity of antibody development. Thus, several fragment structures have been described above having at least two distinct amino acid sequences represented in the HCG beta subunit. These sequences may be so spaced as to derive the determinants in mutual isolation, while the spaced sequence fragment is conjugated with a larger, macromolecular carrier. Alternately, the noted mixed immunization arrangement may be utilized wherein a first fragment developing one determinant is conjugated with a first carrier molecule and is administered in combination with a second, distinct fragment which is conjugated with a second carrier molecule, the latter of which may be the same as or different in structure from the first carrier. Thus, each macromolecular carrier must be conjugated with hormone fragments such that each fragment represents two or more immunological determinants. These two necessary determinants can be evolved by mixing, for example, separate conjugate structure, for example based upon Structures (IV) and (V) each of which, through forming antibodies separately to the distinct determinants, will provide a population of antibodies reacting with two separate determinants on the natural endogenous hormone.

Inasmuch as the noted fragments are relatively small as compared, for instance, to a whole hormone or subunit thereof, a criterion of size is imposed upon the selection of a carrier. The carrier size must be adequate for the body immune system to recognize its foreign nature and raise antibodies to it. Additionally, carrier selection preferably is predicated upon the noted antibody heterogeneity requirement, i.e. the carrier must itself evoke a heterogeneous immune response in addition to the fragments. For example, improved response may be recognized where the carrier is varied in structure, e.g. incorporating branching chains to enhance the recognition of both the carrier and the attached polypeptide as being of a foreign nature.

As one example of whole hormone modification, modified diazo groups derived from sulfanilic acid may be attached to the subject polypeptides, see the Cinader et al. and Phillips et al. references cited above for instruction on how this "attachment" is accomplished, and to the extent necessary for an understanding of this invention, such is incorporated herein by reference.

Additional modifying groups for modifying whole hormones or their subunits are those groups obtained by reaction of the polypeptides with dinitrophenol, trinitrophenol, and S-acetomercaptosuccinic anhydride, while suited for utilization as carrier-modifiers in conjunction with fragments, are polytyrosine in either straight or branched chains, polyalanines in straight or branched chains, biodegradable polydextrans, e.g. polymerized sugars such as sucrose copolymerized with epichlorohydrin, e.g. Ficoll 70 and Ficoll 400 (a synthetic copolymer of sucrose and epichlorohydrin having an average molecular weight of 400,000±100,000 intrinsic viscosity of 0.17 dl/g. specific rotation $[alpha]^{20}_D$ of +56.50, available from Pharmacia Fine Chemicals, Pharmacia Laboratories, Inc. 800 Centennial Ave., Piscataway, N.J. 08854) or a polyglucose such as Dextran T 70 (a glucan containing alpha-1,6-glucosidic bonds and having an average molecular weight of approximately 70,000, synthesized microbiologically by the action of *Leuconostoc mesenteroides* strain NRRL B-512 on sucose), serum proteins such as homologous serum albumin, hemocyanin from Keyhole limpet (a marine gastropod mollusk) viruses such as influenza virus (type A, B, or C) or poliomyelitis virus, live or killed, Types 1, 2 and 3 of tetanus toxoid, diphtheria toxoid, cholera toxoid or somewhat less preferably, natural proteins such as thyroglobulin, and the like. Generally, synthetic modifiers are preferred over the natural modifiers. However, carrier-modifiers found particularly suitable for conjugation with the above-discussed fragment structures are flagellin, tetanus toxoid and an influenza subunit, for example, the preparation of which is described by Bachmeyer, Schmidt and Liehi, "Preparation and Properties of a Novel Influenza Subunit Vaccine", *Post-Graduate Medical Journal*, (June, 1976), 52,360–367. This influenza subunit was developed as a vaccine which incorporates essentially only the two viral proteins, hemagglutinin and neuraminidase. Containing substantially only these two essential immunogens, the subunit represents a preparation which does not contain other protein and lipid antigens which may be found to cause underdesired side reactions. A secondary benefit may be realized through the utilization for example, of the influenza subunit, poliomyelitis virus, tetanus toxoid, diphtheria toxoid, cholera toxoid or the like as a modifier-carrier, inasmuch as beneficial antibodies will be raised to that modifier-carrier as well as the hormonal fragment conjugated thereto.

Flagellin is a protein described as forming the wall of the main spiral filament of the flagellum. Bacterial flagella, in turn, have been known as the active organelles of cell locomotion, individual flagella (flagellum) occurring in suspension as individual spirals which, upon drying, collapse into filaments which describe a sine wave with a wave length of 2–3 microns and an amplitude of 0.25–0.60 microns. Generally, the flagellum consists of three morphologically distinct parts: a basal structure that is closely associated with the cytoplasmic membrane and cell wall, a hook and the noted main spiral filament.

Purified flagellin is readily obtained by solubilization of flagellar filaments below a pH value of about 4, and subsequent removal of the insoluble material by centrifugation or filtration. As a group of related proteins, flagellins from different bacterial species have been predicted to have similar amino-acid compositions. However, the amino acid composition of each flagellin species is unique. Essentially all flagellins are described as containing no or only a few residues of cysteine, tryptophan, tyrosine, proline and histidine. Thus, when conjugated with fragments in accordance with the invention, a thiolactonization procedure or the like is carried out as described later herein.

The molecular weights of various flagellins have been calculated, in all cases the values thereof of the monomeric subunits falling in the range of 30,000 to 50,000. From an immunological standpoint, a flagellin molecule is highly immunogenic. For further and more detailed discourse describing bacterial flagella and flagellin, reference is made to "Advance in Microbial Physiology", 6, 219(1971), "Bacterial Flagella" by R. W. Smith and Henry Coffler, which publication is incorporated herein by reference.

Tetanus toxoids have been the subject of study and production for many years. The toxoid generally is evolved from a formalinization of tetanus toxin, the latter being a protein synthesized by *Clostidium tetani*. Immunization currently is carried out utilizing soluble and absorbed tetanus toxoid and suggestions have been made concerning the utilization of fluid tetanus toxoid in complex with antitoxin. Publications describing the toxin and toxoid are numerous, reference being made to the following:

1. "Immunochemistry of Tetanus Toxin", Bizzini, et al., *Journal of Biochemistry*, 39, 171–181 (1973).
2. "Early and Enhanced Antitoxin Responses Elicited with Complexes of Tetanus Toxoid and Specific Mouse and Human Antibodies", Stoner et al., *Journal of Infectious Diseases*, 131, (3), 230–238 (1975).
3. "Differences in Primary and Secondary Immunizability of Inbred Mice Strains", Ipsen, *Journal of Immunology*, 83, 448–457 (1959).

4. "Antigenic Thresholds of Antitoxid Responses Elecited in Irradiated Mice with Complexes of Tetanus Toxin and Specific Antibody", Hess et al., *Radiation Research,* 25, 655–667 (1965).
5. "Early and Enhanced Germinal Center Formation and Antibody Responses in Mice After Primary Stimulation with Antigen-isologous Antibody Complexes as Compared with Antigen Alone", Laissue et al., *Journal of Immunology,* 107, 822–825 (1971).
6. "Distinctive Medullary and Germinal Center Proliferative Patterns and Mouse Lymph Nodes after Regional Primary and Secondary Stimulation, with Tetanus Toxoid", Buerki et al., *Journal of Immunology,* 112, (6), 1961–1970 (1974).

Although the conjugation techniques have been mostly described above, and will in general be mostly described below, with reference to conjugation of polypeptides derived from natural protein hormones, it will be appreciated that exactly similar techniques will be employed for modification of non-hormonal proteins or fragments thereof, for example viral proteins.

Methods for preparing the modified polypeptides of this invention also include the following.

In one preferred modification process, the polypeptide fragment would be modified, for example that designated Structure (XII) above, is activated first, after which it is conjugated with a carrier, for example the influenza subunit described above, tetanus toxoid or flagellin. An activating reagent may be utilized which exhibits differing functionality at its ends and, by choice of reaction conditions, these end functions can be made to react selectively. For example, the activators of Formulae A and B shown in FIG. 9 of the accompanying drawings, which each have a maleiimido group and a substituted acid group, may be used. In these activators, X is a non-reacting group which can be a substituted or unsubstituted phenyl or $C_1$–$C_{10}$ alkylene moiety, or a combination thereof. The substituent on the phenyl ring (if any) should of course be non-interfering with the reactions of the activator, as is the remainder of the grouping X.

The grouping X may be, inter alia, a pentamethylene, 1,4-phenylene or monomethyl-1,4-phenylene grouping.

The maleiimido grouping of the above activators will react with sulfhydryl (SH) groups in the polypeptides to be modified under conditions whereby the opposite end (active ester end) of the reagent does not react with the amino groups present in the polypeptides. Thus, for example, polypeptides, such as that designated Structure (XII) above, contain a cysteine amino acid, and hence an SH group, react as shown in Equation 1 in FIG. 10 of the accompanying drawings. Following the above reaction, upon adjusting the pH to slightly alkaline condition, for example, pH 8, and adding a carrier protein, conjugation is accomplished to produce the product of Formula 2 shown in FIG. 10 of the accompanying drawings.

Figure 9:
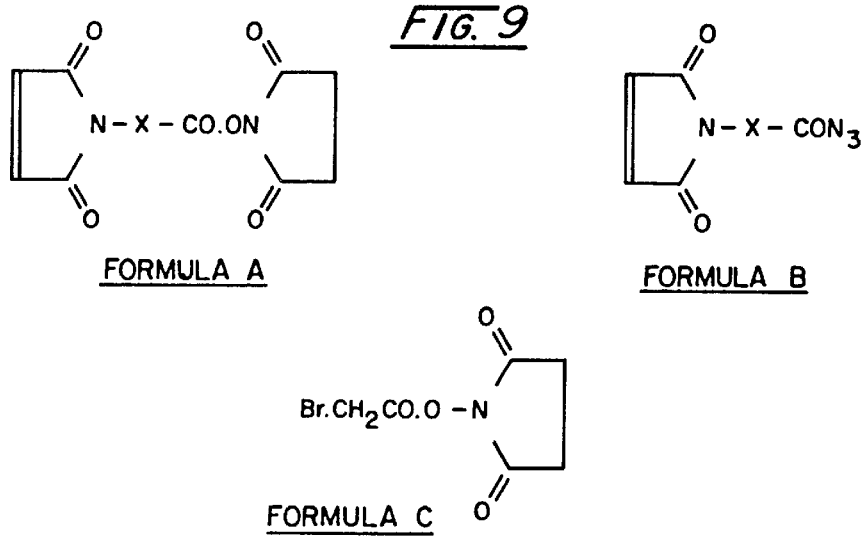
FIG. 9 shows the formulae of three coupling agents used to prepare the modified polypeptides of the invention.
Figure 10:
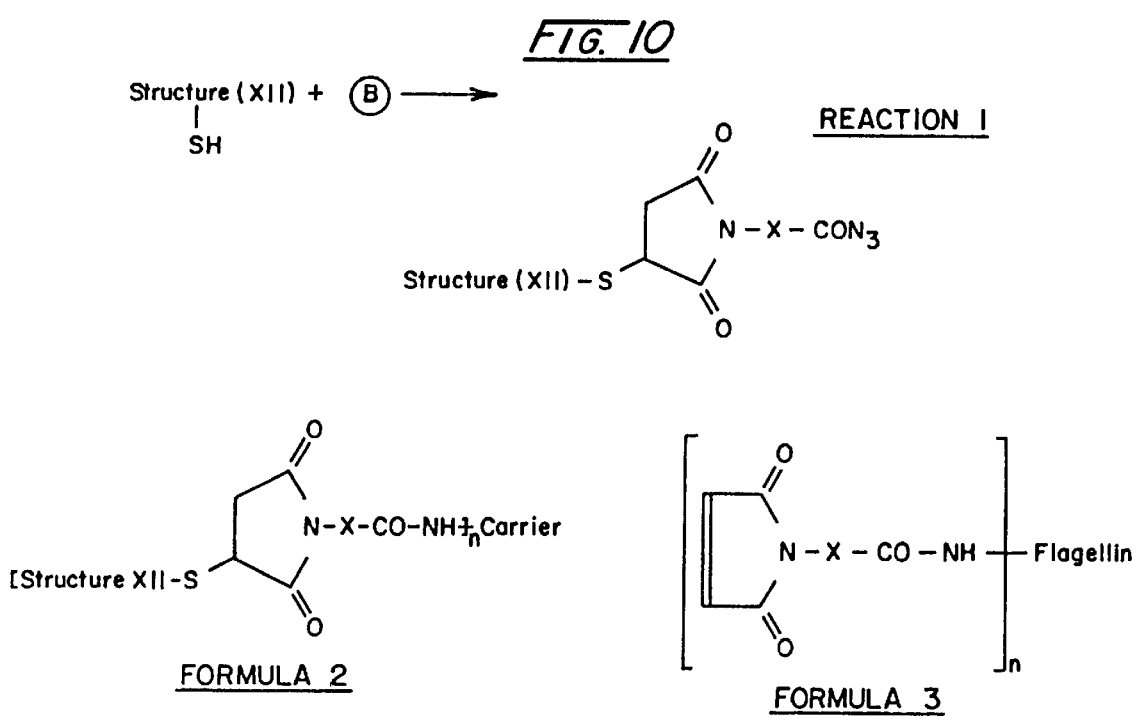
FIG. 10 shows typical reactions used to prepare conjugated modified polypeptides of the invention, together with examples of the modified polypeptides produced by such conjugation reactions.

Preferably a carrier protein, such as the above-noted flagellin, which does not contain SH groups, but does contain $NH_2$ groups, may first be treated with an activator of the formula A or B shown in FIG. 9 of the accompanying drawings, wherein X is as defined above, at pH 7 or lower to cause reaction of the active ester end of the activator with the flagellin, giving a compound of Formula III shown in FIG. 10 of the accompanying drawing. Following the above, the activated carrier is reacted with a polypeptide fragment containing an SH group to derive a product similar to that discussed immediately above.

Should the polypeptide fragment not contain an SH group, e.g. Structures (II), (III), (VI) and (VII), such structures can be modified first to introduce such a grouping by standard methods such as "thiolactonization", following which they are conjugated utilizing the above-discussed selective bi-functional reagents. For a more detailed description of these reagents, reference is made to the following publications:

O. Keller and J. Ridinger, *Helv. Chim. Acta,* 58, 531–541 (1975).

W. Trommer, H. Kolkenbrock and G. Pfleiderer, *Hoppe-Seyler's Z. Physiol. Chem.,* 356, 1455–1458 (1975).

Further description of preferred embodiments of the above-described utilization of bi-functional reagents is provided hereinbelow at Examples XXVII and XXVIII.

As already mentioned, in many natural proteins containing cysteine residues, these residues are not present in the thiol form containing a free SH group; instead, pairs of cysteine residues are linked by means of disulfide bridges to form cysteine. Accordingly, when it is desired to produce free SH groups in proteins to carry out the coupling reactions discussed above, one convenient way of providing such free SH groups may be to cleave disulfide bridges naturally present in the protein or other polypeptides which it is desired to conjugate. For example, as noted above the natural form of beta-HCG contains six disulfide bridges. To produce free thiol groups for coupling reactions, any number of these bridges from 1 to 6 may be broken using known techniques as set out for example in:

Bahl et al, *Biochem. Biophys. Res. Comm.,* 70, 525–532 (1976). This particular article describes cleavage of 3–5 of the six disulfide bridges in beta-HCG, but the same techniques may be used to break all six bridges if this is so desired. It should, however, be noted that the techniques disclosed in this paper are not selective and although it is possible to control the degree of disulfide bridge breaking, it is not possible to break specific bridges and leave others; the breaking of bridges is at random and the thiol groups produced are randomly distributed over the possible positions in beta-HCG.

As an alternative approach to the utilization of the maleiimido group reagents discussed above, an alkylation step may be used to cause conjugation. Conditions can be chosen such that, in the presence of amino groups, essentially only thiol groups will be alkylated. With this approach, the reactions carried out can be represented typically by Reaction 4 shown in FIG. 10 of the accompanying drawings. With this approach, the larger carrier molecule, for example flagellin, tetanus toxoid or the influenza subunit described herein, is first modified by reaction of a fraction of its amino groups with an active ester of chloro, dichloro, bromo, or iodo acetic acid such as the compound of Formula C shown in FIG. 9 of the accompanying drawings. This modified carrier is then reacted with the sulfhydryl group in the polypeptide to be modified, or a modified form of the polypeptide which has already been modified to contain a free thiol group (e.g. by the thiolactonization which is discussed above) if it did not originally posses such a free thiol group. Such modification is described in Example XXV below. The reaction produces a thioether linkage by alkylation of the free-thiol (sulfhydryl) group.

It may be seen from an observation of the formulae of Structures (IV), (V), (IX), (X), (XI), (XII), (XIII), and (XIV) that a Cys amino acid, which in a reduced state provides an SH reactive group, is located at either the C-terminal or N-terminal of the peptide structure. This location permits the peptide to be chemically linked to carrier molecules at either terminus. Moreover, the Structures (XIV), (X), (IX), (X), (IV) have a six-proline spacer chain $(Pro)_6$ between the cysteine residue and the remainder of the peptide sequence. This latter arrangement provides a chemical spacer between the coupled carrier and the sequences representing a fragment of the natural hormone. A six-proline spacer can be added as a side chain spacer, for example at position 122 (lysine) in Structure (II), by initially adding an SH group (thiolactonization) to the free or unblocked epsilon amino group on this (lysine) residue, as set out in Example XXIX below. Then, utilizing the activator A or B in FIG. 9 in which the component "X" is a chain of six proline amino acids, conjugation can be carried out. In the latter case, a spacer is provided between the carrier and peptide linked at an intermediate site, for example at position 122 in Structure (II). In the former case, only the spacer derived from the conjugating reagent links the carrier and peptide.

Modifying groups, such as hemocyanin from Keyhole limpet, containing free amino groups can be prepared in buffer solution, such as phosphate buffer, in sodium chloride solution at a pH of 6–8. To this solution, tolylene diisocyanate (T.D.I.C.) reagent diluted from about 1–10 to about 1–40 times with dioxane is added to the modifying group. The general procedure was disclosed by Singer and Schick, *J. Biophysical and Biochem. Cytology*, 9, 519 (1961). The amount of T.D.I.C. added may range from 0.075 to 1,000 molar equivalents of the modifier used. The reaction may be carried out at about −5° to about +10° C., preferably 0° to 40 C., for about ½ to 2 hours. Any excess T.D.I.C. may be removed by centrifugation. The precipitate may be washed with the above-mentioned phosphate buffer and the supernatants combined.

This activated modifying group solution may then be combined with the hormonal or non-hormonal polypeptide to be conjugated. The polypeptide is dissolved in the same phosphate buffer (5–30 mg/ml) and the volume of modifier and polypeptide combined according to the molar ratio of the two desired in the conjugate. Combined solutions are reacted at 30°–50° C., preferably 35°–40° C., for 3–6 hours.

Separation of modified polypeptide and free unconjugated polypeptide may be accomplished by conventional techniques, such as gel filtration.

Picogram amounts of $I^{125}$ labeled polypeptide may be added as a tracer to the reaction mixture at the time of conjugation, and a quantity of polypeptide conjugated to modifying groups (molar ratio) may be determined by the amount of radioactivity recovered.

Included in the methods for modifying the hormones, non-hormonal proteins and their fragments (unmodified polypeptides) are conjugation by use of water-soluble carbodiimide. The amino groups of the unmodified polypeptide are first preferably protected by acetylation. This (acetylated) unmodified polypeptide is then conjugated to the modifier, such as a natural protein modifier, e.g. hemocyanin from Keyhole limpet, homologous serum albumin, and the like, or dextrans, Ficolls, or polytyrosine, preferably in the presence of guanidine, such as guanidine HCl, using 10-ethyl-3-(3-dimethylamino propyl) carbodiimide as activating agent. This method is generally disclosed by Hoare and Koshland, Jr., *J. of Biological Chemistry*, 242, 2447 (1967). If Ficoll 70 is used, it is preferred that it be first treated with ethylenediamine so as to render the final coupling more efficient. This treatment with ethylenediamine may be performed in a solvent such as saline and dioxane at about room temperature and a pH of about 9–12, preferably 10–11, for about ¼ to about 2 hours. The conjugation itself between the unmodified polypeptide and the modifier may be performed in a solvent such as glycine methyl ester while maintaining the pH at about 4–5, preferably about 4.5–4.8. The temperature of reaction is conveniently about room temperature and the reaction may be allowed to proceed for about 2–8 hours, preferably 5 hours. The resulting modified polypeptide of this invention may be purified by conventional techniques, such as column chromatography.

Modified polypeptides may also be prepared using glutaric dialdehyde as conjugating agent. According to a theory proposed by Richards and Knowles [*J. Mol. Biol.*, 37, 231 (1968)], commercial glutaric dialdehyde contains virtually no free glutaric dialdehyde, but rather consists of a very complex mixture of polymers rich in alpha, beta-unsaturated aldehydes. Upon reaction with natural protein modifiers such as homologous serum albumins, these polymers form a stable bond through the free amino group, leaving aldehyde groups free. This intermediate product then reacts with unmodified polypeptide in the presence of alkali metal borohydride, such as sodium borohydride. This intermediate is formed at pH 7–10, preferably 8–9, at about room temperature. The modified polypeptide is also conveniently obtained at about room temperature after about ¼–2 hours reaction time. The resulting product is recovered in pure form by conventional techniques, such as gel filtration, dialysis and lyophilization.

Polymerized sugar modifiers such as Ficoll 70 or Dextran T 70 may also be prepared for conjugation by treatment with a cyanuric halide, such as cyanuric chloride, to form a dihalotriazinyl adduct. The process may be performed in a solvent such as dimethylformamide at about 0°–20° C., preferably 10°–15° C., for about ½–4 hours. The resulting intermediate product may then be dialyzed until essentially halogen ion free, and lyophilized and treated with unmodified polypeptide at pH 8–11, preferably about 9–10, for about ½–12 hours at about 15°–35° C., conveniently at room temperature. The resulting modified polypeptide may be recovered as indicated above.

Said polymerized sugar modifiers may also be treated with an alkali metal periodate, such as sodium periodate, at a pH of 3–6 at about 30°–60° C. for about ½–4 hours, and the resulting intermediate conjugated with unmodified polypeptide at a pH of about 7–11, preferably about 8–10, for about ¼ to about 2 hours at a temperature of about 15°–80° C., preferably 20°–60° C. The resulting modified polypeptide of this invention may be separated as indicated previously.

The modifying groups may vary in chemistry and number for any given polypeptide structure. However, they will attach to only certain amino acid moieties. In particular, when modifying with diazo groups, such groups will chemically bond to only the histidine, arginine, tyrosine and lysine moieties or sites. Other modifying groups will bond to peptide molecules at different sites and in different numbers. Consequently, depending upon the size and chemical makeup of the particular modified polypeptide desired, one skilled in the art will readily be able to calculate the maximum possible number of modifying groups associable with a polypeptide. It is also recognized that several modifying groups may attach themselves to each other which in turn attaches them to a single amino acid moiety, but as used herein, reference to a number of modifying groups means the number of reaction sites to which a modifier has been attached.

Throughout the foregoing description, the term "modified" or "conjugated" has been utilized in referring to the chemical reaction by which the foreign molecules become chemically attached to specific sites on the polypeptide. Although specific mechanisms by which this is accomplished are described herein in detail, other appropriate mechanisms may be used if desired. It is clear that the modifier, i.e., the substance which modifies the relevant polypeptide, can be a physically larger molecule or fragment thereof than the molecule or fragment which it modifies. As noted above, such large molecules are deemed herein to be "carriers". Clearly, physical size of the fragment is not always critical, the criterion for effectiveness being that the mammalian body's reaction generate antibodies in sufficient quanta and specific to the targeted hormone or endogenous or non-endogenous protein.

POLYMERIZATION

The instant modified polypeptides may also be prepared by polymerization of the polypeptides from which they are derived, the term polymerization being used herein to cover dimerization, trimerization, etc. For example, the modified polypeptides of the invention may be prepared by polymerization of unmodified polypeptide using bi-functional imidoester. The imidoester, such as dimethyl adipimidate, dimethyl suberimidate and diethyl malonimidate, may be used to form the polymer in a manner similar to the generally described methods of Hartman and Wold, Biochem., 6, 2439 (1967). The polymerization may take place conveniently at room temperature in aqueous solvent at a pH of about 9–12, preferably about 10–11, over a period of ¼–2 hours.

The instant modified polypeptides may also be prepared by dimerization through a disulfide bond formed by oxidation of the thiol group on a cysteine residue using iodosobenzoic acid and methods corresponding to known methods, such as room temperature reaction for about 10–40 minutes.

These relatively unsophisticated dimerization and polymerization techniques tend, however, to suffer from serious disadvantages. Dimerization of the polypeptide via a disulfide bridge has the advantage of not introducing any exogenous material into the animal (in contrast to the techniques discussed above which involve introduction of exogenous carriers into the animal), but since the modified polypeptide administered to the animal is only a dimer of the unmodified polypeptide which is not itself immunogenic to the animal, such dimers may in some cases be unsuccessful in provoking useful levels of antibodies. Polymerization using a bi-functional coupling reagent such as an imidoester can provide a modified polypeptide large enough to be strongly immunogenic. Unfortunately, experiments have proved that straightforward application of the bi-functional organic reagent polymerization technique to either proteins or relatively large fragments thereof, which will often be required in practical use of this invention, produces very complicated mixtures of modified polypeptides having correspondingly complicated immunogenic properties. Furthermore, the immunogenic properties of the polymerized polypeptides thus produced are not readily reproducible, whereas such reproducibility is essential in any material intended for pharmaceutical use, since the necessary tests of safety and efficiency cannot be performed on non-reproducible material.

I have not found (though this knowledge is not disclosed in the published literature) that the reason for the very complicated immunogenic properties and the lack of reproducibility present in some polymers produced by the bi-functional organic reagent polymerization technique is that, notwithstanding the use of a bi-functional reagent, extensive cross-linking of the peptide tends to occur, such cross-linking presumably being due to the presence of free amino, thiol, carboxyl and perhaps other groups (the exact groups involved depending of course upon which groups the bi-functional organic reagent is capable of reacting with) at non-terminal positions on the polypeptide. Such cross-linking produces branching and 3-dimensional structure in the resultant polymers. Not only does the relatively random cross-linking thus produced render the structure of the polymers themselves unpredictable and non-reproducible, but such cross-linking may well alter the tertiary structure and shape of the unmodified polypeptide being polymerized, thus effecting its immunogenic properties (see the foregoing discussion of the importance of conformational determinants in the antigenic properties of polypeptides and proteins).

There is a further, although usually minor, disadvantage which is shared by both the bi-functional organic reagent polymerization technique and the conjugation technique, namely the introduction of exogenous materials into the body of the animal being treated. The bi-functional organic reagent technique introduces a relatively small proportion of exogenous material into the animal being treated (and even this relatively small proportion of non-endogenous material can be chosen so that it is not strongly immunogenic), while the conjugation technique tends to introduce a much higher proportion of non-endogenous material and will usually provoke the formation of substantial quantities of antibodies to the carrier as well as to the polypeptide. Although, as mentioned above, the formation of antibodies to the carrier (and in some cases to the bi-functional organic reagent used for coupling either in the conjugation or polymerization techniques) may sometimes be useful (for example, a vaccine based upon an HCG peptide coupled to diphtheria toxoid and intended for fertility control has the incidental advantage of also conferring protection against diphtheria), there are some occasions on which it may not be desirable to provoke the formation of relatively large quantities of antibodies to the carrier; for example if one wishes to use a vaccine containing a modified polypeptide of the invention to treat a patient with a carcinoma or a serious viral infection, it may be desirable to avoid overstraining the patient's immune system by challenging it not only with the modified polypeptide to which antibodies are desired, but also with the carrier.

Accordingly, it is greatly preferred that, when producing the instant modified polypeptides by the polymerization technique, the polymerization be effected in such a way that coupling of the peptide fragments being polymerized occurs only at or near the terminals of the fragments, thus producing a true linear polymer substantially free of non-linear polymers of the fragments.

It may at first appear surprising that a linear polymer of a polypeptide, the monomeric form of which is effectively non-immunogenic to an animal, can be immunogenic to the same animal. It is believed (though the invention is in no way limited by this belief) that the increase in immunogenicity upon polymerization is due to the increase in physical size of the molecule, which enables the molecule to be recognized much more easily by the animal's immune system. It can be shown that at least some monomeric polypeptides are very weakly immunogenic and cause the animal's immune system to produce detectable quantities of antibodies, which quantities, however are much too small to be effective. Immune systems are not well-adapted to recognize molecules as small as the small polypeptides when the polypeptides are present in polymeric form.

Although the optimum number of polypeptide fragments in the modified polypeptides will of course vary with the size of the individual fragments, the chemical nature of the fragments and perhaps the animal to which they are to be administered, in general I have found it convenient to use polymers containing from 4 to 14 fragments. In most cases, where it is desired only to affect a single hormone, it is simplest to use a polymer containing identical fragments, but it is not essential that all fragments of the polymer be identical and the fragments may be the same or different. For example, when it is desired to produce a polymeric polypeptide for use in provoking antibodies to HCG, two or more of the polypeptides of Structures (I) to (XIV) above could be polymerized together so that the resulting polymer contained several different immunological determinants of HCG. Indeed, it is not even necessary that all the polypeptides which are polymerized together necessarily be derived from the same protein; for example, if one wished to influence a complicated hormonal system controlled by several different hormones, one might polymerize fragments of two or more of the hormones to form the polymer.

Polymerization of the fragments to form the linear polymeric polypeptides of the invention may be effected in any manner for coupling peptide fragments to form linear polymers thereof known to those skilled in the art. The linear polymeric polypeptides of the invention may be divided into two distinct types. In the first type, the individual peptide fragments are linked head-to-tail by peptide linkages, so that the whole polymer comprises solely the fragments themselves and does not contain any extraneous material. Although such pure polymers do have the advantage of not introducing any extraneous material into the body of the animal being treated, they are usually too expensive to be practical, since the necessary fragments (whether produced by total synthesis or cleavage of a natural protein) are themselves very expensive and substantial losses occur during the polymerization process. Furthermore, the head-to-tail coupling of the fragments, without any intervening residues, may produce immunological determinants which have no counterpart in the unpolymerized fragment. For example, if the fragment described above, comprising the 105–145 sequence of HCG, is polymerized by means of peptide linkages, a sequence:

Pro-Ile-Leu-Pro-Gln-Asp-Pro-Leu-Thr will be produced at each junction between adjacent fragments, and this sequence may provoke the formation of antibodies which would not be produced by the fragment itself, and which may be undesirable. In colloquial terms, since there is not "punctuation" to tell the immune system of the recipient animal where one fragment begins and another ends, the animal's immune system may inadvertently start reading at the wrong residue and produce unwanted antibodies by running the sequences of adjacent fragments together. For this reason, in general, I do not recommend the use of linear polymers in which the fragments are connected by peptide polymers, though of course such linear polymers may be useful in certain instances.

Various methods of coupling polypeptide fragments via peptide bonds are known to those skilled in the art. For example, one fragment to be coupled may have its C-terminal carboxyl group blocked (e.g. by esterification) and be reacted with the other fragment, which has its N-terminal amino group blocked, but its carboxyl group activated by means of an activating agent. Obviously, blocking of non-terminal amino and carboxyl groups may be necessary. Also, as well known to those skilled in this field, it may be advantageous to attach one end of the polymer being produced to a support, such as polystyrene resin support, the polymer only being detached from the support after polymerization is completed.

In the second type of linear polymer polypeptide of the invention, the polypeptide fragments are connected to one another by means of residues derived from a bifunctional reagent used to effect polymerization of the fragments, so that the final linear polymer is an alternating linear polymer of polypeptide fragments and coupling reagent residues. Although this type of polymer necessarily introduces some extraneous material into the animal being treated, the proportion of extraneous material can be made considerably lower than it would be if the fragments were coupled to a large carrier, such as diphtheria toxoid. The coupling reagent, which is necessarily a bifunctional coupling reagent to produce a true linear polymer, can be chosen so that the residues it leaves in the polymer are not strongly immunogenic (so that they do not place the strain on the immune system of the recipient animal that, for example, a large carrier molecule such as diphtheria toxoid would) and the presence of these residues in the polymer has the advantage of substantially eliminating false immunological determinants produced by conjunction of the head of one fragment with the tail of an adjacent fragment, as discussed above.

To ensure that a true linear polymer is produced during the polymerization process, one terminal of a first polypeptide fragment is reacted with the bi-functional coupling reagent so that the coupling reagent reacts with a group present at or adjacent one terminal of the fragment; for example, the coupling reagent may react with a N-terminal amino group, a C-terminal carboxyl group or a free thiol group present on a C-terminal cysteine. Obviously, the nature of the coupling reagent used determines what group on the peptide reacts. In order to avoid any cross-linking and to ensure a reproducible product, it is important that only one site on the first fragment be available for reaction with the coupling reagent so that the coupling reagent can only attach to the first fragment at this one site. As those skilled in this field are aware, if it is desired to use a fragment containing more than one group which could react with the coupling reagent, the excess sites may be blocked by attaching suitable protective groups thereto. The product formed by reaction of the first fragment with the coupling reagent is then reacted with a second fragment (which may be the same as or different from the first fragment) having a single site available to react with the second reactive group of the bifunctional bicoupling reagent, thereby coupling the first and second fragments by a residue derived from the coupling reagent. Following any necessary purification of this dimeric product, it is then reacted with a further portion of a coupling agent which may be the same or different reagent from that used to effect the first coupling) thereby reacting the free terminal of either the first or second fragment with the coupling reagent. Naturally, it is important to ensure that only one site on the dimer is available for coupling to the coupling reagent, and as will be apparent to those skilled in the art, blocking or unblocking of potential reactive groups on the dimeric polypeptide may be necessary. The product of the reaction of the dimeric polypeptide with the coupling reagent is then reacted with a third fragment having only a single site available for reaction with the remaining reactive group of the coupling reagent, thereby producing a linear polymer containing three polypeptide fragments. Obviously, this process can be repeated until the desired size of linear polymer has been produced.

It will be apparent to those skilled in this field that the bifunctional coupling reagents used to prepare the linear polymeric polypeptides of the invention should be asymmetric i.e. they should have two functional groups which react with different groups on the fragments being polymerized, since, for example, if one attempted to react a bifunctional bicoupling reagent having two functional groups, which both reacted with amino groups, with a first fragment having a single amino group, at least some of the first fragment would be dimerized via a residue derived from the bifunctional bicoupling reagent. Such dimerization may in theory be avoided by using a very large excess of the coupling reagent, but in practice it is undesirable to run the risk of producing even a small proportion of dimer. Similarly, in later stages of the polymerization process, it will be even more undesirable to use symmetric coupling reagents, thereby running the risk of dimerizing the partially formed polymers already produced.

In the preferred process for producing the linear polymeric polypeptides of the invention already described, the polymer chain is begun with a first peptide having no unblocked thiol group and having an unblocked amino group only at its N-terminal (peptides containing thiol groups and/or amino groups other than at the N-terminal may of course be used if all these thiol and amino groups are blocked with any conventional blocking agent). This first peptide is then reacted with an amino group activating agent, a preferred activating agent for this purpose being 6-maleimido caproic acyl N-hydroxy succinimide ester (MCS); reaction of the peptide with this reagent is optimally effected at a pH of 6.6). The activating agent reacts with the amino group at the N-terminal of the first peptide to form an activated form of the first peptide; in the case of MCS, it is the ester portion of the reagent which reacts with the N-terminal group of the peptide. It is normally then necessary to remove excess activating agent before continuing the preparative process. Once the excess activating agent has been removed, the activated first peptide is reacted with a second peptide having a C-terminal cysteine in a reduced state (i.e. having an unblocked free-thiol group), thereby causing coupling of the N-terminal of the activated first peptide to the C-terminal of the second peptide via an activating agent residue. Desirably, the resultant dimer is purified as described in more detail below. Next, the dimer is again reacted with an amino-group activating agent and then with a second portion of the second peptide or with a third peptide, thereby producing a trimer. This procedure is repeated until the desired chain length has been achieved.

In order to secure reproducible responses from the immune systems of treated animals, it is important that the linear polymeric polypeptides of the invention be used in the form of pure polymers in which all the molecules contain the same number of fragments. To achieve such pure polymers, effective purification should be used after each polymerization step of the polymerization process. Because of the close chemical similarity between polymers containing different numbers of fragments, chemical purification is ineffective, so purification must be effected by physical methods. Gel filtration may be used if desired, but my preferred purification method is reverse-phase, high-pressure liquid chromatography, preferably using a molecular sieve as the solid phase.

In this method of forming linear polymers, the first and second peptides may be identical in chemical configuration except that in the first peptide the C-terminal cysteine has a blocked thiol group.

As already mentioned, two particularly preferred fragments for use in the linear polymeric polypeptides of the invention intended for provoking antibodies to HCG are:

```
Asp-Asp-Pro-Arg-Phe-Gln-Asp-Ser-Ser-Ser-

Lys-Ala-Pro-Pro-Pro-Ser-Leu-Pro-Ser-Pro-Ser-

Arg-Leu-Pro-Gly-Pro-Ser-Asp-Thr-Pro-Ile-Leu-

Pro-Gln-Cys (hereinafter designated fragment

A); and

Asp-His-Pro-Leu-Thr-Cys-Asp-Asp-Pro-Arg-Phe-

Gln-Asp-Ser-Ser-Ser-Lys-Ala-Pro-Pro-Pro-

Ser-Leu-Pro-Ser-Pro-Ser-Arg-Leu-Pro-Gly-Pro-

Ser-Asp-Thr-Pro-Ile-Leu-Pro-Gln-Cys
```

These first two preferred fragments for forming linear polymeric polypeptides of the invention to form antibodies to HCG mentioned above may be described as (111–145)-Cys and (105–145)-Cys, where the figures refer to the amino acid sequence in the beta subunit of HCG. It will be appreciated that, when these fragments are to be used in forming linear polymeric polypeptides of the invention by the method just described, the lysine residue at position 122 must have its amino group blocked and, in the case of the (105–145)-Cys fragment, the non-terminal cysteine at position 110 must have its thiol group blocked, preferably with an acetamidomethyl group.

It will be noted that some of the polymerization techniques discussed above require the presence of a C-terminal cysteine on the peptide. Obviously, if it is desired to use a peptide which lacks a C-terminal cysteine as a second or later fragment in preparing the linear polymeric polypeptides of the invention by the preferred techniques discussed above, it will be necessary to add a C-terminal cysteine to the peptide; appropriate methods for doing so are of course well known to those skilled in the field of polypeptide synthesis. Also, some peptides may of course require blocking of non-terminal amino and/thiol groups before use.

MISCELLANEOUS TECHNIQUES FOR MODIFYING POLYPEPTIDES

Numerous other techniques for the chemical modification of polypeptides may be employed in the practice of this invention. For example, naturally occurring proteins or polypeptides may be modified by removal of moieties therefrom. Some natural proteins have carbohydrate residues, especially sugar residues, attached to the protein chain and these carbohydrate residues may be removed according to methods known in the art, for instance by use of N-acetyl neuriminidase or N-acetyl glucosidase, materials known to be used for removal of specific carbohydrate residues.

Modification of the conformation of natural proteins by the breaking of disulfide bridges therein has already been referred to above in connection with the choice of polypeptide to be modified in the instant invention. However, it should be noted that in some cases breaking of an appropriate number of disulfide bridges within a protein may itself comprise a sufficient modification to render the protein much more immunogenic, and hence constitutes a sufficient chemical modification of the protein within the meaning of the instant invention. For example, as already mentioned, the natural form of beta-HCG contains 12 cysteine residues linked to form six disulfide bridges and any number of these bridges may be broken using known techniques, as set out for example in:

Bahl, *Biochem. Biophys. Res. Comm.*, 70, 525–532 (1976).

This particular article describes cleaving 3–5 of the six disulfide bridges in the beta subunit of HCG, but the same techniques may be used to break all six bridges if so desired.

ADMINISTRATION OF THE INSTANT MODIFIED POLYPEPTIDES

Obviously, in order that the modified polypeptides of the invention can provoke the formation of antibodies to the target protein within the body of an animal, they must be administered to the animal in such a way that they can come into contact with the cells responsible for formation of antibodies. In practice, this essentially means that the modified polypeptides must be introduced into the circulatory system of the mammal to which they are administered. Although the use of other modes of administration is not absolutely excluded, in view of the molecular size and weight of most of the instant modified polypeptides likely to be used in practice, the normal route or administration will be parenteral administration i.e. by injection. In the vast majority of cases, the quantity of modified polypeptide which will need to be administered will be far too small for convenient handling alone, and in any case the chemical nature of most of the modified polypeptides prevents them being produced in a pure form free from liquid vehicles. Accordingly, it is normally necessary to administer the modifying polypeptides of the invention as a vaccine comprising a modified polypeptide together with a vehicle. As already mentioned, a preferred vehicle for administration of the instant modified polypeptides comprises a mixture of mannide monooleate with squalane and/or squalene. It has been found that this vehicle has the effect of increasing the quantity of antibodies provoked by the linear polymeric polypeptide, antigen or modified antigen of the invention when the vaccine is administered to an animal. To further increase the quantity of antibodies provoked by administration of the vaccine, it is advantageous to include in the vaccine an immunological adjuvant. The term "adjuvant" is used in its normal meaning to one skilled in the art of immunology, namely as meaning a substance which will elevate the total immune response of the animal to which the vaccine is administered i.e. the adjuvant is a non-specific immunostimulator. Preferred adjuvants are muramyl dipeptides, especially:

NAc-nor Mur-L.Ala-D.isoGln

NAc-Mur-(6-0-stearoyl)-L.Ala-D.isoGln or

NGlycol-Mur-L.alphaAbu-D.isoGln

Thus, vaccines of this invention may be administered parenterally to the animals to be protected, the usual modes of administration of the vaccine being intramuscular and sub-cutaneous injections. The quantity of vaccine to be employed will of course vary depending upon various factors, including the condition being treated and its severity. However, in general, unit doses of 0.1–50 mg. in large mammals administered from one to five times at intervals of 1 to 5 weeks provide satisfactory results. Primary immunization may also be followed by "booster" immunization at 1 to 12 month intervals.

To prepare the vaccines of the invention, it is convenient to first mix the modified polypeptide, antigen or modified antigen of the invention with the muramyl dipeptide (or other adjuvant) and then to emulsify the resultant mixture in the mannide monooleate/squalene or squalane vehicle. Squalene is preferred to squalane for use in the vaccines of the invention, and preferably about 4 parts by volume of squalene and/or squalane are used per part by volume of mannide monooleate.

As already noted, the modified polypeptides of this invention may be administered parenterally to the animals to be protected, preferably with a pharmaceutically acceptable injectable vehicle. They may be administered in conventional vehicles with other standard adjuvants, as may be desirable, in the form of injectable solutions or suspensions. As indicated earlier, the adjuvant serves as a substance which will elevate total immune response in the course of the immunization procedure. Lipasomes have been suggested as suitable adjuvants. The insoluble salts of aluminum, that is aluminum phosphate or aluminum hydroxide, have been utilized as adjuvants in routine clinical applications in man. Bacterial endotoxins or endotoxoids have been used as adjuvants as well as polynucleotides and polyelectrolytes and water soluble adjuvants such as muramyl dipeptides. The adjuvants developed by Freund have long been known by investigators; however, the use thereof is limited to non-human experimental procedures by virtue of a variety of side effects evoked. The usual modes of administration of the entire vaccine are intramuscular and subcutaneous.

DESCRIPTION OF THE PREFERRED EMBODIMENTS

EXAMPLE I

This example illustrates the preparation of modified polypeptides of the invention based upon primate reproductive hormones and the use of such modified polypeptides in altering the level of reproductive hormones in baboons.

Adult female baboons were studied for at least one menstrual cycle for patterns of urinary estrogens, plasma, progestin, and in some cases urinary LH. Only those animals displaying normal patterns of these hormones were immunized. The criteria for normality and the procedures for housing animals are well known and will not be described.

GONADOTROPIN PREPARATIONS

Human Luteinizing Hormone (HLH)-partially purified preparation from human pituitaries with a biological potency of 2.5 units per mg. (NIH-LH-SI).

Human Follicle Stimulating Hormone (HFSH)-a partially purified preparation from human pituitaries with a biological potency of 86 units per mg. (NIH-FSH-SI).

Human Chorionic Gonadotropin (HCG) -a highly purified preparation from human pregnancy urine with biological potency of 13,200 IU/mg. (2nd IRP-HCG).

Monkey Luteinizing Hormone (MLH) -a crude preparation from rhesus monkey pituitaries with a biological potency of 0.75 units per mg. (NIH-LH-SI).

Ovine Luteinizing Hormone (OLH) (NIH-LH-S5).

Baboon Luteinizing Hormone (BLH) -partially purified baboon pituitary preparation with a biological potency of 1.1 units per mg. (NIH-LH-S1).

All preparations, excepting the OLH, were prepared in the inventor's laboratory. LH and HCG biological activity was determined by the ovarian ascorbic acid depletion test and the FSH preparation assayed by the ovarian augmentation assay.

The hormones were chemically modified by coupling with a hapten in varying ratios of hapten to hormone as described by Cinader et al., supra. For convenience, the Cinader process is discussed herein although Phillips, supra, may provide a more stable bond under certain circumstances. In this procedure, the protein hormone serves as a carrier and the hapten is coupled to it by diazo bonds. Although a variety of hapten groups were coupled to different hormones, the same basic procedure was used for any combination. Fifteen to thirty-five haptenic groups per hormone molecule were found most useful for preparing immunizing antigens. The basic reaction consisted of diazotizing the hapten (sulfanilic acid) by adding it to a solution of 0.11N.HCl and then slowly adding this solution dropwise to a 1 percent solution of $NaNO_2$ with constant stirring at 4° C. Diazotization was considered complete when free $HNO_2$ was detected in the reaction mixture. Although the above reaction was accomplished at 4° C., optimum temperatures of the reaction normally are about 0°–6° C., although 4° C. is preferred.

The hapten-protein coupling was performed by dissolving the protein hormone in an alkaline buffer, pH 8.0. The diazotized hapten was added slowly to the hormone solution with continuous stirring at 4° C. The pH of the reaction was constantly monitored and kept near 8.0. After all the hapten had been added, the pH was finally adjusted to 8.0, and the reaction mixture was stirred for 1–2 hours and allowed to stand at 4° overnight. The mixture was thoroughly dialyzed for 6–8 days against distilled water to remove unreacted hapten.

Although the number of diazo groups per hormone molecule could be regulated by the number of moles of hapten and hormone reacted, a parallel control experiment, with $S^{35}$ labelled sulfanilic acid to evaluate the precise composition of the hapten-protein samples, was performed with each diazotization. The same hormone preparation to be used for immunization was used in the control experiment. After the reaction was completed, an aliquot was taken from the reaction mixture and the remainder thoroughly dialyzed. Equal volumes of the dialyzed and undialyzed solutions were counted by liquid scintillation. By comparing the counts of the dialyzed and undialyzed samples, the moles of hapten coupled to each mole of hormone were calculated since the unreacted hapten was removed by dialysis. For this calculation, a molecular weight of 30,000 was assumed for all gonadotropin preparations.

Following dialysis, hapten-hormones were lyophilized and stored at 4° C. Diazo-HCG (35 groups/molecule) and HLH (26 groups/molecule) were bioassayed by the ovarian ascorbic acid depletion method and found to retain 62 and 85 percent respectively of the activity of the unaltered hormones from which they were derived. None of the other hormones was assayed for biological activity.

IMMUNIZATION PROCEDURES

Female baboons received their initial immunization on days 3–5 of the menstrual cycle and the second and third injections one week apart. The fourth injection was given 2–3 weeks after the third. A few animals received a fifth injection at 70–80 days after the first injections. All antigens were administered subcutaneously in a suspension of mannide monooleate or peanut oil. Doses of antigens for each injection varied between 3 and 5 mg. Injection sites were inspected daily for 5 days after each immunization for local reactions.

MONITORING EFFECTS OF IMMUNIZATION

Daily 24-hour urine specimens and frequent serum samples were collected during at least one menstrual cycle prior to immunizations and following immunizations until the effects of treatment were assessed. Urinary LH, urinary estrogens and plasma progestins were measured. Antibodies were detected in post-immunization serum samples by reacting 0.2 ml. of a 1:1000 dilution of serum in phosphate-buffered saline (pH 7.4) 0.5 percent normal baboon serum with 250 pg of $1^{131}$ labelled hormone. Sera were reacted with both the unaltered immunizing hormone and unaltered baboon LH for antibody detection. A purified baboon LH preparation (1.9×NIH-LH-S1) was used as a tracer antigen. Antigen-antibody complexes were precipitated with ovine anti-baboon gamma globulin after a 24-hr. incubation at 4° C. Antibody levels were expressed as pg of labelled hormone bound. Significant antibody levels were considered to be those that would bind 5.0 pg or more of the $1^{131}$ labelled antigen.

Antisera were fractionated by gel filtration on Sephadex G-200 according to the procedure of Fahey and Terry (at p. 36, *Experimental Immunology*, F. A. Davis Co., Philadelphia, Pa., 1967, incorporated by reference to the extent necessary to understand the invention) to determine the proportion of IgM and IgG antibodies in the baboon sera. Since the IgG fraction in this procedure contained a portion of IgA and IgD antibodies, only IgM and total titers were determined. The IgM fraction from the column was reacted with $I^{131}$ hormones and the binding capacity determined. The volumes of the fractionated sera were adjusted so that antibody levels would be comparable to those of whole serum.

ANTIBODY PRODUCTION

No significant reactions were observed at the site of injection following any immunization. On 4 occasions, a slight induration (2–3 cm in diameter) was seen when mannide monooleate was used as a vehicle but the redness and swelling disappeared within 4–5 days. Antibodies were detected against the immunizing antigen within 3–5 weeks in all animals. The extent, duration and cross reactivity of these antibodies is recorded. Generally speaking, higher levels were observed to heterologous gonadotropin immunization than to homologous ones.

The cross-reactivity of induced antibodies with baboon LH was studied on each animal. Cross-reactivity of antisera at peak levels was recorded. Although relatively high antibody activity against human LH and HCG was seen, relatively little reaction with baboon LH occurred. An intermediate cross-reaction was noted with anti-ovine LH and a high degree of cross-reactivity was seen with anti-monkey LH. Diazo-human FSH was weakly antigenic in the baboon. The duration of antibody production was generally longer with the human and sheep gonadotropin immunization than with those of monkey or baboon origin.

Peak antibody levels usually occurred at the time when the antibodies had shifted to principally the IgG type. Early antibodies had a larger proportion of IgM type and were generally more cross-reactive with baboon LH. The change in the proportion of the total antibody population with IgM was recorded from the time antibodies were first detected. Significant cross-reactivity to baboon LH was observed in anti-human gonadotropins when IgM was abundant but dropped sharply as the antisera shifted to nearly all IgG. This drop in cross-reactivity did not occur with monkey and baboon immunizations. Again, the ovine LH immunizations produced an intermediate change in reactivity with the shift from IgM to IgG.

EFFECTS ON THE MENSTRUAL CYCLE

The effects of immunization upon the event of the menstrual cycle were determined by observing changes in sex skin turgescence and levels of pituitary and/or ovarian hormones. Based on these parameters, the delay or retardation of ovulation from the expected time, as judged by the control cycle, was calculated. One animal immunized with HCG had no interruption in ovulation and another immunized with HFSH was delayed for only one cycle. Two animals injected with HLH and two injected with HCG had ovulation delays equivalent to two menstrual cycles. A third animal immunized with HLH was delayed a calculated 86 days. Ovine LH immunizations produced an 88 day delay in ovulation.

Immunizations with diazo-monkey or baboon LH resulted in longer disruption of the menstrual cycle. Calculated delays in ovulation for the two animals receiving monkey LH were 146 and 122 days, whereas the animals receiving altered baboon LH were retarded from ovulation 224 and 210 days.

Effects on specific hormone patterns following immunization with HLH in one animal were recorded. The interval between menses was considered to represent a "cycle". Urinary estrogens and plasma progestin patterns indicated that no ovulation occurred during the cycle of immunization which was 85 days in duration. Urinary estrogens were elevated during treatment but did not reflect a typical pattern. Plasma progestin were not elevated until about day 19 of the first post-treatment cycle. Antibody levels were elevated from about day 35 of the treatment cycle until 289 days from the first detection of antibodies. An LH assay was not available when this animal was studied and no data on plasma or urinary levels of this hormone were obtained.

Hormonal patterns following an immunization with diazo-baboon LH were recorded. In this animal, antibody levels were lower and persisted, in general, for a shorter period than did immunizations with human gonadotropins. During the treatment cycle, levels of urinary estrogens and plasma progestins followed a normal pattern but were quantitatively lower than normal. Urinary LH patters fluctuated markedly due to the injections of diazo-LH during this period. No conclusive evidence of ovulation was obtained for the treatment cycle. The first post-treatment cycle lasted 246 days. During this cycle urinary LH and estrogens were elevated on days 35–41 but there was no subsequent elevation in plasma progestins that would indicate ovulation had occurred. Following day 42 of this cycle, there was no significant elevation in any of the three hormone levels until day 231 when significant elevations of urinary estrogens and LH occurred. These rises were followed 3 days later by an elevation in plasma progestins indicating the presence of a functioning corpus luteum. A second post-treatment menstrual cycle was of normal duration and the endocrine patterns were normal.

Antibodies to unaltered baboon LH attained maximum levels by about day 70 of the post-treatment cycle and remained relatively constant until day 190 when a steady decline was observed. By day 215 of this cycle, antibody levels were barely detectable. Approximately 16 days after this time, a peak of LH commensurate with a normal midcycle elevation was observed. From this point the animals appeared to have the normal function of the pituitary-ovarian axis. Hormonal patterns in animals with other heterologous gonadotropin immunizations were similar to the animal receiving HLH and other animals receiving monkey or baboon LH were similar in response to the animal receiving baboon LH.

These results in baboons indicated that the modification of a reproductive hormone, by the procedures outlined, did render it antigenic and the antibodies thus formed did neutralize natural endogenous hormones if the natural hormone was obtained from the species receiving the immunizations with modified hormone.

EXAMPLE II

This example illustrates the preparation of a modified polypeptide of the invention derived from HCG and its effect on the levels of reproductive hormones in a human female.

HCG is a hormone naturally present only in pregnant women with the exception that an entity at least analogous thereto has been found to be present in humans in conjection with neoplasms. HCG is also commercially available. Human LH is immunologically and biologically identical to HCG even though there are chemical differences. Since they are biologically identical and HCG is readily available from commercial sources it was presumed that the effectiveness of this immunological procedure could be evaluated by injecting modified HCG into nonpregnant women and monitoring the blood levels of LH. Antibodies formed will neutralize both the LH and the modified HCG. Reference in the above regard is made to the publications identified earlier herein.

Women have a pattern of LH levels; the level is substantially constant until the middle period between menstrual cycles, immediately prior to ovulation; at that point the LH level rises greatly and helps induce the ovulation. Monitoring the LH level and the antibody level will show that the procedure used did or did not cause the production of antibodies capable of neutralizing the endogenous reproductive hormone, namely LH.

A woman aged 27 years was selected for study. Hormone was obtained, purified and modified as described in more detail below. The modified human hormone (HCG) was injected into the subject. It is well known that antibodies to HCG react identically to LH as well as HCG. The effect of the immunization was evaluated, principally by monitoring blood levels of LH. Finally the results were evaluated.

PREPARATION OF HORMONE

Clinical grade HCG derived from pregnancy urine was obtained from the Vitamerican Corp., Little Falls, N.J. This material has an immunological potency of 2600 IU/mg. Contaminants were detected in this preparation. Purification consisted of chromatography and elution. Fractions were dialyzed and lyophylized. The most potent fraction contained approximately 7600 IU/mg.; however, it was heterogeneous on polyacrylamide gel electrophoresis.

The fraction was further purified by gel filtration. The elution profile revealed two major protein peaks. The most potent HCG was found in the first peak and had an immunological potency of 13,670 IU per mg. This fraction was subjected to polyacrylamide gel electrophoresis. Further purification by gel filtration showed no evidence of heterogeneity of the HCG at this stage. Consequently, materials for study were processed according to the above procedure.

The contamination of this purified HCG was tested with $I^{131}$ used for identification and a sample was reacted with antisera against several proteins offering potential contamination. Those proteins were follicle stimulating hormone, human growth hormone, whole human serum, human albumin, transferrin, alpha one globulin, alpha two globulin and orosomucoid. No detectable binding of the purified HCG was observed with any antisera at a dilution of 1:50 of each. These negative results, calculated against potential binding of the respective proteins, indicated that contamination if any was less than 0.005 percent.

ALTERATION OF HORMONE

Hormone was altered by coupling with a hapten (sulfanilazo). This method couples the hapten molecules to the protein via the amino group of the aliphatic or aromatic portion of the hapten. The number of hapten molecules coupled to each HCG molecule (Ha-HCG) could be regulated and for this study, forty haptenic groups per HCG molecule were used for preparing the immunizing antigen.

Following the hapten-coupling process, the Ha-HCG was sterilized and tested.

SUBJECT

The subject was multiparous and had terminated her reproductive capabilities by prior elective bilateral salpingectomy. She was in good health and had regular cyclic menstruation. She underwent complete history, physical examination and laboratory evaluation including blood count, urinalysis latex fixation and Papanicolaou smear. She had no history of allergy.

To demonstrate normal functioning of the pituitary-ovarian axis prior to immunization, blood samples were obtained every other day from the first day of menses for 10 days, then daily for 10 days and finally, every other day until the next menses. Serum determinations of FSH, LH estrone, estradiol and progesterone were performed. These studies indicated an ovulatory pattern. IMMUNIZATION PROCEDURES Ten mg. of the Ha-HCG antigen were dissolved in 1.0 ml. of saline and emulsified with an equal volume of oil. Prior to injection, scratch tests to antigen and vehicle were performed. Immunizations were begun in the luteal phase of the treatment cycle to prevent superovulation from the administered HCG. Four injections at two week intervals were given to the subject. The first two of these were administered in oil subcutaneously (1.0 ml in each upper arm) the final two injections were given in saline only via the intradermal route. Following each injection, blood pressure readings were taken and the subject observed for allergic reactions.

MONITORING EFFECTS OF IMMUNIZATIONS

Blood samples were collected at weekly intervals beginning two weeks after the initial injection to test for the presence of humoral and cellular antibodies. Following completion of the immunization schedule, blood samples were collected in the same manner as in the control cycle to assess effects of immunization on hormonal patterns of the menstrual cycle. Since antibodies to HCG react identically to LH as with HCG, LH was monitored as an index of effectiveness of the procedure. A third cycle was similarly studied six months after initial immunization. Upon completion of the study, physical and pelvic examinations and laboratory evaluations were repeated.

Serum samples from the control and post-treatment cycles were assayed for FSH, LH, estrone, estradiol and progesterone.

The subject was tested for delayed hypersensivity before immunization and at two week intervals until the injection schedule was completed by an in vitro lymphocyte transformation test.

RESULTS

Temporal relationships of serum pituitary and gonadal hormones in the control cycles of the subject were recorded. Antibody titers to HCG were detected in the subject after two injections. Menses occurred at regular intervals during the immunizations.

Following the initial injection in mannide monooleate, some itching and swelling at the injection site occurred. Subsequent intradermal injections in saline produced no reactions and it was concluded that the local reactions were induced by the mannide monooleate. Lymphocyte transformation tests on plasma samples were negative.

In the post-treatment cycle, baseline follicular and luteal phase LH levels were not noticeably changed in the subject. Very small midcycle elevations in LH levels were observed as compared to the normal large increases. FSH patterns in the post-treatment cycle were normal. This indicated that the antibodies were neutralizing the action of endogenous LH.

The subject showed no ovulatory progesterone pattern but attained relatively high antibody titers to LH and HCG after only two injections of Ha-HCG.

The subject was studied during another cycle approximately six months from the first immunization. Significant antibody titers were found. LH patterns indicated a small midcycle elevation. FSH patterns were essentially normal. Thus, the specificity of anti-HCG antibodies to LH was shown but not to FSH.

The following Examples III–VII illustrate further experimental results obtained by administration of the vaccine prepared in Example II above.

EXAMPLE III

Another woman aged 29 years was selected for further study. Hormone was obtained, purified, and modified as in Example II. This modified hormone was injected into this subject in the same way as in Example II. The subject was monitored and tested as in Example II.

The results were similar to the results found in Example II except that (1) the levels of estrone and estradiol were substantially normal, (2) the subject acquired significant antibody titers late in the post-immunization cycle, and (3) in the cycle studies after six months this subject showed no significant midcycle elevation in LH patterns.

EXAMPLE IV

Another woman aged 29 years was selected for further study. Hormone was obtained and purified and modified as in Example II. This modified hormone was injected into this subject in the same way as in Example II. The subject was monitored and tested as in Example II.

The results were similar to the results found in Example II except that (1) baseline follicular and luteal phase LH levels were noticeably depressed in the post-treatment cycle, (2) no midcycle elevations were observed in LH, (3) estrone levels were elevated during the follicular phase of the post-immunization cycle, and (4) during the six-months' study there was no significant midcycle elevation in LH patterns.

EXAMPLE V

Another woman aged 35 years was selected for further study. Hormone was obtained, purified, and modified as in Example II. This modified hormone was injected into this subject in the same way as in Example II. The subject was monitored and tested as in Example II.

The results were similar to the results found in Example II except that (1) baseline follicular and luteal phase LH levels were noticeably depressed in the post-treatment cycle, (2) a very small midcycle elevation of LH was observed, (3) levels of FSH patterns in the post-treatment cycle were depressed, and (4) levels of both estrone and estradiol were reduced during the follicular phase of the post-immunization.

EXAMPLE VI

Another woman aged 28 years was selected for further study. Hormone was obtained, purified, and modified as in Example II. This modified hormone was injected into this subject in the same way as in Example II. The subject was monitored and tested as in Example II.

The results were similar to results found in Example II except that (1) baseline follicular and luteal phase LH levels were depressed in the post-treatment cycle, (2) no peaks were observed in the midcycle levels of LH, (3) estrone levels appeared elevated in the follicular phase of the post immunization cycle, and (4) LH patterns indicated no significant midcycle elevation in the six-month post-immunization cycle.

EXAMPLE VII

Another woman aged 28 years was selected for further study. Hormone was obtained, purified, and modified as in Example II. This modified hormone was injected into this subject in the same way as in Example II. The subject was monitored and tested as in Example II.

The results were similar to results found in Example II except that (1) antibody titers to HCG were not detected until after three injections, (2) baseline follicular and luteal phase LH levels were depressed in the post-treatment cycle, (3) no peaks nor midcycle elevation in the LH were observed, (4) estrone levels were elevated during the follicular phase, and (5) no significant antibody titers were found in the six month cycle.

All the above examples show the practicality of injecting modified hormones for the purpose of neutralizing an endogenous reproductive hormone and thereby offering a procedure for the prevention of conception or the disruption of gestation.

EXAMPLE VIII

Data obtained in earlier experiments and discussed in Examples I–VII showed that a modified natural reproductive hormone, when injected into an animal of species from which it was derived, would produce antibodies that would neutralize the action of the unmodified endogenous natural hormone in the body of the animal. Hormones used in Examples I–VII were FSH, LH and HCG. New experiments were performed, based on this knowledge, to identify another reproductive hormone (placental lactogen) that could be used in a similar fashion.

PREPARATION OF HORMONE

A purified preparation of placental lactogen was prepared from placentae of baboons since it was intended to use modified placental lactogen to immunize baboons. Placentae were extracted and purified by column chromatography according to previously published procedures. The purity was tested by polyacrylamide gel electrophoresis and by radioimmunoassay. The material obtained showed a high degree of purity on electrophoresis, and radioimmunoassay showed no contamination with other placental hormones.

HORMONE MODIFICATION AND IMMUNIZATIONS

The baboon placental lactogen (BPL) was altered by coupling with the diazonium salt of sulfanilic acid as outlined for other hormones in Example I. The number of diazo molecules per BPL molecule in this instance was 15. Immunization procedures were similar to those described in Example I for other hormones.

RESULTS

Within 4–6 weeks after the first injection of diazo-BPL, antibody levels to natural unmodified BPL in vitro were detected in 6 female baboons. Levels rose to a plateau within 8–10 weeks and remained there for several months. Hormonal measurements indicated that there were no effects on the normal events of the menstrual cycle due to the immunizations. Since BPL is normally secreted only in pregnancy, this was not a surprising observation.

All six females were mated with a male of proven fertility three times (once in each of three different cycles during the fertile period). Pregnancy diagnosis by hormonal measurement was performed after each mating. From the 18 matings, there were 13 conceptions as judged by pregnancy tests. The animals that were pregnant had menstrual bleeding 7–12 days later than was expected for their normal menstrual cycles. Subsequent hormonal measurements confirmed that these 13 pregnancies were terminated by abortions approximately one week after the time of expected menses.

The findings suggest that the antibodies formed in the animal's body after immunization had no effect on the nonpregnant menstrual cycle but when pregnancy was established, they neutralized the baboon placental lactogen in the baboon placenta and the result was abortion very early after conception.

When in Examples I–VIII above Structures (I), (II) and (III) are modified by use of a diazosulfanilic acid, dinitrophenol, or S-aceto mercaptosuccinic anhydride or structures (II) and (III) are modified by addition of polytyrosine or polyalanine, according to known methods, the results obtained should be similar to those in said Examples.

Similarly, when FSH, somatomedian, growth hormone or angiotension II are modified by use of diazosulfanilic acid or trinitrophenol, the results obtainable upon administration of the purified modified polypeptide into a male or female human or animal would indicate the stimulation of antibodies which neutralize all or some of the modified polypeptide as well as corresponding endogenous polypeptide.

EXAMPLE IX

This example illustrates the modification of levels of reproductive hormones in baboons following administration of modified polypeptides of the invention similar to those used in Example I above.

The subjects used in the studies reported in the example are female baboons. All baboons were adults of reproductive age. A description of subjects and the conditions of experimentation has been given in Example I. The animals were being studied using highly purified beta subunits of HCG using a preparation with a biological activity of less than 1.0 IU/mg. Animals were immunized with 14–26 moles/mole of polypeptide of diazosulfanilic acid coupled subunit in mannide monooleate.

Antibody levels were assessed by determining the binding of serum dilutions with $I^{125}$ labelled antigens. Cross-reactivity of antisera was measured by direct binding of labelled antigens and by displacement radioimmunoassays. Antifertility effects in actively immunized animals were tested by mating females with males of proven fertility. Effects in pregnant baboons passively immunized with either sheep or baboon anti-beta-HCG were determined by monitoring serum levels of gonadotropins and sex steroid hormones before and after immunizations.

Eight female baboons were immunized with the modified beta subunit of HCG. Significant antibody levels were attained in all animals.

Baboon immunizations with the modified beta subunit of HCG resulted in high antibody levels reacting to HCG, human LH and baboon CG but not to baboon LH. All animals remained ovulatory; however, no pregnancies resulted from numerous matings with males of proven fertility. Passive immunization of non-immunized pregnant baboons with sheep anti-beta-HCG serum produced abortions within 36–44 hours.

The following Examples X–XVI illustrate chemical modification techniques used to produce the modified polypeptides of the invention.

EXAMPLE X

Hemocyanin from Keyhole limpet (KLH) solution (7 mg/ml) in 0.005M sodium phosphate buffer 0.2M in NaCl, and of pH 7.5, is prepared. Insoluble particles are removed by centrifugation. To one ml. of this solution, tolylene diisocyanate (T.D.I.C.) reagent is added (20 microl.) diluted to 1/30 with dioxane, the amount being essentially the equivalent of the moles of lysyl residues in the KLH molecules. After 40 minutes at 0° C., the T.D.I.C. activated KLH solution is combined with 0.5 mg of synthetic beta-HCG peptide having the following structure:

Structure (XV)

Asp-His-Pro-Leu-Thr-Cys-Asp-Asp-Pro-Arg-Phe-

Gln-Asp-Ser-Ser-Ser-Ser-Lys-Ala-Pro-Pro-Pro-

Ser-Leu-Pro-Ser-Pro-Ser-Arg-Leu-Pro-Gly-Pro-

Pro-Asp-Thr-Pro-Ile-Leu-Pro-Gln-Ser-Leu-Prowhich is first dissolved in 25 microl of 0.05M sodium phosphate buffer 0.2M in NaCl, and of pH 7.5. The mixture is incubated at 37° C. for four hours. The resulting product is purified by gel filtration.

EXAMPLE XI

One g. of Ficoll 70 is dissolved in 1 ml each of normal saline and 2M ethylenediamine (adjusted to pH 10 with hydrochloric acid) solution. The solution is kept at room temperature in a water bath and stirred with a magnetic stirrer. Cyanogen bromide, 4 g, dissolved in 8 ml of dioxane, is added to the Ficoll 70 solution. The acidity of the mixture is maintained at pH 10–10.5 for 8 minutes by adding drops of 2N sodium hydroxide solution. An additional 2 ml of 2M ethylene diamine, pH 10, solution is added, and stirring at room temperature is continued for 30 more minutes. The product is purified by passing it through a Bio-Gel p-60 column.

EXAMPLE XII

Two mg of the compound of Structure (II) containing a picogram amount of $I^{125}$ labeled adduct and KLH (1.6 mg) is dissolved in 1 ml. of 1.0M glycine methyl ester in 5M guanidine hydrochloride. 19.1 mg. of ethyl dimethylamino propylcarbodiimide (E.D.C.) is added to this solution. The acidity is adjusted to and maintained at pH 4.75 with 1N HCl at room temperature for 5 hours. The KLH-peptide conjugate is purified by passing it through a Bio-Gel p-60 2.2×28 cm column equilibrated with 0.2M NaCl.

EXAMPLE XIII

Solid bifunctional imidoester dihydrochloride (3 mole) is added in 2 mg portions at 5-minute intervals to a constantly stirred solution of 1 mole of polypeptide of Structure (II) (1–20 mg/ml) in 0.1M sodium phosphate, pH 10.5 at room temperature. 0.1N Sodium hydroxide, is added to maintain the acidity at pH 10.5. One hour after the addition of the diimidoester has been completed, a polymerized product according to this invention is obtained.

EXAMPLE XIV

To a 20 mg/ml solution of homologous serum albumin in 0.1M borate buffer, pH 8.5, 1000% mole excess of 25% aqueous solution of glutaric dialdehyde is added at room temperature. The excess dialdehyde is removed by gel filtration in water using Bio-Gel p-2. The material collected at the void volume is lyophilized, and the dried product is redissolved in 0.1M borate buffer, pH 8.5 (20 mg/ml), mixed with the required amount of polypeptide of the following Structure:

Structure (XVIa)

Asp-Asp-Pro-Arg-Phe-Gln-Asp-Ser-Ser-Ser-Ser-

Lys-Ala-Pro-Pro-Pro-Ser-Leu-Pro-Ser-Pro-Ser-

Arg-Leu-Pro-Gly-Pro-Pro-Asp-Thr-Pro-Ile-Leu-

Gln-Ser-Leu-Pro 20 mg/ml) in the same buffer at room temperature. Twenty minutes later, sodium borohydride in 250 percent molar excess of polypeptide XVI is added. The reaction is terminated after one hour. The conjugated product is purified by gel filtration on, Bio-Gel p-60 column, dialyzed free of salt and lyophilized.

EXAMPLE XV 1 g of Ficoll 70, 500 mg of $NaHCO_3$, 3 g of cyanurin chloride, 20 ml of $H_2O$, and 80 ml of dimethylformamide, are stirred at a temperature below 16° C. for 22 hours. The product is dialyzed against distilled water until Cl-free, then lyophilized. 2 mg of the polypeptide of Structure (XV) containing a minute quantity of $I^{125}$ labeled analogue is incubated with 1 mg of this product in 0.25 ml of 0.2M. sodium borate buffer, pH 9.5, for one hour at 20° C., and the product is recovered from a Bio-Gel p-60 2.2×28 cm column.

When the above procedure is carried out and Dextran T 70 is used in place of Ficoll 70, the corresponding modified polypeptide, useful according to this disclosure, is obtained.

EXAMPLE XVI

Ficoll 70, 1.2 g of $NaIO_4$, and 0.42 g of KCl are dissolved in 1.5 ml of 1M sodium acetate buffer, pH 4.5, and incubated at 37° C. for 1 hour.

Two mg (=588 micro moles) of polypeptide of Structure (XV) containing a minute quantity of $I^{125}$ labeled analogue is incubated with 2 mg of the product obtained above in 0.3 ml of 0.2M borate buffer, pH 9.5 at 55° C. for 1 hour. The reaction mixture is then chilled in an ice-water bath and 1 mg of $NaBH_4$ 1 mg is then added into this solution. The reduction reaction is terminated by passing the product through the Bio-Gel p-60 2.2×28 cm column equilibrated and eluted with 0.2M NaCl.

EXAMPLE XVII

Numerous rabbits are immunized with a variety of synthetic peptides conjugated to different modifying groups. Following two or three immunizations at 3–5 week intervals, sera from animals are assessed by determining their ability to bind in vitro to radiolabeled HCG. The specificity of this binding is studied by reacting the same sera against other similarly labeled protein hormones, particularly pituitary LH. Sera are further assessed by determining their ability to inhibit the biological action of exogenously administered HCG in bioassay animals. Thus, the increase in uterine weight of the immature female rat in response to a prescribed dose of HCG is noted. The dose of HCG is administered subcutaneously in saline in five injections over a three day period and the animal is sacrificed for removal of the uterus on the fourth day. The weight of the uterus increases in dose responsive fashion with the hormone injections. When assessing the effects of antisera in this response, varying quantities of test serum are administered intraperitoneal separately from the subcutaneous injection of hormone during the assay. This procedure permits the antiserum to be absorbed rapidly into the rat's bloodstream and will permit interaction of it with hormone when the latter likewise enters this fluid. If the antiserum is capable of reacting with the hormone in a manner preventing stimulation of the uterus, the antiserum is considered to be effective for biological inhibition of hormone action.

The frequency of animals showing a positive response to immunological binding and neutralization of biological activity is documented in various of my publications.

EXAMPLE XVIII

Iodosobenzoic acid (dissolved in a slight excess of 1N potassium hydroxide) in 10% molar excess is added to the peptide of Structure (II) in phosphate buffer with normal saline at pH of 7.0. After thirty minutes at room temperature, the dimeric product polypeptide is purified by gel filtration.

EXAMPLE XIX

To an ice water bath cooled and vigorously stirred 0.23 ml. of bovine gamma globulin (10 mg/ml) in 0.05M phosphate buffer with normal saline (PBS) pH 7.5, 50 microl. of ⅒ T.D.I.C. in dioxane is added. After 40 minutes, the excess T.D.I.C. is removed by centrifugation (0° C., 10 minutes, 10,000 g) and the precipitate is washed twice with 0.1 ml of PBS. The combined supernatants are added to 7.7 mg of the peptide of Structure (II) dissolved in 0.8 ml. of PBS, pH 7.5. The mixture is stirred at room temperature for 10 minutes, then incubated at 37° C. for 4 hours. The conjugate product is purified by dialysis.

EXAMPLE XX

BSA (10 mg/ml) in PBS solution (0.25 ml.) is treated with 50 microl. of ⅒ T.D.I.C. dioxane solution and conjugated to 7.5 mg. of the synthetic beta-HCG peptide of Structure (III) in 0.8 ml. of PBS (pH 7.5) as in Example XIX to obtain the product.

EXAMPLE XXI

To an ice water bath cooled and vigorously stirred 0.6 ml. of beta-HCG peptide of Structure (III) (10 mg/ml) in phosphate buffered saline, pH 7.5, is added 30 microl. of ⅒ T.D.I.C. dioxane solution. After 40 minutes, the excess T.D.I.C. is removed by centrifugation (10,000 g, 0° C., 10 minutes) and the precipitate is washed twice with 0.1 ml. PBS. The combined supernatants are added to 3 mg of poly-(D, L-Lys-Als) dissolved in 0.3 ml. of PBS. The mixture is incubated at 37° C. for 4 hours. The product is then dialyzed and lyophilized.

EXAMPLE XXII

The results set out in Table I provide further evidence of the broad applicability of this invention as indicated previously in this specification.

Using standard methods of testing in rabbits, both immunological binding response and neutralization of biological activity were established for the modified polypeptides indicated with the results as set out in Table I.

TABLE I

Frequency of Positive Antibody Responses to Various HCG Peptide-Conjugates

| Peptide | Carrier | Immunized | Number of Rabbits Immunological Binding Responses | Neutralization of Biological Activity |
|---|---|---|---|---|
| 35 Amino Acid 111–145 | Bovine Gamma Globulin | 10 | 10 | 6 |
| Morgan et al. Peptide II | Keyhole Limpet Hemocyanin | 10 | 5 | * |
| 31 amino acid 115–145 | Poly-D-L-Alanine | 10 | 9 | 5 |
| Morgan et al. Peptide III | Bovine Serum Albumin | 12 | 12 | 6 |
| 44 amino acid 105–148 Peptide XV | Keyhole Limpet Hemocyanin | 10 | 8 | * |
| Natural 109-145 Keutman Peptide XII | Keyhole Limpet Hemocyanin | 10 | 10 | * |

*Additional time needed for assessment

EXAMPLE XXIII

Antigen was prepared by reacting a diisocyanate (T.D.I.C.-see above) coupling reagent with carrier (tetanus toxoid), extracting excess reagent and incubating the activated carrier with the peptide of Structure (II). Baboons were immunized with the antigen and results of mating 4 animals three times are shown in FIG. 1. The data in FIG. 1 show that from 12 exposures (matings) one pregnancy resulted even though relatively low levels of immunity from the antigen were achieved. Non-immunized baboons of the same colony had a fertility rate of approximately 85%.

EXAMPLE XXIV

Referring to FIG. 2, baboons were immunized initially with a beta subunit of HCG modified by diazotization in a manner similar to that described in conjunction with Example II. Following this initial administration, the baboons were injected 21 and 42 days later with the peptide of Structure (II) above which had been modified by the same diazotization process. FIG. 2 shows plots representing the levels of antibodies generated in consequence of these administrations. Such quantities of antibodies are expressed as micrograms of isotopically-labeled HCG that will bind each milliliter of serum from the baboons at specified days after the initial injection. The levels shown were maintained for a period of over one year.

TABLE 2

Breeding of Immunized Baboons
[Diazo-β-HCG presensitized]
Booster: Diazo-β-HCG-(111–145)

|  | 1 | | | 2 | | |
| --- | --- | --- | --- | --- | --- | --- |
|  | Pre-Mate Titer | Ovul. | Preg. | Pre-Mate Titer | Ovul. | Preg. |
| Mating No. 1 | 5.00 | + | − | 4.20 | + | − |
| Mating No. 2 | 4.25 | + | − | 4.10 | + | − |
| Mating No. 3 | 4.22 | + | − | 4.00 | + | − |
| Mating No. 4 | 4.17 | + | − | 3.89 | + | − |
| Mating No. 5 | 3.80 | + | − | 3.76 | + | − |
| Mating No. 6 | 6.65 | + | − | 5.00 | + | − |
| Mating No. 7 | 5.90 | + | − | 4.75 | + | − |
| Mating No. 8 | 5.10 | + | − | 4.20 | + | − |
| Mating No. 9 | 5.00 | + | − | 4.25 | + | − |
| Mating No. 10 | 4.66 | + | − | 4.00 | + | − |

In Table 2, the results of breeding the two baboons represented in FIG. 2 are revealed in tabular form. The Table presents the results of mating these animals ten times over a period of approximately one year. These data suggest that the animals ovulated in every cycle; however, no pregnancy was observed, as indicated by the animal having a menstrual period at or before the expected time therefor. While the results tabulated demonstrate the efficacy of the entire procedure, it was observed for the particular structure utilized in the primary immunization, i.e. Structure (II), antibody cross reactivity with LH was observed. Such cross reactivity may be avoided by the utilization of the fragment conjugation procedures set forth in detail hereinabove.

EXAMPLE XXV

Figure 3:
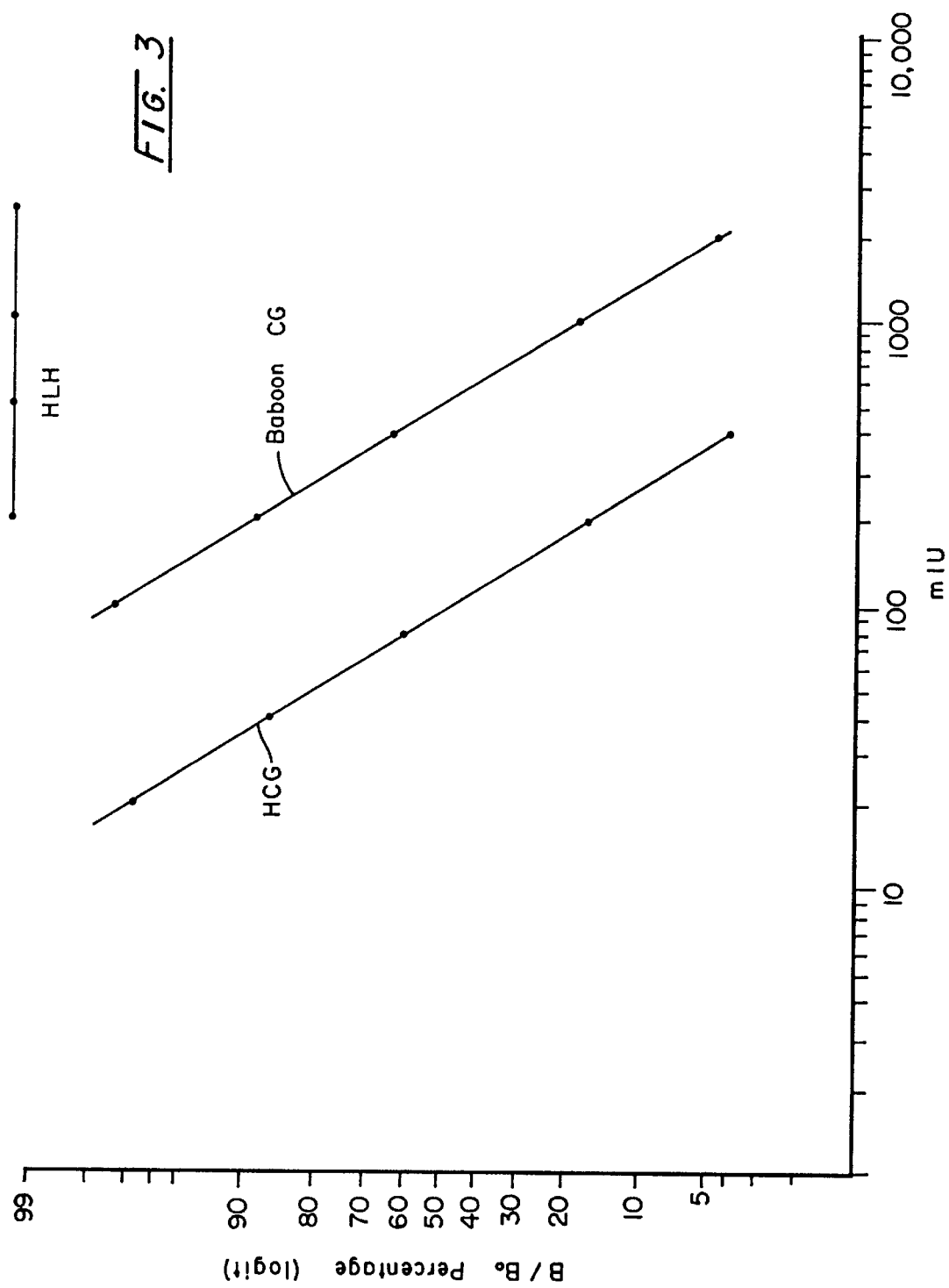
FIG. 3 shows three dose response lines illustrating the specificity of antibody response to a CG antigen formulated in accordance with the invention.

The specificity of antibody response to a CG fragment-macromolecular carrier is represented by the instant experiment. A 35 amino acid sequence [Structure (II), herein "synthetic peptide"] of the HCG beta subunit was conjugated with ovine gamma-globulin and administered to a baboon. Varying doses of each of these three hormones were tested for their ability to compete with $I^{125}$-labeled synthetic peptide of Structure (II) bound to the anti-serum. The results are set forth in FIG. 3. Note from the data in this figure that human LH was ineffective for displacement of tracer antigen at doses up to 2.5 IU (international units). Since HCG displaced antigen at a dose of 20 mIU, the cross-reactivity with HLH in this assay system was less than 0.8%. Baboon CG also displaced $I^{125}$-labeled antigen in this assay and, based on biological potency of the two hormones, was about 20% as effective as HCG.

EXAMPLE XXVI

The following experiments were carried out to determine whether the carbohydrate chains contained in the C-terminal 37 residues of beta-HCG influence the immunogenicity of that peptide.

A peptide representing amino acid residues 109–145 of beta-HCG was isolated from a chymotryptic digest of reduced and carboxymethylated beta-HCG by procedures reported by Keutmann, H. T.; Williams, R. M., J. Biol. Chem., 252, 5393–5397, (1977). This peptide is identified in Table 3 below as P-1. The purity of the peptide was confirmed by amino acid and terminal end group analyses. A portion of the isolated peptide was treated with anhydrous hydrofluoric acid (HF) to remove carbohydrate moieties and repurified by column chromatography according to methods described by Sakakibara S. et al., Bull Chem. Soc. Japan, 40, 2164–2167, (1967). This portion of the isolated peptide is identified in Table 3 as P-2. Complete removal of the sugar chains was confirmed by carbohydrate analysis; see Nelson Norton, J. Biol. Chem., 153, 375–380, (1944). A third peptide with the amino acid sequence 109–145 of beta-HCG was prepared synthetically using the solid state synthesis procedure of Tregear, G. W. et al., Biochem., 16, 2817, (1977). This third peptide is identified in Table 3 as P-3. Highly purified HCG was used in all immunological experiments where reference was made to intact HCG.

PREPARATION OF IMMOGENS AND IMMUNIZATIONS

Conjugates of the three peptides to keyhole-limpet hemocyanin (KLH) were prepared using tolylene diisocyanate. A peptide-carrier ratio of 4–6 peptides per 100,000 daltons of carrier was obtained for different conjugates prepared according to amino acid analyses. Rabbits were immunized with conjugates by three multiple site intramuscular injections of 1.0 mg. of conjugate in 0.5 ml. of saline emulsified with an equal volume of Freund's complete adjuvant. Injections were given at 3 week intervals and weekly blood samples were collected from 3–20 weeks of immunization.

EVALUATION OF ANTISERA

Antisera to all conjugates were monitored for antibody levels by reacting dilutions of sera with $I^{125}$ labeled HCG (Chloramine T method) at 4° C. for 5 days and precipitating immune complexes with sheep anti-rabbit gamma globulin serum. Antibody levels were determined by assessing dilution curves in which a linear correlation between dilution and binding of labelled antigen at equilibrium occurred. At least 3 points in each curve were used in calculating levels. These levels were expressed as micrograms of HCG bound per ml. of undiluted serum calculated by multiplying mass of labelled antigen bound by serum dilution.

A radioimmunoassay system employing $I^{125}$ HCG and antisera raised to peptide conjugates was used to determine the relative ability of HCG and peptides to compete with labeled HCG. Peak antibody levels from each rabbit were evaluated in these studies. Antigens and antisera contained in phosphate-buffered saline (pH 7.4) BSA (1%) were added to test tubes and incubated at 4° for 5 days. Separation of free and bound tracer HCG was accomplished by the addition of sheep anti-rabbit gamma globulin serum and then incubation for 48 hours followed by centrifugation. Assessment using methods described by Rodbard, D. in: Odell, W. D. and Daughaday, W. H., eds., "Competitive Protein Binding Assays", J. B. Lippincott, Phila, Pa. (1971). The ability of unlabeled HCG and peptides to compete with $I^{125}$ HCG for antibody binding sites was expressed as moles of unlabeled antigen, per mole of unlabeled HCG, required to reduce the binding of labeled HCG by 50%. For this purpose molecular weights for HCG, P-1, P-2, and P-3 of 38,000, 7,000, 3,990, and 3,990 respectively were used. The molecular weight of the P-1 peptide was an estimate since the contribution of the carbohydrate chains to its size was not determined. Four radioimmunoassays were performed with each of the 11 antisera studied and the results presented as the mean of the four values.

RESULTS

Parallel dose response curves of HCG and peptides were observed in all radioimmunoassays. In the assay system employed, 200–400 moles of unlabeled HCG was required per mole of labeled HCG at 50% binding of the latter to antisera. There was no detectable difference among antisera to the 3 peptide conjugates in the ability of intact HCG to compete with labeled hormone for antibody binding sites.

Data obtained from comparing the ability of HCG and peptides to compete with $I^{125}$ HCG for binding to anti-peptide sera revealed some qualitative differences in the antisera (Table 3). Much larger quantities of P-2 peptide and P-3 peptide were required to reduce $I^{125}$ HCG binding than were required than of the P-1 peptide when sera against the P-1 peptide were tested. While similar quantities of P-2 and P-3 peptides were required to inhibit one mole of labeled HCG binding, these were 2–10 times the amounts of the P-1 peptide required.

Differences in the quantities of peptides required to compete with an equivalent mass of labeled HCG were less using antisera raised to carbohydrate-free natural peptide (P-2). More P-1 peptide was needed for an equal reduction in binding than of the other 2 peptides. No significant difference could be detected in the quantities of P-2 or P-3 peptides required among the 3 antisera tested.

Approximately 1.5–2.0 times as much P-1 peptide was required to compete equally with $I^{125}$ HCG for antibodies raised to the P-3 peptide but P-2 peptide reacted nearly as well as did the synthetic peptide.

DISCUSSION

Despite low levels of antibodies obtained in this study, the carbohydrate-containing peptide was not more immunogenic than those without this moiety when conjugates to both were prepared in the same manner.

From these studies, it can be concluded that although antibodies to carbohydrate free peptides are qualitatively different from those to the natural peptide, antisera generated to the synthetic peptide reacted with HCG as well as anti-sera to natural peptides and equivalent to natural and synthetic peptides elicited similar anti-HCG levels in rabbits.

TABLE 3

Mean Quantities of HCG and 109–145 C-Terminal β-HCG Peptides Required to Compete with $I^{125}$ HCG at 50% Binding of Labelled Hormone

| Anti-sera | Unlabeled Antigens | | | |
|---|---|---|---|---|
| Rabbit No. | HCG mol/mol | P-1 mol/mol | P-2 mol/mol | P-3 mol/mol |
| | HCG $I^{125}$ (X ± SE) | HCG $I^{125}$ (X ± SE) | HCG $I^{125}$ (X ± SE) | HCG $I^{125}$ (X ± SE) |
| Anti P-1 | | | | |
| 78 | 284 (12.6) | 430 (11.8) | 4565 (200.8) | 3628 (154.1) |
| 79 | 350 (13.5) | 404 (18.5) | 855 (33.4) | 881 (42.2) |
| 171 | 403 (17.7) | 343 (9.9) | 899 (35.1) | 759 (37.1) |
| 173 | 377 (16.5) | 320 (13.9) | 1448 (72.4) | 1536 (73.7) |
| Anti P-2 | | | | |
| 93 | 247 (11.8) | 385 (18.2) | 264 (12.5) | 268 (12.73) |
| 94 | 294 (14.1) | 431 (15.5) | 362 (15.2) | 329 (13.8) |
| 252 | 201 (9.6) | 296 (12.4) | 216 (7.7) | 205 (9.0) |
| Anti P-3 | | | | |
| 405 | 496 (23.6) | 998 (47.4) | 628 (27.6) | 309 (13.6) |
| 411 | 489 (20.5) | 1200 (50.4) | 678 (29.7) | 413 (16.1) |
| 416 | 364 (13.1) | 581 (20.9) | 400 (14.4) | 271 (12.8) |
| 417 | 340 (14.9) | 474 (18.4) | 176 (6.8) | 105 (4.6) |

EXAMPLE XXVII

In this Example, a polypeptide fragment structure having an —SH group is activated utilizing the following reagent of Formula B shown in FIG. 9 in which X is a phenyl group substituted with a single methyl group ortho to the —$CON_3$ grouping. A solution of the reagent (1.2 eq. per —SH group in the polypeptide) in a suitable water miscible organic solvent, such as dioxane, is added to a solution of the polypeptide fragment, e.g. Structure (XII) (which has had its amino groups blocked) in aqueous buffer at pH 6.5. After 2 hours, the solvent is removed at a temperature of less than 30° C. under vacuum, and to the residue are added water and ethyl ether (1:1). The aqueous layer is separated and its pH adjusted to approximately 8.5 by the addition of sodium hydroxide solution and this alkaline mixture is added rapidly to an aqueous solution of the carrier, e.g. the above described influenza subunit, maintained at pH 8.5 by a suitable buffer. After a further 4 hours, the conjugate is isolated by gel filtration.

EXAMPLE XXVIII

With the following reagent of Formula C shown in FIG. 9 a solution or suspension of a carrier containing no sulfhydryl groups (such as flagellin) in a suitable aqueous buffer at a pH 6.5 is treated with the required (1.2 eq per —NH2 desired to be reacted) amount of a solution of the reagent in dimethylformamide. After 1 hour, the modified carrier is isolated by column chromatography and added to buffer at pH 6–7. This is then treated with a solution of the selected fragment (containing sulfhydryl groups) in the same buffer and the reaction is allowed to proceed for 12 hours before the conjugate is isolated by column chromatography.

EXAMPLE XXIX

Modification of non-sulfhydryl containing peptide fragments [e.g. Structure (II)] or a carrier such as flagellin to produce a sulfhydryl containing peptide via "thiolactonization" is carried out as follows:

The peptide is dissolved in a 1M aqueous solution of imidazole containing 0.5% of ethylenediaminetetraacetic acid at a pH of 9.3 under an atmosphere of nitrogen, and a 100 fold excess of N-acetylhomocysteine thiolactone is added in three portions at eight hour intervals. After a total of 30 hours, the pH is adjusted to 3–4 with acetic acid and the modified peptide is isolated by gel chromatography and elution with 0.5M acetic acid.

EXAMPLE XXX

The carrier protein is reacted with the N-hydroxysuccinimide ester of a halo-(either chloro, bromo or iodo) acetic acid in the general procedure described in the first part of Example XXVII thus yielding a modified carrier containing the required number of halomethyl alkylating groups as desired.

To a solution of the sulfhydryl containing peptide [e.g. Structure (XII)] in a phosphate buffer at pH 6.5–7.0 under nitrogen at room temperature is added an aqueous solution or suspension of the modified carrier prepared above. The mixture is stirred for 12 hours. It is then washed with ethyl acetate and the conjugate contained in the aqueous phase is purified by dialysis, gel chromatography and lyophilization.

Should neither the carrier nor polypeptide fragment contain a sulfhydryl group, one may be introduced into either of them by the standard procedures such as "thiolactonization" described above in Example XXIX.

EXAMPLE XXXI

This example illustrates the use of a modified polypeptide of the invention in repressing fertility in baboons.

A polypeptide of Structure (XII) above, identical to the residues 109–145 of beta-HCG, was prepared by total synthesis using the solid phase synthesis method described in Tregear et al, Biochem., 16, 2817, (1977). The purity of the peptide was assessed using thin-layer chromatography, high-voltage electrophoresis and amino acid analysis. The peptide was conjugated to the amino groups of tetanus toxoid via the cysteine residue at position 110 by the method described in Lee et al., Mol. Immunol., 17, 749, (1980). The resultant conjugated polypeptide contained 22 peptides per 100,000 daltons of the toxoid.

Male and female baboons (obtained from Primate Imports, Inc., Port Washington, N.Y.) were housed individually in metabolic cages measuring 89×94×114 cm (L×W×H) for females and 168×94×165 cm for males, each cage being equipped with a "squeezebar" mechanism for restraining the baboon. Each male baboon was housed in a separate room in which were also housed six to ten females. The room temperature was maintained at 21° C. with artificial light for 12 hours daily and the baboons were fed on Purina Monkey Meal (product of Ralston Purina, St. Louis, Mo.) mixed with corned beef, corn syrup and a vitamin mineral supplement; fresh fruit was given daily as a conditioning aid and water was provided ad libitum. Daily observations were made of each female baboon to establish the pattern of sex skin turgescence/deturgescence and menstrual bleeding.

In order to ensure that the results of the test described below were statistically valid, the number of baboons was determined using arcsine transformation of the projected fertility rates and the resultant values applied to probability tables, as described in Sokal et al., Biometry, W. H. Freeman and Co., San Francisco (1969), page 609. For an alpha level of p=0.05 and a 90% confidence of detecting a significant reduction in fertility rate when the control rate is at least 70% and the immunized is not greater than 10%, a group size of 15 animals per group was determined to be required and thus this was the group size used in the experiment.

Accordingly, 30 female baboons whose cycle length varied by no more than three days each side of its mean and who had exhibited progesterone levels of at least 3.0 ng./ml. for each of their last three menstrual cycles (thus indicating ovulation) were randomly assigned to each of two groups of 15 animals. Six male baboons, who had each proved their fertility by siring several offspring were selected for use in the experiments.

The control group of 15 baboons were immunized with pure tetanus toxoid while the other group received the aforementioned modified polypeptide conjugated with this toxoid. The antigens were dissolved in physiological saline, mixed with an equal volume of Complete Freund's Adjuvant (supplied by Difco Laboratories, Detroit, Mich.) and emulsified just prior to each immunization. The modified polypeptide/toxoid conjugate was dissolved at a concentration of 4.0 mg/ml and a dose of 2.0 mg given to each baboon in the second group, whereas the pure toxoid was dissolved in a concentration 2.0 mg/ml and a dose of 1.0 mg. given to each baboon in the control group; since the conjugate comprises approximately 50% of the toxoid by weight, the dose of toxoid administered to each animal was substantially the same. Each dose of the pure toxoid or of conjugate in the adjuvant, approximately 1.0 ml in volume, was injected intramuscularly into four separate sites in the animal, two in each thigh. The first (primary) immunization was given during the first five days of the menstrual cycle, with subsequent immunizations given at 28 day intervals thereafter or until a pregnancy was confirmed. Females that did not become pregnant received five or six immunizations during the course of the study depending upon the length of their individual menstrual cycles.

Blood samples were collected from the female baboons without anesthesia via the cubital vein, five to six ml. of blood being drawn at weekly intervals beginning at 21 days after the primary immunization, and also immediately before and after mating for antibody determinations. Blood samples for progesterone determinations were drawn five and seven days after sex skin deturgescence and, in cycles in which mating occurred, samples for pregnancy testing were drawn daily commencing 12 days after deturgescence and continuing until pregnancy was confirmed or menstruation began. After the blood samples were withdrawn, the serum was removed and samples not immediately tested were stored at −20° C.

The serum samples thus obtained were tested for the presence of antibodies to $^{125}$I-labelled HCG, Structure (XII), baboon chorionic gonadotropin (bCG) and tetanus toxoid by the methods described in Powell et al., Jr., Reprod. Immunol., 2, 1, (1980). As described in this Powell et al. paper, Structure (XII) can be labelled with $^{125}$I only after introduction of a tyrosine residue into the peptide. The HCG preparation, which was highly purified, had a biological potency of 10,800 IU/mg., while the bCG preparation, which was only partially purified, had a biological potency of 850 IU/mg. Concentrations of labelled antigen capable of saturation of antibody combining sites at equilibrium were reacted with dilutions of serum for five days at 4° C., followed by separation of the antigen-antibody complex from the unbound labeled antigen using the double-antibody method. With the exception of tetanus toxoid, the concentrations of labeled antigens were adjusted so that equimolar quantities were reacted with the serum. The molecular weight of bCG, which has not yet been established, was assumed to be the same as that of HCG, namely 38,000. The labeled antigen binding for HCG, bCG and Structure (XII) was expressed as moles/liter (M/L)×10$^{-10}$, whereas for tetanus toxoid, due to its molecular heterogeneity, binding was expressed as micrograms/ml.

All 30 female baboons were mated during the course of their third menstrual cycle following the primary immunization and for the next two consecutive cycles if they did not become pregnant. Based upon their previously established menstrual histories, each female baboon was transferred to a male's cage three days prior to expected ovulation. Cohabitation was continued until the day of sex skin deturgescence, 2–3 days after ovulation and the female was then transferred back to her individual cage. If the first mating did not make the female pregnant, subsequent matings were conducted with a different male baboon.

The serum levels of steroid hormones and bCG were determined by the radioimmunoassay methods described in Powell et al., *Clin. Chem.,* 19, 210, (1973) and Hodgen et al., *J. Clin. Endo. Metabol.,* 39, 457, (1974). The assay for bCG was conducted with an antiserum to Ovine-LH-beta supplied by Dr. Gary Hodgen, Bethesda, Md.; the supplier has previously shown, by means of unpublished data, that the binding of $^{125}$I-HCG to this antiserum can be displaced sensitively with bCG, but not with baboon LH. The sensitivity of this assay was 5 mIU of HCG/ml. Since antibodies produced in the female baboons immunized with the Structure (XII) conjugate were capable of binding the labeled HCG used in the HCG assay, this assay system could not be used to determine pregnancy in the baboons immunized with the conjugate. Accordingly, pregnancy testing of the conjugate-immunized baboons was performed by measuring estradiol and progesterone levels only. In the tetanus toxoid-immunized baboons, however, pregnancy was tested using the CG assay as well as the steroid assays.

Data obtained on antibody levels, cycle levels and progesterone concentrations were evaluated by various methods for randomized design experiments, as set out in Ostle, B., "Correlation Methods", in *Statistics in Research*, Ames I. A., Iowa State College Press (1954), page 174, while assessment of the mating data was accomplished by the chi-squared procedure set forth in Mantel, *Cancer Chemotherapy Reports,* 50, 163, (1966); this procedure compares the mating data in its entirety and not only in terms of individual matings.

RESULTS

The tetanus toxoid antibody level in both the baboons immunized with the pure tetanus toxoid and those immunized with the conjugate are shown in Table 4. High antibody levels against tetanus toxoid were produced in both groups of baboons 60 days after primary immunization, with peak levels being reached in 90–120 days. The differences between the tetanus toxoid antibody levels in the baboons immunized with the pure tetanus toxoid and with the conjugate were not significant at the p=0.05 confidence level. Thus, it will be seen that, in addition to the antifertility effects observed below, the instant conjugate conferred a significant degree of protection against tetanus. Accordingly, by careful choice of the hapten to which the polypeptide is conjugated in the instant modified polypeptide, the invention provides a method of protecting against a disease linked with the presence of the hapten as well as against pregnancy.

TABLE 4

Levels of antibody produced by female baboons against Tetanus Toxoid from immunization with Tetanus Toxoid or Tetanus Toxoid conjugated with Structure (XII) synthetic peptide during the first five months of immunization.

| Baboons Immunized With | | Tetanus Toxoid Antibody Titer (micrograms/ml) Days after Primary Immunization* | | | | |
|---|---|---|---|---|---|---|
| | | 30 | 60 | 90 | 120 | 150 |
| Tetanus Toxoid | $\bar{x}$ = | 20.6 | 515.7 | 662.9 | 667.2 | 821.6 |
| | se = | 7.3 | 37.8 | 46.5 | 73.3 | — |
| | n = | 15 | 15 | 15 | 5 | 1 |
| Conjugate | $\bar{x}$ = | 21.8 | 404.8 | 608.9 | 649.7 | 621.3 |
| | se = | 10.4 | 39.8 | 29.2 | 28.7 | 30.9 |
| | n = | 15 | 15 | 15 | 14 | 13 |

*Actual day may vary ±5 days

TABLE 5

Antibody levels produced by female baboons against Structure (XII), baboon chorionic gonadotropin and human chorionic gonadotropin from immunization with conjugate. Values were determined from serum collected during the early luteal phase of each menstrual cycle.

| Antibody Reactive To | | Antibody Level (M/L × 10$^{-10}$) Menstrual Cycle | | | | |
|---|---|---|---|---|---|---|
| | | 1 | 2 | 3 | 4 | 5 |
| Structure (XII) | $\bar{x}$ = | 62.8 | 246.3 | 195.1 | 184.8 | 204.5 |
| | 95% CI = | 28.2–97.6 | 29.9–462.3 | 82.0–308.2 | 57.1–312.6 | 37.3–371.7 |
| Baboon Chorionic Gonadotropin | $\bar{x}$ = | 2.6 | 7.3 | 10.4 | 10.0 | 9.9 |
| | 95% CI = | 1.1–4.0 | 3.1–11.5 | 3.1–17.8 | 1.8–16.7 | 0.02–19.5 |
| Human Chorionic Gonadotropin | $\bar{x}$ = | 43.8 | 185.7 | 145.8 | 125.1 | 135.5 |
| | 95% CI = | 20.9–66.6 | 27.2–344.1 | 48.7–243.1 | 25.3–224.9 | 15.2–255.7 |
| | n = | 15 | 15 | 15 | 14 | 13 |

The mean antibody levels produced to HCG, bCG and Structure (XII) in the group of baboons immunized with the conjugate are shown in Table 5. Antibody levels to Structure (XII) reached a maximum during the luteal phase of the second menstrual cycle, approximately 60 days after the primary immunizations, as did antibodies to HCG. While the mean antibody level to HCG and Structure (XII) were maintained by repeated booster immunizations, the responses of individual baboons varied considerably. There was a very close correlation between antibody levels to HCG and Structure (XII), r=0.97. The mean levels of antibodies which reacted with HCG were only 71% of those reacting with Structure (XII). However, because of variation in levels between the individual animals, this difference in levels is not significant at the p=0.05 level. Although the means levels of antibody reacting with bCG were only 4.5% of those reacting with Structure (XII) and 6.3% of those reacting with HCG, these bCG antibody levels reached maximum levels by the first mating cycle and remained close to that level during the next two cycles. There is a significant positive correlation (r=0.78) between the bCG antibody level and the Structure (XII) antibody level during these three cycles.

TABLE 6

Levels of antibody produced by female baboons against hCG and baboon CG from Immunization with conjugate. Levels determined from serum obtained during the luteal phase of three consecutive mating cycles.

Antibody Titer - M/L × $10^{-10}$

| Baboon | Mating Cycle 1 | | Mating Cycle 2 | | Mating Cycle 3 | |
|---|---|---|---|---|---|---|
| | hCG | bCG | hCG | bCG | hCG | bCG |
| 1 | 42.3 | 6.2 | 31.5 | 7.4 | 29.4 | 3.2 |
| 2 | 35.0 | 2.9 | 40.0 | 3.6 | 40.1 | 3.0 |
| 3 | 117.3 | 11.6 | 151.2 | 11.9 | 188.8 | 12.7 |
| 4 | 193.2 | 21.2 | 108.9 | 11.6 | 25.2 | 3.0 |
| 5 | 469.8 | 52.6 | 598.2 | 51.4 | 602.4 | 60.7 |
| 6 | 479.8* | 0.9* | | | | |
| 7 | 9.8 | 1.1 | 10.3 | 0.9 | 12.2 | 1.2 |
| 8 | 10.8 | 1.7 | 11.2 | 1.4 | 9.7 | 1.0 |
| 9 | 72.4 | 4.4 | 68.2* | 1.7* | | |
| 10 | 470.9 | 15.5 | 427.4 | 14.6 | 536.3 | 16.0 |
| 11 | 64.1 | 17.6 | 49.5 | 9.5 | 25.2 | 4.6 |
| 12 | 50.0 | 5.1 | 21.6 | 2.6 | 63.4* | 1.4* |

TABLE 6-continued

Levels of antibody produced by female baboons against hCG and baboon CG from Immunization with conjugate. Levels determined from serum obtained during the luteal phase of three consecutive mating cycles.

Antibody Titer - M/L × $10^{-10}$

| Baboon | Mating Cycle 1 | | Mating Cycle 2 | | Mating Cycle 3 | |
|---|---|---|---|---|---|---|
| | hCG | bCG | hCG | bCG | hCG | bCG |
| 13 | 46.6 | 4.3 | 57.6 | 6.3 | 59.2 | 6.4 |
| 14 | 41.0 | 2.7 | 127.6 | 13.2 | 110.2 | 12.0 |
| 15 | 85.2 | 8.4 | 48.5 | 4.1 | 60.3* | 1.6* |

*Pregnancy resulted from mating

Moreover, the antibody levels for HCG and bCG shown in Table 6 reveal significant correlation between these two antibody levels during the three mating cycles. The correlation coefficients (r) are 0.55, 0.89, and 0.85 for the first, second and third mating cycles respectively, the latter two correlation coefficients being significant at the 1% level.

Table 7 below compares the cycle lengths and progesterone levels in the luteal phase of the menstrual cycles before and after the immunizations of the two groups of baboons. The pre-immunization portion of this table shows that the two randomly assigned groups of baboons showed no significant differences at the p=0.05 level in the cycle length or progesterone levels for the three cycles immediately proceeding immunization. Even though both groups of baboons were immunized using Complete Freund's Adjuvant, no change significant at the p=0.05 level in the cycle lengths or progesterone levels was apparent when the three pre-immunization cycles were compared with the post-immunization cycles.

TABLE 7

Comparison of the length of menstrual cycles and luteal phase progesterone levels before and during the course of immunization of female baboons with Tetanus Toxoid or conjugate.

| Baboons Immunized With | | Menstrual Cycles | | | | | | | |
|---|---|---|---|---|---|---|---|---|---|
| | | Pre-Immunization | | | Post-Immunization | | | | |
| | | −3 | −2 | −1 | 1 | 2 | 3 | 4 | 5 |
| Tetanus Toxoid | | | | | | | | | |
| Cycle length | x̄ | 33.1 | 32.2 | 32.9 | 33.0 | 32.0 | 32.0 | 29.0 | — |
| | se | 0.8 | 0.8 | 0.8 | 1.5 | 1.0 | 1.1 | — | — |
| | n* | 15 | 15 | 15 | 15 | 15 | 5 | 1 | — |
| Progesterone | x̄** | 6.3 | 7.1 | 7.2 | 7.0 | 7.9 | 8.6 | 10.3 | 6.7 |
| | se | 0.6 | 0.6 | 0.6 | 0.9 | 1.0 | 0.6 | 0.8 | — |
| | n | 15 | 15 | 15 | 15 | 15 | 15 | 5 | 1 |
| Conjugate | | | | | | | | | |
| Cycle length | x̄ | 32.0 | 32.4 | 32.5 | 32.1 | 33.3 | 33.5 | 34.6 | 32.5 |
| | se | 0.6 | 0.7 | 0.7 | 0.9 | 1.1 | 1.1 | 1.3 | 0.6 |
| | n* | 15 | 15 | 15 | 15 | 15 | 14 | 13 | 11 |
| Progesterone | x̄** | 7.3 | 7.9 | 7.6 | 7.1 | 7.3 | 7.6 | 7.7 | 7.3 |
| | se | 0.7 | 0.7 | 0.6 | 1.0 | 0.9 | 0.8 | 0.6 | 0.3 |
| | n | 15 | 15 | 15 | 15 | 15 | 15 | 14 | 13 |

*decreases as a result of pregnancy
**includes values for cycle in which pregnancy occurred

TABLE 8

Comparison of fertility rates for female baboons immunized with Tetanus Toxoid to those immunized with conjugate. Matings commenced during the course of the third menstrual cycle following primary immunization.

| Baboons Immunized With | Mating Cycle 1 | 2 | 3 | Total Number Pregnant | Total Number Mated | Overall Fertility Rate (%) |
|---|---|---|---|---|---|---|
| Tetanus Toxoid | | | | | | |
| Number Mated | 15* | 5 | 1 | | 21 | |
| Number Pregnant | 10 | 4 | 1 | 15 | | |
| Fertility Rate (%) | 66.7 | 80.0 | 100.0 | | | 71.4 |
| Conjugate | | | | | | |
| Number Mated | 15* | 14 | 13 | | 42 | |
| Number Pregnant | 1 | 1 | 2 | 4 | | |
| Fertility Rate (%) | 6.7 | 7.1 | 15.4 | | | 9.5 |

*Includes 1 anovulatory menstrual cycle

Table 8 shows the highly significant difference in the fertility rate between the two groups of baboons. On the first mating, 10 out of 15 of the tetanus toxoid-immunized baboons became pregnant, 4 of the 5 remaining baboons became pregnant after the second mating and the single remaining baboon became pregnant after the third mating. Thus, of 21 matings, 15 resulted in pregnancy, giving a fertility rate of 71.4%.

Of the 15 baboons immunized with the conjugate, one became pregnant after the first mating, one of the remaining 14 became pregnant after the second mating and 2 of the remaining 13 baboons became pregnant after the third mating. Thus, 42 matings resulted in four pregnancies for a fertility rate of 9.5%.

Chi-squared analysis of this data shows that this difference in fertility rate is highly significant (p less than 0.005) even after adjustment for the small sample size.

The antibody levels to tetanus toxoid from sera obtained during the three mating cycles were assessed for correlation to the outcome of mating for all animals. No correlation significant at the p=0.05 level was found for either group of baboons. Similarly, although the post-mating antibody levels for menstrual cycles 3, 4, and 5 were quite variable, as shown by the rather large 95% confidence interval, no correlation significant at the p=0.05 level was found between the antibody levels to Structure (XII), HCG or bCG and the fertility of the conjugate-immunized group. However, there was a significant difference (p less than 0.025) between the mean bCG antibody level in the four pregnant conjugate immunized baboons ($1.4 \times 10^{-10}$ M/L) and the mean (9.8) and the 95% confidence interval (5.5–14.1) levels of the same antibodies for all matings, thus suggesting that these four baboons became pregnant because their bCG antibody levels were insufficiently raised.

I have shown in the following published papers: Excerpta Medica International Congress Series No. 402, pp. 1379 (1976); and "Physiological Effects of Immunity Against Reproductive Hormones", R. G. Edwards and M. H. Johnson (ed.), Cambridge University Press, p. 249 (1975); that immunizations with synthetic peptides containing a C-terminal portion of beta-HCG result in the production of antibodies capable of binding and neutralizing the biological activity of intact HCG and that these antibodies exhibit a low degree of reactivity with baboon CG. This is in accord with the results of this Example, in which the conjugate based on Structure (XII), the 109–145 sequence of beta-HCG, produced high levels of antibody to HCG but relatively low levels of antibody to bCG. Nevertheless, despite the low levels of bCG antibody, the conjugate was highly effective in preventing pregnancy. The pregnancy-preventing action of the conjugate demonstrated in this Example provides the statistically valid proof of the feasibility of this approach to fertility regulation in humans. It may reasonably be anticipated that the antifertility effects which the conjugate would produce in humans would be considerably greater than that in baboons, given the much higher level of antibodies to HCG produced in the baboons, as compared to levels of antibody to bCG.

The exact mechanism of action of the conjugate is not known, although presumably antibody neutralization of CG occurs in the peripheral blood soon after implantation and disrupts trophic hormone support to the corpus luteum of pregnancy and causes early abortion. However, since the duration of the menstrual cycle is not significantly effected, it appears that pregnancy must be disrupted almost immediately after implantation.

EXAMPLE XXXII

The following experiments were conducted to determine the most appropriate peptide and carrier for use in a modified polypeptide of the invention intended for provoking antibodies to HCG.

The following peptides, each having a sequence derived at least in part from that of β-HCG were prepared by the same method as in Example XXXI (the numbers given refer to the sequence of bases in the full β-subunit of HCG, Structure (I) above:

a. 138–145, hereinafter referred to as Structure (XVI) Ser-Asp-Thr-Pro-Ile-Leu-Pro-Gln;

b. 126–145, hereinafter referred to as Structure (XVII) Pro-Ser-Leu-Pro-Ser-Pro-Ser-Arg-Leu-Pro-Gly-Pro-Ser-Asp-Thr-Pro-Ile-Leu-Pro-Gln;

c. 115–145, Structure (VI) above;

d. 111–145, Structure (II) above;

e. 109–145, Structure (XII) above;

f. 106–145, hereinafter Structure (XVIII) His-Pro-Leu-Thr-Cys-Asp-Asp-Pro-Arg-Phe-Gln-Asp-Ser-Ser-Ser-Ser-Lys-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln;

g. 105–145, hereinafter Structure (XIX) Asp-His-Pro-Leu-Thr-Cys-Asp-Asp-Pro-Arg-Phe-Gln-Asp-Ser-Ser-Ser-Ser-Lys-Ala-Pro-Pro-Pro-Ser-Leu-Pro-Ser-Pro-Ser-Arg-Leu-Pro-Ser-Asp-Thr-Pro-Ile-Leu-Pro-Gln;

h. Cys-(Pro)$_6$-(111–145), Structure (XIV) above;

i. (111–145)-(Pro)$_6$-Cys, Structure (X) above; and j. Cys- (105–145), with the SH group of the Cys residue at position 110 blocked with an acetamidomethyl (ACM) group, hereinafter referred to as Structure (XX).

The peptides of Structures (XVIII), (XIX) and (XX) contained a protected sulfhydryl group at the 110 cysteine position. The purity of all the peptides was demonstrated using high-voltage electrophoresis, thin-layer chromatography and amino acid analysis.

The following carriers were used in the experiments: tetanus toxoid, polymerized flagellin, poly-DL-alanine/lysine (polyalanine), (poly DAL) poly(tyrosine, glutamic acid)/poly(alanine, lysine) (TGAL) and polymerized sucrose (Ficoll), described above. The carriers used were diphtheria toxoid obtained from Connaught Laboratories, Swiftwater, Pa.) bovine gamma globulin (obtained from Swartz-Mann Laboratories, Orangeburg, N.Y.), *Corynebacterium parvum* (obtained from Burroughs-Wellcome, London, England), uncapsulated meningococcal protein and pneumococcus polysaccharide.

A thiol group on each peptide was coupled to an amino group on the carrier by the same method as in Example XXXI. The site at which the peptide was coupled to the carrier depended upon the point at which a thiol group existed or could be created on the peptide. Structure (XII) contains a cysteine at position 110 and accordingly, this peptide was conjugated by means of the thiol group produced at this position after cleavage of the synthetically produced disulfide dimer of the peptide. Structures (XVI), (XVII), (XVIII) and (XIX) had a thiol group introduced at the amino terminal group and were coupled to the carrier via this introduced thiol group. Structures (II) and (VI) had thiol groups at the terminal amino group and also at the amino group at the lysine residue at position 122; under the conditions used, approximately equal numbers of peptides were attached to the carrier at each of the two attachment sites. Structures (X) and (XIV) were coupled to carriers using the thiol group on the terminal cysteine residue.

After the coupling of the peptide to the carrier, the resulting conjugates were all purified by gel filtration or ultrafiltration and the ratio of the peptide to carrier was determined.

The animals used in these experiments were genetically heterogenous rabbits of the New Zealand White variety, weighing 2–4 kg. and inbred female mice of the C3H/He strain, 8–10 weeks old or retired breeders, weighing 20–30 gm. each and obtained from Jackson Laboratories, Bar Harbor, Me. For use in the rabbits, the conjugates were dissolved in saline and emulsified with an equal volume of Complete Freunds' adjuvant, exactly as in Example XXXI. However, for immunization into mice, an adjuvant was prepared by mixing 1.5 parts by volume of Arlacel A (obtained from Hilltop Research, Miamiville, Ohio) with 8.5 parts by volume of Klearol (Bate Chemical, Don Mills, Ontario, Canada) and autoclaving for 20 minutes at 15 lb. pressure. Thereafter, heat-killed desiccated acetone-washed BCG bacteria (obtained from Connaught Laboratories, Willowdale, Ontario, Canada) were added at the rate of 5 mg. per 10 ml. of adjuvant. Apart from the change of adjuvant, the solution used to immunize the mice was prepared in the same way as that used to immunize the rabbits.

The mice were immunized three times, the primary immunization being given at day 0 with booster immunizations given at 21 and 38 days; the dose of conjugate injected on each occasion into mice was usually 100 $\mu$g, though multiples of this dose were given where stated. Blood samples were collected from the mice at weekly intervals starting at day 14.

The rabbits were immunized three times at 21 day intervals (the primary immunization at day 0 and booster immunizations at 21 and 42 days), 1 mg. of the conjugate being given at each immunization. Blood samples were collected from the rabbits weekly beginning at day 21. The sera of the blood samples drawn from both the mice and the rabbits were separated from the cells and stored at −20° C. prior to analysis.

The levels of antibody to both the peptide used and HCG were measured by isotopically labeling the antigen with $^{125}$I and reacting it with various dilutions of the antisera. In most cases, 250 pg. of labeled antigen was incubated with 200 $\mu$l of diluted serum for 120 hours at 4° C. Antigen binding was determined at three or more serum dilutions using a double antibody technique, the results being expressed as nanograms (ng) of antigen bound per milliliter of undiluted serum. The minimum sensitivity was 1 ng/ml. In some experiments, the level of antigen binding was tested using two concentrations of antigen with two dilutions of serum and expressing the results as $M/L \times 10^{-10}$ by the same methods as in Example XXXI.

The antigen binding levels found in the various groups of rabbits and mice were compared using the two-tailed Mann-Whitney U-test described by S. Siegel, "The Case of Two Independent Variables", in *Nonparametric Statistics*, McGraw-Hill Book Company, New York (1956), p. 116. Results where $p<0.05$ were considered significant. In mice, in a few cases where the level of antigen binding was too low to be detected by the methods used, an arbitrary value of 0.1 ng/ml was assigned for statistical comparisons of values that were undetectable.

RESULTS

Mice were injected by the procedures set out above with doses of 100, 40, 8 and 1.6 $\mu$g. of conjugates of Structure (II) and (XII) with tetanus toxoid. Table 9 below shows the levels of antibodies to both the peptide used and HCG at 21 and 35 days after the primary immunization. Analysis of these results shows that the differences between peptide binding in the sera between the mice injected with the two conjugates were significant at 21 days but not at 35 days. An increase in antibody levels to peptides was observed at 35 days with increasing doses of antigen injected, but again there was no significant difference between the antibody levels of the mice injected with the two conjugates at the same dosage levels.

TABLE 9

| Tetanus Toxoid Coupled To Peptide of Structure | Sera 21 days after Primary Immunization Immunization Dose (mg) | | | | Sera 35 days after Primary Immunization Immunization Dose (mg) | | | |
|---|---|---|---|---|---|---|---|---|
| | 100 | 40 | 8 | 1.6 | 100 | 40 | 8 | 1.6 |
| | Antibody Level - Peptide ng/ml (sd) | | | | | | | |
| II | 10.4 | 12.6 | 8.6 | 4.2 | 38.0 | 27.4 | 16.4 | 5.8 |
| | (3.4) | (8.1) | (3.0) | (2.6) | (60.7) | (15.2) | (21.2) | (4.1) |
| XII | 0.1 | 0.9 | 1.1 | 0.1 | 207.8 | 80.3 | 85.0 | 9.0 |
| | (0) | (1.7) | (2.2) | (0) | (210.8) | (56.3) | (99.2) | (11.5) |
| p, U-test | 0.008 | <0.016 | 0.008 | 0.008 | 0.112 | 0.190 | 0.548 | 0.392 |

TABLE 9-continued

| Tetanus Toxoid Coupled To Peptide of Structure | Sera 21 days after Primary Immunization Immunization Dose (mg) | | | | Sera 35 days after Primary Immunization Immunization Dose (mg) | | | |
|---|---|---|---|---|---|---|---|---|
| | 100 | 40 | 8 | 1.6 | 100 | 40 | 8 | 1.6 |
| | Antibody Level - HCG ng/ml (sd) | | | | | | | |
| II | 0.1 | 0.1 | 0.1 | 0.1 | 0.8 | 3.8 | 0.1 | 0.1 |
| | (0) | (0) | (0) | (0) | (1.4) | (3.8) | (0) | (0) |
| XII | 0.1 | 0.1 | 0.1 | 0.1 | 51.4 | 2.3 | 9.6 | 1.1 |
| | (0) | (0) | (0) | (0) | (88.6) | (2.0) | (14.4) | (2.2) |
| p, U-test | >1 | >1 | >1 | >1 | 0.286 | 0.730 | <0.056 | 0.690 |

Figure 4:
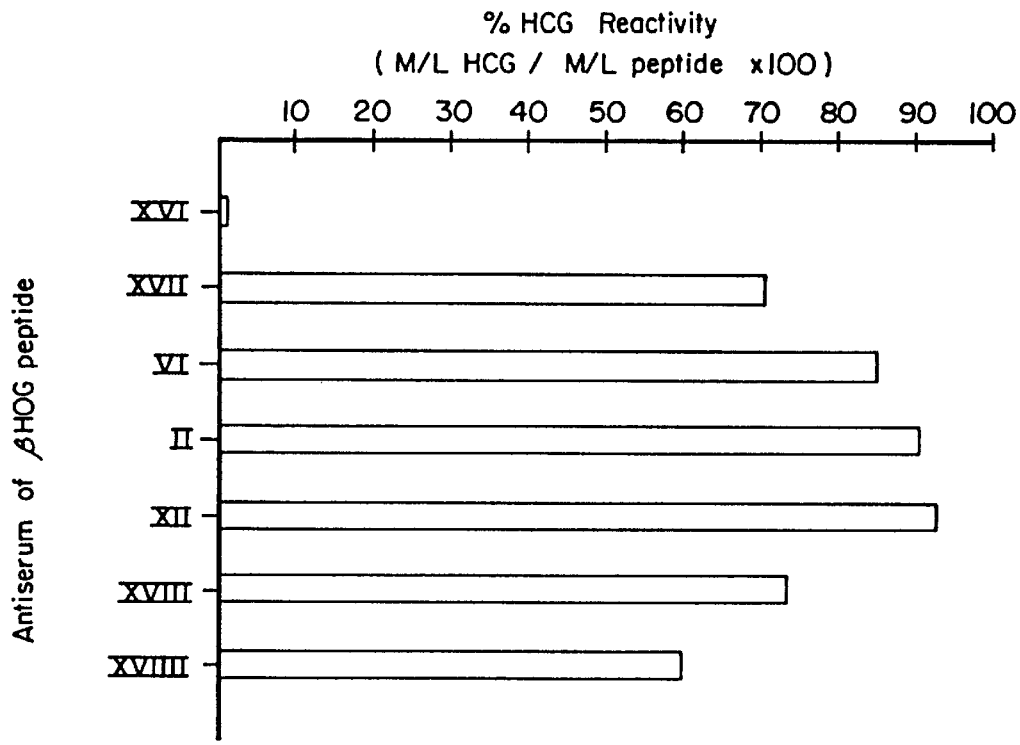
FIG. 4 shows the levels of antibody to beta-HCG produced in rabbits by various modified peptides in Example XXXII below.

To determine the effect of chain-length of the peptide on antibody response, groups of four rabbits were injected with conjugates of tetanus toxoid with the peptides of Structures (XVI), (XVII), (VI), (II), (XII), (XVIII), and (XIX). Sera from animals immunized with these conjugates were reacted separately with equimolar quantities of labeled peptide and labeled HCG, and the proportion of antibodies reactive to peptides which were also reactive to HCG determined. The results are shown in FIG. 4.

Contrary to what might be expected, the maximum reactivity to HCG is not a simple function of the chain-length of the peptide. Maximum reactivity to peptide and HCG was obtained by rabbits receiving the conjugate of the peptide of Structure (XII), representing residues 109–145 of β-HCG. The peptide of Structure (II), representing residues 111–145 of β-HCG, produced antibodies nearly as reactive as the peptide of Structure (XII), but the antibody levels produced by the longer peptides of Structures (XVIII) and (XIX), representing respectively residues 106–145 and 105–145 of β-HCG, were lower than those produced by the peptides of Structures (XII) and (II). Not surprisingly, the shorter peptides also resulted in a lower proportion of antibody reacting to HCG.

A further series of tests were effected to determine the effect of the hexaproline cystine spacer sequences in the peptides of Structures (XIV) and (X) on antibody production. Conjugates of tetanus toxoid were prepared coupled to the peptides of Structures (II) (the 111–145 sequence without any spacer), (XIV) (the 111–145 sequence with a N-terminal spacer) and (X) (the 111–145 sequence with a C-terminal spacer), all conjugates containing a peptide:carrier ratio of approximately 20–22 peptides/$10^5$ daltons of toxoid.

Table 10 below shows the antibody levels to HCG and peptides obtained in mice. Twenty-one days after primary immunization, the HCG antibodies were significantly higher in the mice immunized with the conjugates containing either of the spacer peptides than with the non-spacer peptide, Structure (II). Thirty-five days after primary immunization, the HCG antibody levels in mice immunized with the conjugate containing the C-terminal spacer peptide of Structure (X) were significantly greater than those of mice immunized with the non-spacer peptide, but the difference in antibody levels between the latter and the mice receiving the conjugate of the N-terminal spacer peptide of Structure (XIV) was not significant.

TABLE 10

| Tetanus Toxoid Coupled to Peptide of Structure | Sera 21 days after Primary Immunization | | | | Sera 35 days after Primary Immunization | | | |
|---|---|---|---|---|---|---|---|---|
| | Antibody Level to Peptide* | U-test p | Antibody Level to HCG* | U-test p | Antibody Level to Peptide* | U-test P | Antibody Level to HCG* | U-test p |
| (a) II | 10.4 | | 0.1 | | 38.0 | | 0.8 | |
| | (3.4) | | (0) | | (60.7) | | (1.4) | |
| U-test (a):(c) | | 0.31–0.42 | | 0.008 | | 0.73–0.90 | | 0.032 |
| (b) XIV | 0.1 | | 4.5 | | 1.7 | | 33.2 | |
| | (0) | | (5.2) | | (1.8) | | (48.0) | |
| U-test (b):(a) | | 0.170 | | 0.008 | | 0.032 | | 0.286 |
| (c) X | 1.2 | | 3.7 | | 0.4 | | 1.2 | |
| | (1.6) | | (5.0) | | (0.8) | | (1.6) | |
| U-test (c):(b) | | 0.69–0.84 | | 0.31–0.42 | | 0.056 | | 0.310 |

*nanograms/ml (sd)

However, very different results were obtained when the serum antibodies were evaluated in terms of their ability to bind peptides. More of the labelled peptide was bound by the antibodies produced by the conjugate of the non-spacer peptide of Structure (II) 35 days after the primary immunization than by the antibodies produced by mice immunized with the conjugate of the N-terminal spacer peptide of Structure (XIV). There was no significant difference between the peptide binding abilities of the sera from mice immunized with the conjugates of the N-terminal and C-terminal peptides of Structures (XIV) and (X) respectively at this time.

Figure 5:
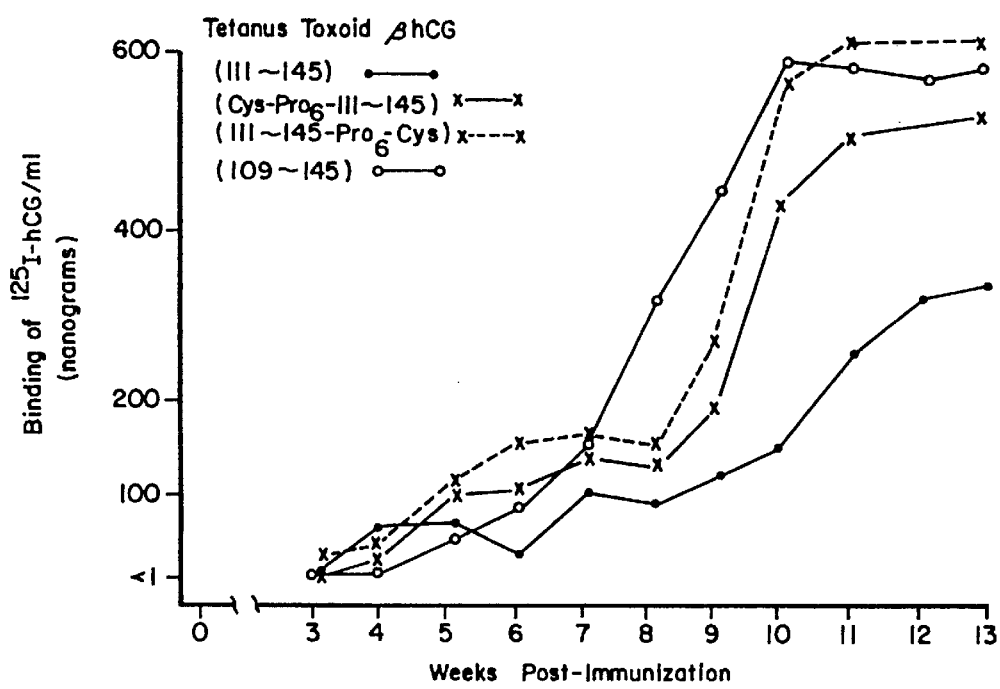
FIG. 5 shows the levels of antibody to HCG produced in rabbits by various tetanus-toxoid-coupled modified peptides in Example XXXII below.

The tests in rabbits were carried out with the same three conjugates as in mice, and also with the conjugate of tetanus toxoid and the peptide of Structure (XII) (the 109–145 sequence of β-HCG) used in the preceding series of tests. The antibody levels 10–13 weeks after the primary immunization are shown in FIG. 5. These results show that the mean antibody levels in rabbits immunized with the conjugate non-spacer peptide of Structure (II) were lower than those of rabbits immunized with the spacer peptides of Structures (XIV) and (X), but the rabbits injected with the conjugate of the peptide of Structure (XII) had mean antibody levels to HCG comparable to the rabbits immunized with the conjugates of the spacer peptides of Structures (XIV) and (X).

A further series of tests was carried out to determine the effects of different carriers on antibody production. The peptide of Structure (XII), representing the 109–145 sequence of β-HCG, was coupled to various carriers in a ratio of 15–28 peptides per $10^5$ daltons of carrier and mice and rabbits were immunized with these conjugates. The antibody levels to the peptide and to HCG were tested in the sera 21 and 35 days after the primary immunization. The results obtained in mice are shown in Table 11 below. Although the large standard deviations makes the detection of significant differences difficult, the results do show that the tetanus toxoid conjugate elicited antibody levels to both the peptides and HCG which were significantly higher than those produced by the conjugates of all the other carriers. Mean antibody levels in the groups injected with the peptide conjugated with flagellin and bovine gamma globulin were higher than those in which the peptide was linked to synthetic sugar (Ficoll) or polypeptide carriers. Table 12 shows the U-test analysis of the data presented in Table 11.

TABLE 11

| Carrier Used | Sera 21 days after Primary Immunization Antibody Level to | | | | Sera 35 days after Primary Immunization Antibody Level to | | | |
|---|---|---|---|---|---|---|---|---|
| | Peptide | | HCG | | Peptide | | HCG | |
| | ng/ml | (sd) | ng/ml | (sd) | ng/ml | (sd) | ng/ml | (sd) |
| Tetanus Toxoid | 11.3 | (5.1) | 1.9 | (2.1) | 224.1 | (139.0) | 89.2 | (128.2) |
| Flagellin | 5.5 | (4.3) | 0.7 | (1.4) | 39.8 | (19.9) | 24.7 | (11.8) |
| TGAL | 2.9 | (6.2) | 2.7 | (1.4) | 15.0 | (10.0) | 10.9 | (6.5) |
| bov GG | 3.5 | (3.2) | 0.1 | (0) | 43.3 | (22.1) | 26.7 | (52.1) |
| Polyalanine | 0.5 | (1.0) | 0.1 | (0) | 3.1 | (6.2) | 0.5 | (0.9) |
| Ficoll | 0.1 | (0) | 0.8 | (1.6) | 9.2 | (5.7) | 23.6 | (43.3) |
| None | 1.3 | (1.2) | 0.1 | (0) | 0.8 | (0.7) | 0.1 | (0) |

TABLE 12

| Carrier | Sera 21 days after Primary Immunization | | | | Sera 35 days after Primary Immunization | | | |
|---|---|---|---|---|---|---|---|---|
| | TT | Flagellin | TGAL | bovGG | TT | Flagellin | TGAL | bovGG |
| Antibody Level-Peptide | | | | | | | | |
| Tetanus Toxoid | — | 0.096 | 0.056 | 0.032 | — | 0..036 | 0.036 | 0.036 |
| Flagellin | 0.096 | — | 0.310 | 0.42–0.55 | 0.036 | — | 0.016 | 1.000 |
| TGAL | 0.056 | 0.310 | — | 0.310 | 0.036 | 0.016 | — | 0.056 |
| bov GG | 0.032 | 0.42–0.55 | 0.310 | — | 0.036 | 1.000 | 0.056 | — |
| Antibody Level-HCG | | | | | | | | |
| Tetanus Toxoid | — | 0.310 | 0.31–0.42 | 0.150 | — | 1.000 | 0.250 | 0.250 |
| Flagellin | 0.310 | — | 0.056 | 0.690 | 1.000 | — | 0.056 | 0.222 |
| TGAL | 0.31–0.42 | 0.056 | — | 0.008 | 0.250 | 0.056 | — | 0.548 |
| bov GG | 0.150 | 0.690 | 0.008 | — | 0.250 | 0.222 | 0.548 | — |

The results obtained in rabbits are shown in Table 13 below. The highest antibody levels were obtained in the rabbits immunized with conjugates of bovine gamma globulin, tetanus toxoid and diphtheria toxoid, there being no significant difference between the peak antigen titers of these three carriers. Significantly lower antibody levels were found in rabbits immunized with bacterial carriers, while synthetic polypeptide and sugar carriers produced antibody levels which were significantly lower than those of bacterial carriers.

TABLE 13

| | Maximum Antigen Binding Levels* | | | |
|---|---|---|---|---|
| Carrier | HCG | | Peptide | |
| Used | M/L × $10^{-10}$ | sd | M/L × $10^{-10}$ | sd |
| bov GG | 479.2[a] | 402.5 | 552.3[a] | 410.8 |
| Diphtheria Toxoid | 365.3[a] | 176.8 | 423.3[a] | 189.3 |
| Tetanus Toxoid | 339.3[a] | 95.5 | 417.6[a] | 106.2 |
| C-parvum | 215.9 | 121.5 | 255.4 | 131.6 |
| Flagellin | 210.4 | 157.5 | 244.6 | 198.1 |
| Pneumococcus Polysaccharide | 135.7 | 102.8 | 153.7 | 113.0 |
| Meningococcal Protein | 97.9 | 107.6 | 118.4 | 122.6 |
| TGAL | 29.9 | 22.6 | 37.3 | 35.5 |
| Ficoll | 10.6 | 8.3 | 13.0 | 9.0 |
| Polyalanine | 8.6 | 4.7 | 12.2 | 7.5 |

*4 rabbits/groups
[a]not significantly different (p > 0.05)

Figure 6:
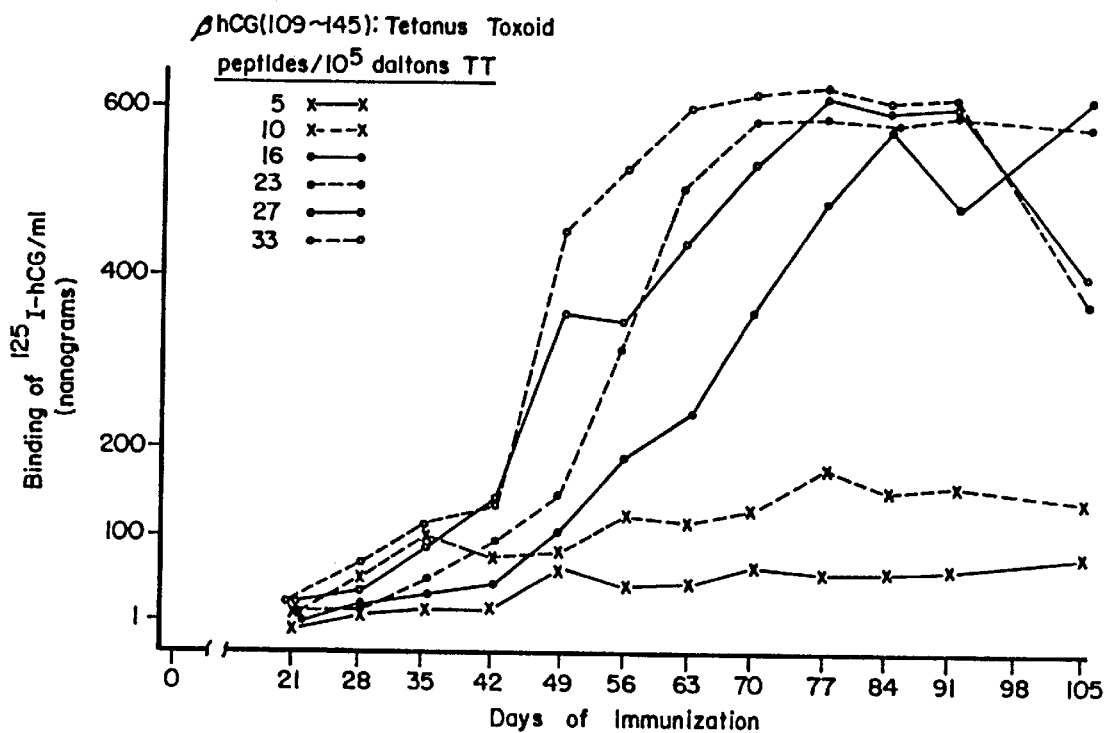
FIG. 6 shows the levels of antibody to HCG produced in rabbits by various tetanus-toxoid-coupled modified peptides having differing peptide carrier ratios in Example XXXII below.

A final series of experiments were performed to determine the effect of the peptide:carrier ratio on antibody production. Conjugates of tetanus toxoid and the peptide of Structure (XII) with peptide:carrier ratios of from 5–33 peptides per $10^5$ daltons of carrier were prepared and groups of four rabbits were immunized with these conjugates. The mean antibody levels to HCG produced 42, 63, and 84 days after primary immunization are shown in FIG. 6. Statistical analysis of the data in FIG. 6 shows no significant difference with peptide:carrier ratio 42 days after primary immunization, but 63 days after primary immunization the antibody responses to conjugates containing 23 or more peptides per $10^5$ daltons of toxoid are significantly greater than those of conjugates with lower peptide:carrier ratios. A similar comparison 84 days after primary immunization shows that the antibody levels produced by conjugates containing 16 or more peptides per $10^5$ daltons of carrier are significantly greater than those of conjugates with a lower peptide:carrier ratio. Accordingly, it is believed that it is advantageous to use a conjugate containing between 20 and 30 peptides per $10^5$ daltons of carrier.

When mice were immunized with the same conjugates, the responses were more variable and no linear dose-antibody response was observable, but the highest antibody levels were obtained in mice receiving conjugates containing 28–23 peptides per $10^5$ daltons of carrier.

The above results show that antibodies formed to peptides with 30 or more amino acids bind HCG better than those to peptides with fewer residues. However, since the 40 and 41 residue peptides (Structures (XVIII) and (XIX) above) were not as reactive to HCG as the 35 or 37 residue peptides of Structures (II) and (XII) above, it appears that no immunological determinant of HCG is present in the 105–109 region of the beta subunit thereof. Based upon the foregoing results, the preferred peptides for use in forming conjugates to produce antibodies to HCG are the peptides of Structures (XII) (the 109–145 sequence without spacers), (XIV) and (X) (the 111–145 sequence with N-terminus and C-terminus spacers respectively). The addition of the seven-residue spacer sequence to either the N-terminus or the C-terminus of the 111–145 peptide of Structure (II) produced higher antibody levels than the same peptide without spacer. It appears likely that a similar advantage can be produced by attaching similar spacer sequences to the 109–145 peptide of Structure (XII) since this peptide without spacers elicited responses similar to the 111–145 peptide with spacer (cf. results for Structures (XIV) and (XII)). On the other hand, it appears disadvantageous to attach peptides to the carrier at both position 122 and the N-terminus (see results from peptides of Structures (II) and (VI) above) since peptides attached to the carrier at both positions did not elicit levels equivalent to those attached at either terminus alone. Probably coupling of the peptide at both its midpoint and its N-terminus affects its conformation and creates an immunological determinant dissimilar to that found on intact HCG.

Moreover the results presented above strongly suggest that the best carriers for use in humans or other primates are tetanus toxoid and diphtheria toxoid. While the antibody levels in rabbits for bovine gamma globulin, tetanus toxoid and diphtheria toxoid are not significantly different, the antibody levels produces in mice with conjugates of the bovine gamma globulin are not as high as those produced by conjugates of the two toxoids. Immunization of humans or other primates with tetanus and diphtheria toxoids is acceptable and even advantageous (since a single vaccination can then provide protection against tetanus or diphtheria as well as an isoimmunogenic action), whereas injections of non-primate gamma globulins may not prove safe. Conjugates of either tetanus toxoid or diphtheria toxoid with a peptide-:carrier ratio of 20–30 peptides per $10^5$ daltons of carrier evoked large titers of antibody reactive to HCG and would therefore appear to be suitable for an anti-HCG vaccine.

EXAMPLE XXXIII

This example illustrates the variations in antibody levels produced by changes in the adjuvant and vehicle used in conjunction with a modified polypeptide of the invention.

Based upon the results in Example XXXII above, the conjugates of tetanus toxoid with the peptides of Structures (XIV) and (XII) were selected as most efficacious in generating antibodies to HCG and were thus used in these experiments to select the optimum adjuvant and vehicle. The tetanus toxoid/peptide conjugates were prepared in exactly the same manner as in Example XXXII and purified by gel filtration and lyophilization. The conjugate of the peptide of Structure (XII) contained 21–25 peptides per $10^5$ daltons of carrier, while the conjugate of the peptide of Structure (XIV) contained 20–27 peptides per $10^5$ daltons of carrier. A further conjugate was prepared by conjugating the same tetanus toxoid to both the peptide of Structure (XIV) and the synthetic muramyl dipeptide CGP 11637 (manufactured by Ciba-Geigy Limited Basle, Switzerland, -Formula (a) below). Using carbodiimide, the carboxyl group of the dipeptide was coupled to the amino groups of the tetanus toxoid, whereafter the peptide of Structure (XIV) was coupled to the tetanus toxoid via the remaining amino groups using the same procedure as in Example XXXII. The resultant conjugate contained five muramyl dipeptides and 31 peptides of Structure (XIV) per $10^5$ daltons of carrier respectively.

A total of eight different adjuvants were tested. The first five of these adjuvants were synthetic muramyl dipeptide hydrophilic analogues obtained from Ciba-Geigy Ltd., these five dipeptides being:

(a) CGP 11637, of the formula NAc-nor Mur-L. Ala-D. iso Gin;

(b) CGP 14767, of formula NAc-nor-Mur-L-Abu-D.isoGln;

(c) CGP 18177 of formula NAc-Mur (6-0-stearoyl)-L.Ala-D.isoGln;

(d) CGP 18741 of formula NAc-nor-Mur (6-0-stearoyl)-L.Ala-D.isoGln;

(e) CGP 19835 of formula NAc-Mur-L.Ala-D.isoGln-L.Ala-Cephalin.

The sixth adjuvant was another muramyl dipeptide obtained from Syntex Corporation, Palo Alto, Calif. being:

(f) DT-1, of formula NGlycol-Mur-L. a -Abu-D.isoGln.

The last two adjuvants were lipophilic adjuvants manufactured by Ciba-Geigy Ltd., as follows:

(g) CGP 16940, of formula N-Palmitoyl-S-[2(R,S)-3-dipalmitoyloxy-propyl] L-Cys-L-Ser-L-Ser-L-Asn-L-Ala-L-Glu; and (h) CGP 12908, a highly purified lipoprotein from the cell membranes of *E. Coli* B.

The vehicles used in these experiments were:

(a) an aqueous solution of 0.1M sodium phosphate and 0.14M sodium chloride, of pH 7.0, hereinafter designated BPS;

(b) Incomplete Freunds' adjuvant comprising 1.5 parts by volume of Arlacel A (mannide monooleate) and 8.5 parts by volume of Klearol, both reagents being obtained from the same sources as in Example XXXII, the adjuvant being referred to hereinafter as IFA;

(c) Squalene-Arlacel A, comprising four parts by volume Squalene (obtained from Sigma Chemicals, St. Louis, Mo. and one part by volume Arlacel A;

(d) Squalane-Arlacel A, comprising four parts by volume Squalane (obtained from Eastman Kodak, Rochester, N.Y. and one part by volume Arlacel A;

(e) Peanut oil adjuvant, comprising 10 parts by volume peanut oil (obtained from Merck, Munich, West Germany) and one part by volume egg lecithin;

(f) Liposomes adjuvant, comprising 12 parts by weight egg lecithin and 1.6 parts by weight cholesterol; and (g) Alum adjuvant, comprising 10 percent by weight potassium alum precipitated with 1N sodium hydroxide, as described in M. W. Chase and C. A. Williams (eds.), "Methods in Immunology and Immunochemistry", Vol. I, *Preparation of Antigens and Antibodies*, Academic Press, New York (1967), pp. 201–202.

The experimental animals used in these studies were the four inbred strains of mice C3H/He, C57BL/6, DBA/1 and SJL, obtained from the same source as in Example XXXII. The mice were retired breeders of more than 32 weeks of age and weighed 25–30 grams. Also used were genetically heterogenous New Zealand White rabbits weighing 2–4 kg. obtained from the same source. The mice were immunized subcutaneously with a primary immunization at day 0 and boosters at 21 and 38 days and, in some experiments, at day 55. Unless otherwise stated, each injection comprised 200 m g. of conjugate and 100 m g. of adjuvant. Blood samples were collected from the mice 28, 35, 45, 52, 62, and 69 days after the primary immunization.

The rabbits were immunized intramuscularly three times at 21 day intervals, each injection comprising 500 m g. of conjugate and 500 μg. of adjuvant unless otherwise stated. Blood samples from the rabbits were collected weekly on the 21st day after the first immunization. In the case of the blood samples from both the mice and the rabbits, the serum was separated from the remaining components of the blood and stored at −20° C. prior to analysis. Complete Freund's adjuvant purchased or prepared as in Example XXXII above was used as a reference adjuvant. The levels of antibody in the blood sera reacting to the peptide in the conjugate or HCG were measured using the same double-antibody technique as in Example XXXII and the test results were evaluated using the same Mann-Whitney U-test as in that Example. In experiments in which antigen binding levels were pooled within each experimental group, Chi-squared analysis was used to determine significant differences.

RESULTS

In a first series of tests, various adjuvants were evaluated using IFA as the vehicle. The Structure (XII)/tetanus toxoid conjugate was combined separately with the adjuvants CGP 11637, CGP 14767, CGP 12908 and CGP 16940. The resultant conjugate/adjuvant mixtures were incorporated into IFA emulsions and a parallel series of emulsions were prepared using the conjugate (without any adjuvant) in Complete Freunds' Adjuvant (CFA). Each separate emulsions was administered to four groups each comprising five mice from one of the four inbred strains. Antibody levels to Structure (XII) and HCG were determined 52 days after the primary immunization and the results are shown in Table 14 below.

the C57BL/6 group on the other are significant at the p=0.05 level. Moreover, the differences between the HCG antibody levels of the SJL group on the one hand and the DBA/1 and the C57BL/6 group on the other are also significant at the p=0.05 level.

Table 15 below presents statistical comparisons of antibody levels produced in mice receiving each of the four adjuvants in comparison with the antibody levels in mice receiving the CFA.

TABLE 15

| | | Adjuvant (Compared with CFA) | | | |
|---|---|---|---|---|---|
| Antigen | Mouse Strain p* | CGP 11637 p* | CGP 14767 p* | CGP 12908 p* | CGP 16940 |
| Structure (XII) | C57BL/6 | 0.22–0.31 | 0.096 | 0.420 | 1.0–1.158 |
| | DBA/1 | 0.008 | 0.008 | 0.556 | 0.016 |
| | C3H/He | 0.016 | 0.134 | 0.400 | 0.028 |
| | SJL | 0.032 | 0.072 | 0.904 | 1.000 |
| HCG | C57BL/6 | 1.000 | 1.000 | 0.690 | 0.008 |
| | DBA/1 | 0.904 | 0.548 | 0.904 | 0.016 |
| | C3H/He | 0.200 | 0.534 | 1.200 | 0.028 |
| | SJL | 0.032 | 0.036 | 0.280 | 0.036 |

*Numbers underlined are significant

Of the four adjuvants tested, only the lipophilic adjuvant CGP 12908 induced responses in all four strains of mice that were not significantly different from those of the respective CFA groups, as regards antibody levels to either HCG or Structure (XII). The other lipophilic adjuvant CGP 16940, produced significantly lower levels of antibody to Structure (XII) in the mouse strains DBA/1 and C3H/He, and significantly lower levels of antibody to HCG in all four mouse strains. The hydrophilic adjuvant CGP 14767 produced Structure (XII) antibody levels significantly lower than those produced by CFA in only one mouse group, the strain DBA/1, while the Structure (XII) antibody levels produced by the other hydrophilic adjuvant CGP 11637 were significantly lower in the three mouse groups DBA/1, C3H/He and SJL than in the corresponding CFA groups. The HCG antibody levels produced by both the hydrophilic adjuvants CCG 11637 and 14767 were not significantly different from those of the corresponding CFA groups, only the SJL strain producing significantly different results in both cases.

Since the responses of the mice to immunization with the Structure (XII)/tetanus toxoid conjugate were more depen-

TABLE 14

| | | Adjuvant | | | | |
|---|---|---|---|---|---|---|
| | Mouse | CFA (Control) | CGP 11637 | CGP 14767 | CGP 12908 | CGP 16940 |
| Antigen | Strain | ng/ml (sd) | ng/ml (sd) | ng/ml (sd) | ng/ml (sd) | ng/ml (sd) |
| Structure (XII) | C57BL/6 | 117.7 (59.5) | 70.9 (34.3) | 53.0 (62.9) | 281.7 (237.4) | 110.0 (76.9) |
| | DBA/1 | 411.6 (268.2) | 42.5 (9.6) | 22.2 (14.5) | 528.3 (342.5) | 173.0 (37.4) |
| | C3H/He | 566.8 (169.9) | 84.0 (26.3) | 74.9 (7.4) | 66.4 (*) | 19.2 (11.6) |
| | SJL | 379.2 (330.1) | 60.1 (44.7) | 91.6 (57.9) | 415.3 (254.7) | 369.0 (319.7) |
| CG | C57BL/6 | 20.4 (6.1) | 18.3 (8.0) | 21.0 (5.8) | 47.2 (52.8) | 1.0 (1.2) |
| | DBA | 10.0 (4.0) | 10.6 (7.4) | 11.1 (12.2) | 45.2 (73.7) | <1.0 (0.0) |
| | C3H/He | 57.9 (47.9) | 21.5 (27.9) | 21.4 (12.4) | 31.6 (*) | <1.0 (0.0) |
| | SJL | 253.7 (413.0) | 13.8 (12.9) | 5.4 (0.5) | 45.9 (39.1) | 8.6 (7.4) |

(*) One mouse only (n = 5)

The data in Table 14 reveal significant differences among the four strains of mice immunized with CFA. The differences between the levels of antibody to Structure (XII) between the DBA/1 and C3H/He groups on the one hand and dent upon the adjuvant used than the strain of mouse injected, genetic differences among the various strains were difficult to assess. However, the C57BL/6 strain mice did not show any significant differences in Structure (XII) antibody levels with any of the four adjuvants tested, as compared with the CFA immunized mice. On the other hand, mice of the DBA/1 strain did show significantly lower Structure (XII) antibody levels with three of the four adjuvants tested, as compared with the CFA immunized mice. Accordingly, in some of the later experiments only these two strains of mice were used for assessing genetic differences.

Figure 7:
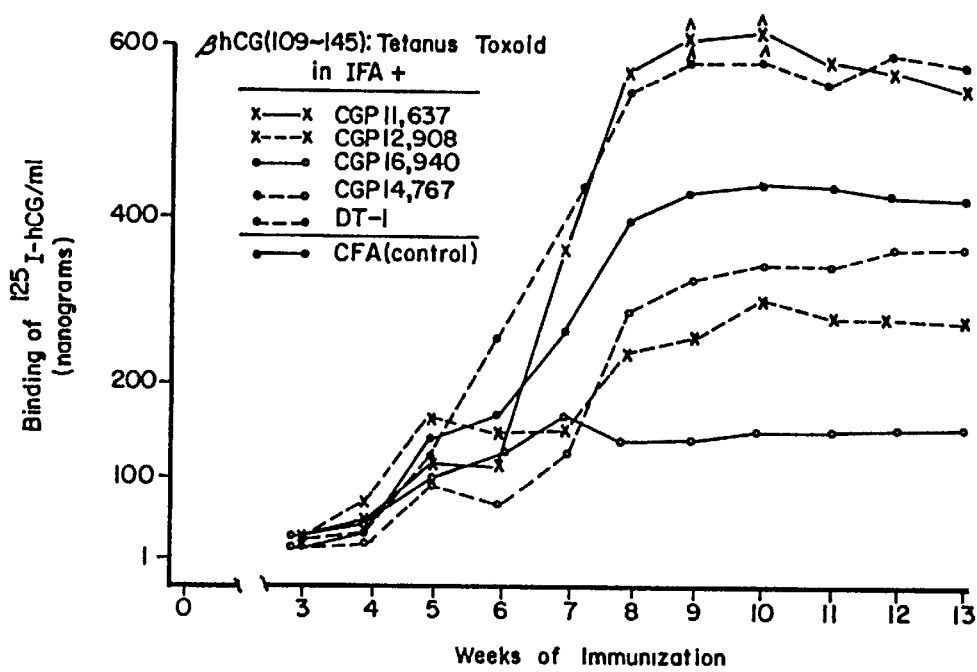
FIG. 7 shows the levels of antibody to HCG produced in rabbits by vaccines containing a tetanus-toxoid-coupled modified peptide and various adjuvants in Example XXXIII below.

A parallel series of tests using the same four adjuvants, as well as the hydrophilic adjuvant DT-1 in conjunction with Structure (XII)/tetanus toxoid conjugate and IFA, produced somewhat different results, as shown in FIG. 7, which shows the mean HCG antibody levels averaged over the groups of four rabbits used, from 3–13 weeks after primary immunization. As with the mouse tests, a group of four rabbits was immunized with the conjugate incorporated into CFA for comparison. FIG. 7 shows that the HCG antibody levels in all groups were substantially constant from the 9–13 weeks after primary immunization, and therefore statistical evaluation of the antibody levels was conducted after pooling data within each group during this five week period.

As compared with the CFA immunized rabbits, only the rabbits receiving the adjuvant CGP 16940 produced significantly lower HCG antibody levels ($p<0.05$). The rabbits receiving adjuvants CGP 11637 and DT-1 produced HCG antibody levels significantly greater than the rabbits receiving adjuvants CGP 16940 and 12908 ($p<0.05$), but not significantly higher than the rabbits receiving adjuvant CGP 14767 or the rabbits receiving CFA.

Further tests were conducted in mice and rabbits to determine the effects of the various vehicles on antibody levels. In the mice tests, groups of five mice from each of the strains C57BL/6 and DBA/1 were immunized with the conjugate of tetanus toxoid and Structure (XIV) (the 111–145 sequence of β-HCG with the N-terminal spacer sequence) in conjunction with one of the vehicles PBS, IFA, liposomes and Squalene/Arlacel. No adjuvants were used in immunizing the mice receiving the vehicles, but a group of mice from each strain were immunized with the conjugate incorporated into CFA for comparison purposes.

The mean Structure (XIV) and HCG antibody levels for each group of mice 35 and 52 days after the primary immunization are shown in Table 16 as between the CFA Control group with the groups receiving the various other vehicles by the aforementioned U-test are shown in Table 17 below. Table 17 shows that the Structure (XIV) antibody levels in the DBA/1 mice were significantly higher than those in the C57BL/6 mice at either 35 or 52 days after the primary immunization. In terms of HCG antibody levels the DBA/1 mice were significantly lower than those of the C57BL/6 mice 35 days after immunization, but not significantly lower 52 days after primary immunization.

The U-test factors in Table 17 show that, in the C57BL/6 mice groups 35 days after primary immunization, only the group receiving the IFA did not have significantly lower levels of antibodies to both Structure (XIV) and HCG than those of the mice receiving CFA. However, the results 52 days after primary immunization are strikingly different: no significant differences between Structure (XIV) or HCG antibody levels existed at that time between the mice receiving CFA and those receiving BPS, IFA or liposomes vehicles. Indeed, the Squalene/Arlacel vehicle immunized mice had levels of antibodies to both Structures (XIV) and HCG which were significantly higher than those of any other vehicle including CFA. The responses of the DBA/1 mice were not similar to those of the C57BL/6 mice. Thirty-five days after primary immunization, the four groups of DBA/1 mice immunized with the vehicles under test had Structure (XIV) antibody levels significantly greater than those of the mice receiving CFA, but only the group of mice receiving liposomes vehicle had HCG antibody levels significantly lower than the CFA group. In all the groups of DBA/1 mice 52 days after primary immunization, the antibody levels to both Structure (XIV) and HCG were not significantly different from the CFA group.

TABLE 16

| Mouse Strain | Vehicle | Sera 35 days after Primary Immunization Antibody Level M/L x $10^{10}$ (sd) | | Sera 52 days after Primary Immunization Antibody Level M/L x $10^{10}$ (sd) | |
|---|---|---|---|---|---|
| | | Structure (XIV) | HCG | Structure (XIV) | HCG |
| C57BL/6 | PBS | 3.2 (2.7) | 2.5 (1.2) | 3.1 (2.7) | 2.8 (1.8) |
| | IFA | 116.8 (90.4) | 107.9 (77.6) | 24.3 (11.4) | 15.1 (10.8) |
| | Liposomes | 2.0 (0.0) | 2.0 (0.0) | 13.5 (9.6) | 12.4 (8.3) |
| | Squalene/Arlacel | 22.5 (28.4) | 9.1 (10.0) | 397.1 (149.2) | 331.4 (153.3) |
| | CFA (Control) | 184.5 (107.6) | 141.6 (70.5) | 21.6 (25.9) | 12.5 (11.6) |
| DBA/1 | PBS | 54.0 (31.8) | 16.1 (8.6) | 94.4 (61.8) | 19.1 (14.5) |
| | IFA | 203.1 (174.3) | 25.6 (37.4) | 240.2 (137.5) | 21.1 (22.2) |
| | Liposomes | 2.1 (0.3) | 2.0 (0.0) | 74.0 (136.6) | 17.6 (21.3) |
| | Squalene/Arlacel | 23.0 (8.6) | 13.6 (5.9) | 205.2 (97.2) | 11.8 (10.0) |
| | CFA (Control) | 442.1 (74.2) | 40.0 (23.1) | 206.1 (130.5) | 14.2 (5.6) |

TABLE 17

| | CFA | Sera 35 days after Primary Immunization U-test (p*) for | | Sera 52 days after Primary Immunization U-test (p*) for | |
|---|---|---|---|---|---|
| Mouse Strain | Compared With | Structure (XIV) | HCG | Structure (XIV) | HCG |
| C57BL/6 | PBS | <u>0.004</u> | <u>0.004</u> | 0.178 | 0.052–0.082 |
| | IFA | 0.246 | 0.246 | 0.330 | 0.930–1.070 |
| | Liposomes | <u>0.008</u> | <u>0.008</u> | 0.842–1.000 | 0.842–1.000 |
| | Squalene/Arlacel | <u>0.008</u> | <u>0.008</u> | <u>0.016</u> | <u>0.016</u> |
| DBA/1 | PBS | <u>0.016</u> | 0.112 | 0.286 | 0.904 |
| | IFA | <u>0.032</u> | 0.310 | 1.000 | 0.842 |
| | Liposomes | <u>0.008</u> | <u>0.008</u> | 0.310 | 0.548 |
| | Squalene/Arlacel | <u>0.008</u> | 0.056 | 1.096 | 0.556 |

*Numbers underlined are significant at p = 0.05 level

A similar series of tests were run in rabbits using the four vehicles Squalane/Arlacel A, Squalene/Arlacel B, peanut oil and alum. These tests were conducted using the same Structure (XIV)/tetanus toxoid conjugate, but the adjuvant DT-1 was used. Again, a control group of rabbits were immunized with the conjugate emulsified in CFA without a vehicle. Antibody levels to HCG were measured throughout the 13 week immunization period and the data obtained from each group of rabbits at the week of peak antibody level were pooled with the values obtained from the same group one week earlier and one week later. The results are shown in Table 18 below. The HCG antibody levels in rabbits receiving Squalene/Arlacel were significantly higher than those of all other groups, including the rabbits receiving CFA. No significant differences in HCG antibody levels existed between the rabbits receiving Squalane/Arlacel and those receiving CFA, while the rabbits receiving peanut oil or alum vehicles had significantly lower HCG antibody levels than those receiving CFA.

The efficacy of the Squalene/Arlacel A vehicle in increasing the antibody levels in the injected animals is surprising, especially since Squalane/Arlacel has not previously been used as a vehicle in a vaccine, although Squalene is used in topical preparations such as ointments and cosmetics. Although the Squalane/Arlacel A vehicle was not as effective as the Squalene/Arlacel vehicle, it was as efficacious as CFA. Both the Squalene/Arlacel and the Squalane/Arlacel vehicles should be clinically acceptable for use in human beings, since they appear to produce little or no irritation at the sight of injection, whereas CFA is known not to be clinically acceptable for use in human beings since it tends to produce intense irritation, abscesses, etc. at the point of injection.

Table 20 below shows data similar to those in Table 19 but relating to Structure (XIV) antibody levels instead of HCG antibody levels. Analysis of the date in Table 20 shows that 35 days after primary immunization in the C57BL/6 mice, mice receiving the adjuvant CGP 18177 produced significantly higher levels of antibodies than the group receiving adjuvant CGP 19835 ($p<0.05$). However, the similar differences at 52 days after primary immunization were not significant at the $p=0.05$ level. Comparison of the three adjuvants of the DBA/1 mice 35 days after primary immunization shows no significant differences between the adjuvants in Squalene/Arlacel or peanut oil vehicles but the Structure (XIV) antibody levels produced by CGP 18177 in liposomes vehicle were significantly higher than those produced by CGP 19835 in the same vehicle ($p<0.05$). The results 52 days after primary immunization show the same pattern of significant differences as the results 35 days after primary immunization.

While mean HCG antibody levels were generally higher in mice immunized with Squalene/Arlacel vehicle and Structure (XIV) antibody levels were consistently higher using this vehicle, regardless of adjuvant or mouse strain, these differences were not significant in view of the variability in the responses of the mice. Although no significant differences were found between the two strains of mice as regards to HCG antibody levels, the DBA/1 mice produced higher mean Structure (XIV) antibody levels in all vehicle and adjuvant groups than the C57BL/6 mice although the differences were not statistically different.

TABLE 18

| Vehicle | n | Minimum | Median | Maximum | Mean | 95% C.I. | sd | p* |
|---|---|---|---|---|---|---|---|---|
| | | | | Antibody Level M/L × $10^{10}$ | | | | |
| CFA (Control) | 12 | 52.4 | 150.8 | 320.2 | 161.3 | 101.7–220.9 | 93.7 | |
| Squalene/Arlacel A | 11 | 189.0 | 312.6 | 833.7 | 400.1 | 225.7–574.4 | 226.7 | 0.01 |
| Squalane/Arlacel A | 11 | 44.2 | 150.6 | 290.0 | 168.5 | 114.5–222.5 | 80.4 | NS |
| Peanut Oil | 9 | 12.5 | 22.5 | 27.1 | 21.3 | 17.5–25.1 | 4.9 | <0.001 |
| Alum Precipitate | 12 | 5.8 | 8.4 | 16.1 | 9.9 | 7.9–11.9 | 3.2 | <0.001 |

*Probability, compared with CFA. NS = not significant ($p \geq 0.05$)

To evaluate simultaneously combinations of various adjuvants and various vehicles, and thus to detect any second order effects due to the interactions of particular adjuvants with particular vehicles, groups of five or six mice from each of the strains C57BL/6 and DBA/1 were immunized with preparations comprising the same Structure (XIV)/tetanus toxoid conjugate used in the preceding tests in combination with one of the synthetic adjuvants CGP 18177, 18741 or 19834 and one of the three vehicles Squalene/Arlacel, liposomes and peanut oil. As in the preceding test described above with reference to Tables 16 and 17, HCG antibody levels were determined in sera collected 35 and 52 days after primary immunization, and the results are shown in Table 19 below. The data in Table 19 reveal no significant differences between the levels of antibodies in the groups of mice injected with the same adjuvant in different vehicles, nor between the groups receiving the same vehicle and different adjuvants, at either 35 or 52 days after primary immunization (i.e. $p>0.05$ in all cases). Furthermore, no differences significant at the $p=0.05$ level were detected between the levels between corresponding groups of mice of difference strains.

TABLE 19

| Adjuvant | Vehicle | Sera 35 days after Primary Immunization Antibody Level M/L × $10^{10}$ (sd) in | | Sera 52 days after Primary Immunization Antibody Level M/L × $10^{-10}$ (sd) in | |
|---|---|---|---|---|---|
| | | C57BL/6 | DBA/1 | C57BL/6 | DBA/1 |
| CGP 18177 | Squalene/Arlacel | 17.7 (9.4) | 9.6 (14.6) | 10.2 (4.9) | 12.3 (12.8) |
| | Liposomes | 14.8 (4.9) | 10.1 (1.7) | 16.7 (5.4) | 15.5 (8.3) |
| | Peanut Oil | 9.1 (8.8) | 15.2 (6.4) | 13.3 (14.8) | 7.1 (2.1) |
| CGP 18741 | Squalene/Arlacel | 13.7 (6.5) | 10.5 (8.4) | 7.8 (3.9) | 9.1 (8.0) |
| | Liposomes | 9.6 (6.5) | 8.8 (5.1) | 5.6 (6.6) | 13.8 (5.2) |
| | Peanut Oil | 23.9 (8.4) | 13.9 (9.3) | 4.6 (3.9) | 10.5 (6.9) |
| CGP 19835 | Squalene/Arlacel | 13.5 (6.6) | 13.2 (8.9) | 10.4 (7.1) | 16.8 (3.2) |
| | Liposomes | 7.4 (9.4) | 16.7 (14.6) | 2.0 (0.0) | 15.2 (9.8) |
| | Peanut Oil | 10.7 (7.4) | 11.2 (5.4) | 2.7 (1.5) | 5.7 (*) |

(*) One mouse only from n = 5

TABLE 20

| Adjuvant | Vehicle | Sera 35 days after Primary Immunization Antibody Level M/L × $10^{-10}$ (sd) in | | Sera 52 days after Primary Immunization Antibody Level M/L × $10^{-10}$ (sd) in | |
|---|---|---|---|---|---|
| | | C57BL/6 | DBA/1 | C57BL/6 | DBA/1 |
| CGP 18177 | Squalene/Arlacel | 50.1 (43.1) | 160.7 (120.1) | 163.7 (100.4) | 419.4 (345.4) |
| | Liposomes | 32.2 (9.4) | 104.0 (35.4) | 35.0 (21.5) | 206.4 (3.5) |
| | Peanut Oil | 16.8 (13.3) | 69.4 (36.5) | 92.6 (106.0) | 91.4 (59.2) |
| CGP 18741 | Squalene/Arlacel | 21.4 (10.9) | 130.4 (115.5) | 65.8 (42.9) | 371.7 (364.7) |
| | Liposomes | 10.9 (11.3) | 54.0 (28.4) | 30.3 (40.3) | 134.5 (62.0) |
| | Peanut Oil | 2.0 (0.0) | 89.4 (127.0) | 27.1 (38.7) | 46.2 (31.4) |
| CGP 19835 | Squalene/Arlacel | 18.8 (6.6) | 200.2 (201.8) | 95.4 (70.5) | 195.9 (177.3) |
| | Liposomes | 6.0 (8.9) | 19.5 (13.2) | 44.5 (36.4) | 92.7 (38.4) |
| | Peanut Oil | 2.0 (0.0) | 148.1 (141.7) | 45.4 (57.5) | 7.2 (*) |

(*) One mouse from n = 5

A similar series of tests were then carried out in rabbits using the same Structure (XIV)/tetanus toxoid conjugate, the adjuvants CGP 18177, 18741, and 19835 tested in mice, plus the additional adjuvants CGP 11637 and DT/1, using groups of four rabbits and Squalene/Arlacel as the vehicle. Again, a control group of rabbits were immunized with the conjugate incorporated into CFA without a vehicle. The mean HCG antibody levels in sera collected from the various groups of rabbits weekly from 3–12 weeks after primary immunization are shown in Table 21 below, together with the corresponding standard deviations. The data in Table 21 show that the highest antibody levels were achieved in rabbits receiving the adjuvants CGP 11637 and DT/1 10 weeks after primary immunization. Comparison of the antibody levels produced by these adjuvants with the control group receiving CFA showed that the increases in antibody levels with both adjuvants were significant at the p=0.05 level. Adjuvant CGP 18177 also produced higher antibody levels than CFA, the difference being significant at the p=0.05 level, and the differences between the antibody levels produced by the three adjuvants CGP 11637, DT/1 and CGP 18177 are not significant at the p=0.05 level. The adjuvants CGP 19835 and 18741 produced antibody levels which were lower than the CFA rabbits, the difference being significant at the p=0.05 level.

TABLE 21

| Weeks After Primary Immunization | Mean Antibody Level-$^{125}$I-HCG M/L × $10^{10}$ (sd) Adjuvant | | | | | |
|---|---|---|---|---|---|---|
| | CFA (Control) | CGP 11637 | CGP 19835 | CGP 18741 | CGP 18177 | DT-1 |
| 3* | 14.3 (8.6) | 16.3 (11.8) | 19.3 (8.8) | 5.9 (1.4) | 19.9 (19.2) | 31.1 (8.4) |
| 4 | 69.0 (26.8) | 177.8 (105.0) | 286.7 (113.8) | 9.8 (4.8) | 215.1 (207.6) | 145.1 (50.6) |
| 5 | 158.1 (88.8) | 211.9 (105.2) | 140.3 (82.2) | 6.2 (0.6) | 204.6 (137.6) | 184.1 (54.2) |
| 6* | 150.4 (66.0) | 297.2 (152.4) | 172.0 (74.4) | 8.9 (7.4) | 218.2 (46.2) | 268.6 (170.4) |
| 7 | 171.2 (193.4) | 381.2 (228.8) | 123.4 (46.6) | 81.1 (46.6) | 441.9 (144.2) | 371.5 (183.8) |
| 8 | 185.2 (200.4) | 418.6 (292.4) | 138.9 (39.2) | 75.4 (64.4) | 544.9 (226.6) | 366.2 (229.2) |
| 9 | 238.6 (143.4) | 480.0 (260.6) | 105.2 (15.4) | 74.9 (45.6) | 456.2 (171.0) | 654.8 (380.6) |
| 10 | 324.5 (244.0) | 708.6 (329.0) | 151.3 (38.4) | 121.8 (51.4) | 631.0 (377.8) | 729.4 (455.4) |

TABLE 21-continued

Mean Antibody Level-$^{125}$I-HCG M/L × $10^{10}$ (sd)

| Weeks After Primary Immunization | Adjuvant | | | | | |
|---|---|---|---|---|---|---|
| | CFA (Control) | CGP 11637 | CGP 19835 | CGP 18741 | CGP 18177 | DT-1 |
| 11 | 210.8 (140.0) | 628.5 (445.8) | 169.3 (40.0) | 156.8 (25.0) | 584.0 (213.4) | 627.5 (340.8) |
| 12 | 195.3 (139.0) | 398.5 (350.4) | 107.8 (20.2) | 97.6 (10.6) | 270.0 (175.2) | 559.0 (460.4) |

*Booster immunization given at this time

A final series of tests were run in mice to determine the effect of coupling one of the adjuvants to the peptide/tetanus toxoid conjugate instead of merely administering the peptide/tetanus toxoid conjugate mixed with the adjuvant. Groups of five mice from each of the strains C57BL/6 and DBA/1 were immunized with the Structure (XIV)/tetanus toxoid/CGP 11637 conjugate described above, separate groups of mice being immunized with the conjugate in association with each of the vehicles PBS, IFA, liposomes and Squalene/Arlacel. As before, a Control group from each strain was immunized with the conjugate incorporated into CFA for comparison purposes.

Figure 8:
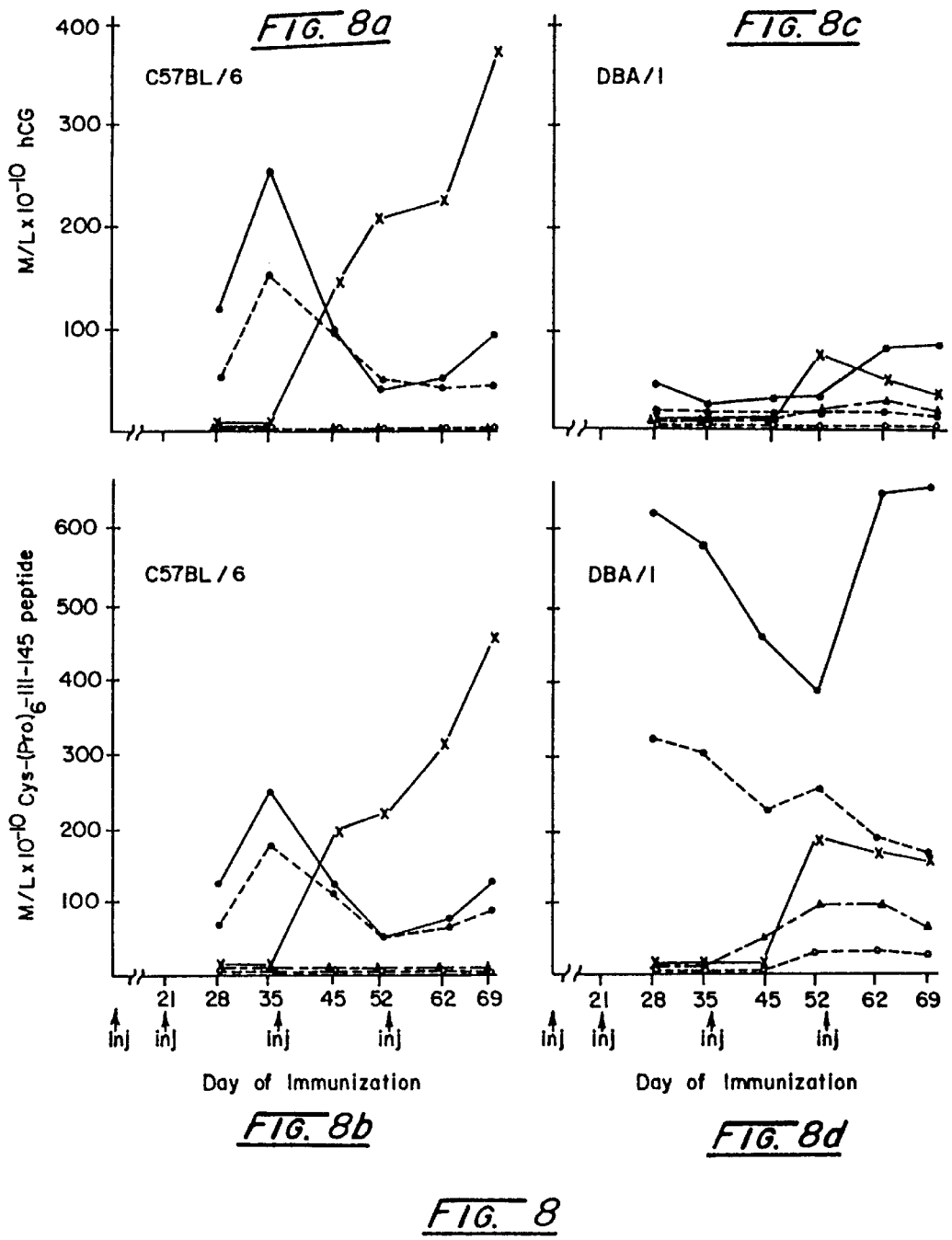
FIG. 8 shows the levels of antibodies to HCG and peptide produced in mice of various species by a vaccine comprising a tetanus-toxoid-coupled modified peptide coupled to various adjuvants in Example XXXIII below.

FIG. 8 shows the mean HCG and Structure (XIV) antibody levels in the mice as a function of time after primary immunization (the coding for the various vehicles in FIG. 8 is the same as that in FIG. 7). FIG. 8a shows the HCG antibody levels of the C57BL/6 mice. The elevated antibody levels produced by CFA and IFA 35 days after primary immunization are not significant at the p=0.05 level and were not sustained after the booster immunizations at 33 and 55 days. The mice receiving the conjugate in Squalene/Arlacel vehicles did not respond significantly until the third bleeding, 45 days after primary immunization, but there HCG antibody levels increased progressively thereafter and were higher by an amount significant at the p=0.05 level as compared with those of the other mouse groups. The Structure (XV) antibody levels of the same mice shown in FIG. 8b parallel those of the HCG antibody levels and statistical analysis shows that the same differences are significant.

The HCG antibody levels of the DBA/1 mice shown in FIG. 8c are considerably lower than those of the corresponding C57BL/6 mice. Fifty-two days after primary immunization, the HCG antibody levels in the DBA/1 mice receiving the Squalene/Arlacel vehicle were not significantly different from those of the CFA Control group (p>0.05), but were significantly higher than the levels achieved in the mice receiving the other vehicles (p<0.0). Sixty-nine days after primary immunization, there were no differences significant at the p=0.05 level between any of the groups of DBA/1 mice. However, as shown in FIG. 8d, unlike the results obtained with the C57BL/6 mice, in the DBA/1 mice, the antibody levels to Structure (XIV) do not follow the antibody levels to HCG. The Structure (XIV) antibody levels in the DBA/1 mice receiving CFA or IFA were elevated 28 days after the primary immunization and thereafter declined until day 52. Later, the CFA immunized mice levels rose in response to the booster injection administered at day 55, while the antibody levels in the IFA mice continued to fall. No differences significant at the p=0.05 level were found between the antibody levels in the mice receiving CFA, IFA or Squalene/Arlacel 52 days after the primary immunization, but at this time the differences between the mice receiving CFA and those receiving PBS and liposomes vehicles were significant at the p=0.05 level.

After 69 days from primary immunization, while the difference between the CFA groups and the remaining vehicles were significant at the p=0.05 level, the differences between the other groups were not significant at this level.

The experimental results described above clearly demonstrate the efficacy of some of the synthetic adjuvants in increasing antibody production when administered in conjunction with the modified polypeptide of the invention. Some of the adjuvants, in particular CGP 11637 and 18177 and DT/1, when administered in certain vehicles, especially IFA and Squalene/Arlacel produced antibodies exceeding those produced by CFA. In general, the hydrophilic muramyl peptide adjuvants were superior to the lipophilic adjuvants in enhancing the antibody production caused by the hydrophilic Structure (XIV) /tetanus toxoid conjugate. The experimental results also show that the delivery system used to administer the antigen and adjuvant is of critical importance in producing an enhanced response to the conjugate. For example, the antibody responses of the C57BL/6 mice which received the conjugate in Squalene/Arlacel without adjuvant were greater than those of the mice receiving the conjugate in CFA. Adding an adjuvant to this vehicle produced only a slight increase in the antibody levels. These observations are confirmed by those in rabbits receiving the conjugate and the synthetic adjuvant in different vehicles, and different adjuvants in the same vehicle. Squalane/Arlacel and peanut oil emulsions were efficacious, though less effective than Squalene/Arlacel.

To sum up, based upon all the foregoing data it appears that the optimum vehicle was Squalene/Arlacel, which was superior to the others in almost every formulation and that the best adjuvants are CGB 11637 and DT/1, which were more efficacious in various vehicles than other adjuvants tested simultaneously. Squalane/Arlacel was also a highly acceptable vehicle although somewhat less efficacious than Squalene/Arlacel.

EXAMPLE XXXIV

This example illustrates a use of a modified polypeptide of the invention in repressing a carcinoma which produces a chorionic gonadotropin-like material. This material by John A. Kelen, Arnost Kolin and Hernan F. Acevedo is in press and will shortly appear in Cancer.

The rat mammary adenocarcinoma R 3230 AC has been shown, using immunocytochemical, radioimmunoassay (RIA) and bioassay methods in tissue sections and cell cultures to product a chorionic gonadotropin (CG)-like material; however this CG-like material cannot be detected in the sera of the animals bearing the carcinoma. The detection of the CG-like material is described in:

(a) Malkin et al., "Immunohistochemical Detection of Ectopic Hormones in Experimental Rat Tumors", in F. G. Lehmann (ed.), *Carcino-embryonic Proteins*, Vol. 2, Elsevier-North Holland Biomedical Press, New York, Amsterdam (1979), pp. 751–758.

This adenocarcinoma can be propagated in cell culture and its cells retain their morphology and malignant characteristics. Intravenous injection of these cells into isologous Fischer 344 rats gives rise to numerous foci of this neoplasm in the lungs within 8–10 days, the animals then becoming very sick and then dying within 12–15 days.

The R 3230 adenocarcinoma (obtained from Dr. A. Bogden, Mason Research Institute, Worcester, Mass.) was cultured from explants of subcutaneous tumors grown for 20–21 days in Fischer 344 female rats. The cultures were maintained in RPMI 1640 medium supplemented with 10% fetal cough serum. Upon reaching confluency, the cells were dispersed by means of trypsin-EDTA (1:250) and passaged five times. During the early stationary growth phase, the cultured cells were dispersed for in vivo administration. The cell density was determined using a hemocytometer and viability was tested by the Trypan blue exclusion method. One million cells were then injected into the tail vein of each of the experimental animals, which were 100 female Fischer 344 rats weighing 130–150 g. The animals were divided into two matched control groups of 15 animals each and a test group of 70 animals. They were individually caged, fed Purina (Registered Trade Mark) chow and tap water ad libitum. All animals except six from the test group were sacrificed at intervals by cervical dislocation for necropsy studies. The lungs, livers, spleen and kidneys were examined and processed for paraffin sections and H&E staining in order to detect neoplastic foci, the diameter of the foci being measured with an eye piece micrometer. All animals were also bled before sacrifice and the serum tested for the presence of antibodies to CG.

The test group of 70 rats received, prior to the injection of carcinoma cells, a β-HCG/tetanus toxoid modified polypeptide of the invention. This β-HCG conjugate, and its method of preparation, is described in U.S. Pat. No. 4,161,519 to Talwar and in the following papers written by the same author and others:

(b) *Proc. Natl. Acad. Sci. U.S.A.*, 73, 218–222 (1976);

(c) *Contraception*, 18, 19–21 (1978);

(d) *Fertil. Steril.*, 34, 328–335 (1980).

The conjugate was administered in saline once per week for a period of three weeks, approximately 1.3 µg. being given at each injection and the last injection being given two weeks before administration of the carcinoma cells. In order to study the effect of the conjugate over an extended period, a number of animals selected at random were sacrificed for autopsy, as follows (the day when the carcinoma cells were injected being taken as day 0):

| Day | Number of Rats Sacrificed |
|---|---|
| 3 | 2 |
| 5 | 5 |
| 8 | 5 |
| 10 | 36 |
| 22 | 10 |
| 28 | 4 |
| 120 | 2 |

One of the two control groups was administered highly purified tetanus toxoid (obtained from Connaught Laboratories, Toronto, Ontario, Canada) at a rate of 0.7 µg. per injection, following the same injection schedule as the test group followed with the conjugate. Thus, this control group received a dose of tetanus toxoid substantially equal to that received in the conjugate by the test animals. The second control group received no treatment other than the tumor suspensions. All the animals from the test group were sacrificed for autopsy on day 10.

Testing for the presence of HCG antibodies was performed using the HCG-b-RIA kit, Quantitative Method II (manufactured by Serono Laboratories, Braintree, Mass.). To the cold standard HCG, HCG free serum and $^{125}$I-HCG, an aliquot of the rat serum was added. After overnight incubation, the original protocol of the kit was followed in the subsequent procedure. If all the labeled HCG was precipitated (thus indicating a high antibody titer) the test was repeated with appropriately diluted rat serum.

All the animals in the two control groups, sacrificed 10 days after injection of the tumor cells, showed multiple lung foci of neoplastic cells in accordance with the normal progress of this carcinoma. None of the 30 animals in the control groups showed neoplasms in any other organs. The qualitative histological appearance of the pulmonary tumor deposits was practically identical in every animal. The neoplasm is a moderately differentiated adenocarcinoma rarely producing glandular lumina. The mitotic rates are high, but tumor necrosis and inflammatory reactions are absent. The tumor nodules range in size from a few cells to more than one millimeter in diameter and are uniformly distributed throughout the lung parenchyma. Using a 2.5 X objective, from 5–10 tumor nodules were present in every low power camera field in the controlled animals. In contrast, the test animals that had received the β-HCG/tetanus toxoid conjugate rarely displayed more than 1 to 4 metastatic nodules not exceeding 0.3 mm. in diameter in the entire lung sections 8–10 days after administration of the tumor cells, so that only a few camera fields could be found containing a single metastatic focus. Most lung parenchyma were completely free of neoplasms. The histological appearance of the neoplasms in the test animals was the same as that in the controls.

In all the rats receiving the conjugate, a significant antibody titer was found, antibody levels capable of precipitating 200 mIU of HCG standard per milliliter of serum being consistently determined. This titer persisted for up to 120 days after receipt of the tumor cells and continued to protect at that time against formation of metastatic lung foci after a new intravenous seeding with the tumor cells. In contrast, neither of the control groups showed any measurable HCG antibody levels, regardless of whether the rats had or had not received the tetanus toxoid.

Thus, the protective effects of immunization with the conjugate prior to injection with the tumor cells were demonstrated by the test animals being alive 20 days after injection of the tumor cells (at which time, 100% mortality would be expected in unprotected animals), by the absence of lung pathology in the animals sacrificed more than 20 days after injection of the tumor cells, by the long term survival (more than six months) and lack of deterioration in the six test animals that were not sacrificed, and by the fertility of these six surviving test animals, several of which produced normal litters after termination of the 120 day observation period. This long term survival of all the six animals and absence of any deterioration therein is especially surprising in view of the virulence of the R 3230 A carcinoma chosen for study, since previous work has indicated that no rats receiving the intravenous injection of tumor cells received by these test animals can be expected to survive for more than about 20 days.

Since there are no detectable levels of serum HCG associated with this carcinoma in rats, the absence of pathological changes in the organs investigated and the maintenance of the reproductive functions in the surviving test rats suggest that the antibodies act at the level of the cell membrane, probably in a cytotoxic manner, although the above experimental results are not sufficient to prove this hypothesis.

EXAMPLE XXXV

This example illustrates the use of a modified polypeptide of the invention coupled to diphtheria toxoid in repressing fertility in baboons.

A modified polypeptide of the invention based upon Structure (XII) above was prepared in exactly the same manner in Example XXXI except that the peptide was conjugated to diphtheria toxoid instead of tetanus toxoid. Also, the resultant conjugate, again containing about 22 peptides per 100,000 daltons of the toxoid, was dissolved in a solution of the muramyl dipeptide CGP 11637 used in Example XXXIII, instead of the Complete Freunds' adjuvant used in Example XXXI. The resultant conjugate/ adjuvant mixture was emulsified with an equal volume of the 4:1 v/v Squalene/Arlacel A vehicle used in Example XXXIII. Again, the control animals received diphtheria toxoid in an amount equal to that received as part of the conjugate by the test animals. All details regarding animal feeding, group size, animal housing, mode of administration of vaccine and blood testing were exactly as in Example XXXI.

The length of the menstrual cycles and the luteal phase progesterone levels for both the test and control groups were measured for three menstrual cycles before immunization and five menstrual cycles after immunization. The results are shown in Table 22 below (which is directly comparable with Table 7 of Example XXXI). The data in Table 22 shows that, as in the previous experiment, no significant differences existed between the lengths of menstrual cycle and luteal phase progesterone levels of the two groups of baboons either before or after immunization.

Table 23 below shows the antibody levels to Structure (XII), baboon chorionic gonadotropin and human chorionic gonadotropin produced in the test animals injected with the conjugate during the five menstrual cycles following immunization. As in Example XXXI, the antibody levels were determined from serum drawn from the early luteal phase of each menstrual cycle. Thus, the data in Table 23 may be compared directly with those in Table 5 of Example XXXI. Comparing Tables 5 and 23, it will be seen that the diphtheria-toxoid-containing conjugate produced slightly lower levels of antibodies to baboon chorionic gonadotropin than did the tetanus-toxoid-containing conjugate (though this difference does not appear to be significant), but rather higher levels of antibodies to human chorionic gonadotropin (and the differences between the two groups for menstrual cycles Nos. 4 and 5 would appear to be significant).

As in Example XXXI, each of the baboons was mated during the course of the third menstrual cycle following immunization and also mated during the two subsequent menstrual cycles unless, of course, a previous mating produced a pregnancy. The results are shown in Table 24, which is directly comparable with Table 8 of Example XXXI. Of the control animals immunized only with diphtheria toxoid, 11 out of 15 became pregnant on the first mating, three of the remaining four became pregnant after the third mating. Thus, a total of 20 matings produced 14 pregnancies and a fertility rate of 70%. On the other hand, in the test animals immunized with the conjugate, none of the 15 baboons became pregnant during the first mating, only one of the remaining baboons became pregnant at the second mating, and at the third mating, another one of the 14 remaining baboons became pregnant. Thus, a total of 44 matings produced only two pregnancies for a fertility rate of 4.6%. Although statistical comparisons are difficult because of the very small numbers of pregnancies involved in the conjugate-immunized baboons, it thus appears that the vaccine used in this Example containing Structure (XII)/ diphtheria toxoid conjugate is more effective in preventing conception in baboons than the vaccine used in Example XXXI.

A detailed immunosafety study in 48 female baboons using the same vaccine revealed no detectable alteration in serum chemistry, urinalysis, immune complex formation, auto-immunity or any hypersensitivity reactions. Histopathological evaluation of numerous tissues from sacrifice of all animals revealed no evidence of pathology from immunization. Antisera raised in these baboons failed to react with any pituitary glycoprotein hormone, thus showing that the antibodies formed in response to the vaccine did not cross-react with LH or FSH. No change in endogenous baboon hormone levels was observed following injections of the vaccine.

TABLE 22

Length of menstrual cycles and luteal phase progesterone levels

| Baboons Immunized With | Menstrual Cycles | | | | | | | |
|---|---|---|---|---|---|---|---|---|
| | Pre-Immunization | | | Post-Immunization | | | | |
| | −3 | −2 | −1 | 1 | 2 | 3 | 4 | 5 |
| Diphtheria Toxoid | | | | | | | | |
| Cycle Length (days) | | | | | | | | |
| Mean | 34.4 | 33.5 | 33.2 | 32.7 | 33.1 | 34.0 | 30.0 | 31.0 |
| SE | 1.0 | 0.9 | 0.6 | 0.7 | 0.8 | 0.7 | — | — |
| n[(1)] | 15 | 15 | 15 | 15 | 15 | 4 | 1 | 1 |
| Progesterone (ng/ml) | | | | | | | | |
| Mean | 6.9 | 6.8 | 6.0 | 4.3 | 6.0 | 7.0 | 5.9 | 6.0 |
| SE | 0.6 | 0.5 | 0.4 | 0.5 | 0.5 | 0.9 | — | — |
| n[(1)] | 15 | 15 | 15 | 15 | 15 | 4 | 1 | 1 |
| Conjugate | | | | | | | | |
| Cycle Length (days) | | | | | | | | |
| Mean | 33.2 | 32.7 | 34.1 | 33.9 | 32.7 | 32.1 | 32.2 | 32.5 |
| SE | 1.0 | 0.9 | 0.8 | 0.7 | 0.8 | 1.0 | 0.6 | 0.6 |
| n[(1)] | 15 | 15 | 15 | 15 | 15 | 15 | 14 | 13 |
| Progesterone (ng/ml) | | | | | | | | |
| Mean | 6.7 | 6.8 | 5.7 | 5.8 | 5.7 | 5.8 | 6.3 | 6.8 |
| SE | 0.6 | 0.7 | 0.6 | 0.8 | 0.7 | 0.4 | 0.4 | 0.5 |
| n[(1)] | 15 | 15 | 15 | 15 | 15 | 15 | 14 | 13 |

[(1)]decreases as a result of pregnancy

TABLE 23

Antibody levels produced by female baboons against Structure XII, baboon chorionic gonadotropin and human chorionic gonadotropin after immunization.
Values were determined from serum samples obtained during the early luteal phase of each menstrual cycle

| Antibody Reactive To | Antibody level during menstrual cycle | | | | |
|---|---|---|---|---|---|
| | 1 | 2 | 3 | 4 | 5 |
| | | | moles/liter × $10^{-10}$ | | |
| Structure (XII) | | | | | |
| Mean | 41.4 | 186.0 | 205.6 | 252.0 | 284.1 |
| SD | 28.6 | 84.1 | 67.5 | 118.7 | 99.7 |
| 95% CI | (25.6–57.3) | (139.4–232.5) | (168.3–243.0) | (186.1–317.7) | (226.5–341.7) |
| Baboon Chorionic Gonadotropin | | | | | |
| Mean | 0.7 | 3.7 | 5.5 | 7.7 | 9.0 |
| SD | 0.6 | 3.3 | 3.4 | 4.8 | 4.8 |
| 95% CI | (0.3–1.0) | (1.9–5.6) | (3.6–7.3) | (5.0–10.4) | (6.3–11.8) |
| Human Chorionic Gonadotropin | | | | | |
| Mean | 31.9 | 160.0 | 172.1 | 205.5 | 224.8 |
| SD | 23.9 | 77.7 | 55.0 | 108.2 | 89.8 |
| 95% CI | (18.7–45.2) | (117.0–203.1) | (141.6–202.5) | (145.5–265.4) | (172.9–276.6) |
| Number of Animals | 15 | 15 | 15 | 15 | 14 |

TABLE 24

Comparison of fertility rates for female baboons immunized with Diphtheria Toxoid with those immunized with conjugate.

| Baboons Immunized With | Mating Cycle | | | Totals |
|---|---|---|---|---|
| | 1 | 2 | 3 | |
| Diphtheria Toxoid | | | | |
| No. Mated | 15 | 4 | 1 | 20 |
| No. Pregnant | 11 | 3 | 0 | 14 |
| Fertility Rate (%) | 73.3 | 75.0 | 0 | 70.0 |
| Conjugate | | | | |
| No. Mated | 15 | 15 | 14 | 44 |
| No. Pregnant | 0 | 1 | 1 | 2 |
| Fertility Rate (%) | 0 | 6.7 | 7.1 | 4.6 |

EXAMPLE XXXVI

This example illustrates the effect of a vaccine of this invention in retarding the growth of Lewis lung carcinoma tumors in mice.

The mice used in these experiments were six-week old mice of the strain C57BL/6J, obtained from the same source as in Example II. The mice were divided into a test group of 20 animals and a control group of 17 animals. The test animals were immunized using the same vaccine as described in the second paragraph of Example V above, each injection comprising 200 μg. of conjugate and 100 μg. of adjuvant given subcutaneously in the lower back. Following the first injection, booster immunizations were given 4, 12, and 23 weeks later. The control group of mice were given immunizations at the same time, but the vaccine used contained only vehicle. Two days after the final immunization, each mouse was inoculated subcutaneously in the lower back with approximately one million viable cells of transplatable Lewis lung carcinoma. Measurements of the volume of the tumor were made 10, 14 and 17 days after tumor implantation and then, on day 18, the mice were sacrificed and the tumor removed and weighed.

TABLE 25

Comparison of tumor volumes and weights in mice implanted with Lewis Lung Carcinoma following immunization with vehicle or

| Mice Immunized With | Mean Tumor Volume-cm$^3$ (±s.e.m.) Day of Tumor Growth | | | Mean Tumor Weight in gms (±s.e.m.) |
|---|---|---|---|---|
| | 10 | 14 | 17 | Day 18 |
| Vehicle | 1.89 (0.32) | 5.20 (0.78) | 8.83 (1.14) | 7.00 (0.88) |
| Conjugate | 1.23 (0.22) | 2.94 (0.34)* | 5.22 (0.63)* | 4.13 (0.50)* |

*Significantly different ($p < 0.05$) from vehicle group

The results in Table 25 above show that the conjugate-immunized mice showed significant smaller tumors than the control group, the average reduction in tumor volume and weight being about 40%.

EXAMPLE XXXVII

This example illustrates the effect of a vaccine of the invention in increasing the survival rate of mice suffering from viral-induced leukemia.

The mice used in this experiment were six-week old female mice of SJL/J strain. A test group and a control group, each containing approximately 20 mice were selected at random and were immunized in the same manner as in Example XXXVI above, the test animals receiving the vaccine containing the peptide/diphtheria toxoid conjugate and the control group receiving the vaccine containing only the vehicle. However, in this experiment a different immunization schedule was followed: the original immunization was followed by booster immunizations 4, 9, 20 and 29 weeks later. Six weeks after the first immunization (i.e. two weeks after the second immunization) each mouse was injected with approximately 1 million Friends' Leukemia Virus and the mice were observed daily for deaths. The results are shown in Table 26 below and from the results in this table it will be seen that the vaccine of the invention provided complete protection against mortality caused by the leukemia virus whereas more than 60% of the control group succumbed.

TABLE 26

Comparison of survival rates in mice inoculated with Friends' Leukemia Virus following immunization with vehicle or conjugate

| Days After Inoculation | Survival Rate - % Group Immunization With | |
|---|---|---|
| | Vehicle (Control) | Conjugate |
| 0 | 100.0 | 100.0 |
| 22 | 87.5 | 100.0 |
| 29 | 75.0 | 100.0 |
| 98** | 75.0 | 100.0 |
| 160 | 56.3 | 100.0 |
| 163** | 56.3 | 100.0 |
| 166 | 43.8 | 100.0 |
| 175 | 37.5 | 100.0 |
| 180 | 37.5 | 100.0 |

**Day of booster immunization

EXAMPLE XXXVIII

This example illustrates the effect of a conjugate usable in the vaccines of the invention in retarding the growth of a sarcoma tumor in mice.

Sixty mice of the AKR strain were divided at random into a test group and a control group each comprising 30 mice. The test group were then immunized in the same manner as in Examples XXXVI and XXXVII with a vaccine comprising the same conjugate as in those Examples dissolved in Freund's Complete Adjuvant, while the control group simply received the Freund's Adjuvant. Booster immunizations were given to each group three and seven weeks after the first immunization. Ten days after the third immunization, the mice were inoculated with approximately 2 mm$^3$. of Ridgeway Osteogenic Sarcoma cells, and the mice were observed to see if the tumor survived. In the mice in which the tumor survived, tumor volume measurements were made 22, 26, 29, 31, 33, 38, 40 and 43 days after inoculation with the Sarcoma. The average tumor volume in the surviving mice of each group in which the tumor survived are shown in Table 27 below. The results in Table 27 show that the conjugate substantially reduced the rate of tumor growth. The later results should be interpreted with some caution because they are affected by the numbers of mice surviving; for example, at day 43, seven of the conjugate-immunized mice but only five of the vehicle-immunized mice were surviving and naturally the mice having the largest tumors tended to succumb first so that the figure for average tumor volume in the vehicle-immunized mice at day 43 is thus artificially reduced by the deaths of certain mice. Nevertheless, the results in Table 27 do show a significant reduction in the rate of tumor growth in the conjugate-immunized mice.

The mice were also bled ten days after the final immunization and serum tested for the presence of β-hCG antibodies; all the mice immunized with the conjugate had produced such antibodies.

TABLE 27

Comparison of tumor volumes in mice inoculated with Ridgeway osteogenic Sarcoma following immunization with vehicle or conjugate.

| Day of Tumor Growth | Mean Tumor Volume-cm$^3$ Group Immunized With | |
|---|---|---|
| | Vehicle (Control) | Conjugate |
| 22 | 0.15 | 0.65 |
| 26 | 1.15 | 0.68 |
| 29 | 2.30 | 1.20 |
| 31 | 3.45 | 2.24 |
| 33 | 2.33 | 3.04 |
| 36 | 6.27 | 3.14 |
| 38 | 7.55 | 4.40 |
| 40 | 10.36 | 5.54 |
| 43 | 8.21 | 5.00 |

EXAMPLE XXXIX

This Example illustrates the preparation and use of a linear polymeric polypeptide of the invention derived from HCG.

Fragment A described above (a fragment having an amino acid sequence corresponding to the 105–145 sequence of beta-HCG, with a cysteine residue added to the C-terminal thereof) was polymerized to form a hexamer. A first portion of fragment A had both its thiol groups (on the non-terminal cysteine) and its non-terminal amino group (on the lysine residue at the position corresponding to position 122 in beta-HCG) blocked. This blocked form of Fragment A was reacted with the bifunctional organic coupling reagent (or amino group activating agent) MCS in a buffered aqueous solution at pH 6.6, thereby reacting the ester portion of the MCS with the N-terminal amino group of the first portion of Fragment A. The resultant product was then reacted with a second portion of Fragment A, which was used in the same form as the first portion of Fragment A except that the C-terminal cysteine bore an unblocked thiol group, thereby reacting the remaining functional group of the MCS with the free thiol group on the second portion of Fragment A and producing a dimer in which the N-terminal of the first portion of Fragment A was coupled to the C-terminal of the second portion of Fragment A via an MCS residue. This dimer was then purified by gel filtration. The polymerization was then repeated in the same manner until a hexamer of Fragment A had been produced. Because the purification following each polymerization step was effected by gel filtration rather than by reverse-phase, high pressure liquid chromatography, the hexamer was undoubtedly somewhat impure and contaminated by traces of pentamer, tetramer etc., so that the results in the animal tests, results described below, could not be expected to be as good as would be produced using a pure hexamer.

To test the effectiveness of this hexameric polypeptide in provoking the formation of antibodies to HCG, the hexamer was formed into a vaccine using Complete Freund's Adjuvant and injected into five rabbits. Each rabbit was given three injections of the vaccine intramuscularly at 3 week intervals, each injection containing 0.5 mg. of the hexamer. Starting three weeks after the first injection, each rabbit was bled weekly and the level of antibodies to HCG in the blood determined. The following average values of antibody level were found (the figures in parenthesis represent the confidence limits i.e. average+or−standard error):

TABLE 28

| Weeks After First Injection | Antibody concentration (moles/liters × $10^{-10}$) |
|---|---|
| 3 | 5 (2–7) |
| 4 | 18 (13–22) |
| 5 | 30 (21–39) |
| 6 | 45 (30–60) |
| 7 | 58 (32–83) |
| 8 | 61 (34–86) |
| 9 | 77 (50–108) |
| 10 | 110 (50–1/2 125) |
| 11 | 100 (50–1/2 125) |
| 12 | 79 (30–119) |
| 13 | 53 (22–83) |

The above results show that even the crude hexamer preparation used in these experiments was much more strongly immunogenic than the very weakly immunogenic fragment from which it was derived.

EXAMPLE XL

This Example reports the results of experiments carried out to determine the immunogenicity and cross-reactivity with LH, of various portions of the beta-subunit of HCG.

Synthetic polypeptides corresponding to 12–16 amino acid residue portions of the sequence of beta-HCG were prepared in the same manner as in Example XXXI above. These peptides were then conjugated to diphtheria toxoid using the coupling techniques described in Example XXXI above. In all cases, the resultant conjugates contained approximately 30 molecules of the peptide per 100,000 daltons of diphtheria toxoid. The resulting modified polypeptide conjugates were then mixed with Complete Freund's Adjuvant and injected into rabbits using the same techniques as in Example XXXII above. Table 29 shows the results obtained by testing for the antibody levels to HCG and HLH in these experiments.

TABLE 29

Mean Peak Antibody Levels in Sera from Rabbits Immunized with Beta-hCG Peptide Conjugates

| Subunit Sequence | Antibody levels | M/L × $15^{-10}$ |
|---|---|---|
| 1–12 | 0.92 | 0.05 |
| 10–22 | 0.62 | 0.05 |
| 20–32 | 1.90 | 0.05 |
| 30–42 | 15.70 | 6.20 |
| 40–52 | 1.80 | 0.05 |
| 50–62 | 0.55 | 0.05 |
| 60–72 | 1.78 | 0.90 |
| 70–82 | 4.66 | 0.05 |
| 80–92* | | |
| 90–102 | 1.70 | 0.85 |
| 100–112 | 0.44 | 0.11 |
| 110–122 | 100.45 | 0.05 |
| 120–132 | 3.60 | 0.05 |
| 130–145 | 75.70 | 0.05 |

*sequence not tested

It will be appreciated that numerous changes and modifications can be made in the embodiments of the invention described above without departing from the scope of the invention. Accordingly, the foregoing description is to be construed in an illustrative and not in a limitative sense, the scope of the invention being defined solely by the appended claims.

I claim:

1. A polypeptide linear homopolymer of at least three monomers, each monomer forming said homopolymer being substantially non-immunogenic to a mammal and comprising an amino acid sequence of the beta subunit of chorionic gonadotropin endogenous to said mammal, the linear homopolymer being substantially free of non-linear polymers and immunogenic to said mammal whereby upon administration into the body of said mammal, having a capacity to induce the formation of antibodies reactive against chorionic gonadotropin endogenous to said mammal.

2. The polypeptide defined in claim 1 wherein each of said monomers comprise a synthetic peptide having the 105–145 amino acid sequence of βCG.

3. The polypeptide defined in claim 1 wherein each of said monomers comprise a synthetic peptide having the 111–145 amino acid sequence of βCG.

4. The polypeptide defined in claim 3 wherein said homopolymer comprises 4 to 14 fragments.

5. The polypeptide defined in claim 1 wherein said linear homopolymer comprises 4 to 14 fragments.

6. The polypeptide defined in claim 1 wherein said homopolymer comprises 4 to 14 fragments.

* * * * *

UNITED STATES PATENT AND TRADEMARK OFFICE
CERTIFICATE OF CORRECTION

PATENT NO. : 6,039,948　　　　　　　　　　　　　　　　　　　　　　　　Page 1 of 1
DATED : March 21, 2000
INVENTOR(S) : Vernon C. Stevens It is certified that error appears in the above-identified patent and that said Letters Patent is hereby corrected as shown below:

<u>Claim 6, column 96,</u>
Line 47, delete "1" and insert therefor ---2---.

Signed and Sealed this

Third Day of July, 2001

*Attest:*

*Attesting Officer*　　　　NICHOLAS P. GODICI
　　　　*Acting Director of the United States Patent and Trademark Office*